United States Patent
Ware

(10) Patent No.: US 7,118,742 B2
(45) Date of Patent: Oct. 10, 2006

(54) LIGAND FOR HERPES SIMPLEX VIRUS ENTRY MEDIATOR AND METHODS OF USE

(75) Inventor: Carl Ware, Solana Beach, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 0 days.

(21) Appl. No.: 09/967,604

(22) Filed: Sep. 28, 2001

(65) Prior Publication Data

US 2003/0060605 A1    Mar. 27, 2003

Related U.S. Application Data

(63) Continuation-in-part of application No. 09/549,096, filed on Apr. 12, 2000, now abandoned, which is a continuation-in-part of application No. 08/898,234, filed on Jul. 30, 1997, now Pat. No. 6,140,467.

(60) Provisional application No. 60/051,964, filed on Jul. 7, 1997.

(51) Int. Cl.
*A61K 39/395* (2006.01)
*A61K 45/00* (2006.01)
*C07K 16/28* (2006.01)
*C12P 21/08* (2006.01)

(52) U.S. Cl. .............. 424/130.1; 424/133.1; 424/143.1; 424/85.4; 530/387.1; 530/387.3; 530/388.2

(58) Field of Classification Search .......... 424/133.1, 424/143.1
See application file for complete search history.

(56) References Cited

FOREIGN PATENT DOCUMENTS

WO    WO 96/22788    *    8/1996

OTHER PUBLICATIONS

Anderson et al, Antivrial Research 21: 343-355, 1993.*
Stryer et al, in Biochemistry, Third edition, W H Freeman Company, New York, pp. 31-33, 1998.*
Ngo et al, 1994, The Protein Folding Problem and Tertiary Structure Prediction, pp. 492-495.*
Kuby et al., 1994, Immunology, second edition, pp. 85-96.*
Abaza et al, J of Protein Chemistry 11(5): 433-444, 1992.*
Van Noort et al, International Reivew of Cytology 178: 127-205, 1998.*
Bodey et al., Anticancer Research 20: 2665-2676, 2000.*
Ezzell et al., Journal of NIH Research 7: 46-49, 1995.*
Spitler et al., Cancer Biotherapy 10: 1-3, 1995.*
Ramsay et al, JAMA 282 (21): 1992-1994; 1999.*
Norberg et al, J Virology 78(19): 10755-70764.*
Whitley et al, p. 2302, in Fields Virology, vol. 2, Third edition, Lippincott-Raven publication 1996.*
Britt et al, p. 2493, in Fields Virology, vol. 2, Third edition, Lippincott-Raven publication 1996.*

* cited by examiner

*Primary Examiner*—Christina Chan
*Assistant Examiner*—Phuong N Huynh
(74) *Attorney, Agent, or Firm*—Pillsbury Winthrop Shaw Pittman LLP

(57) ABSTRACT

A novel polypeptide ligand, p30, or LIGHT, for herpes virus entry mediator, HVEM, is provided. LIGHT is useful for modulating immune responses and in inhibiting infection and/or subsequent proliferation by herpesvirus. HVEM fusion proteins are also provided. Methods for treating subjects with lymphoid cell disorders, tumors, autoimmune diseases, inflammatory disorders or those having or suspected of having a herpesvirus infection, utilizing p30 and the fusion proteins of the invention, are also provided.

31 Claims, 33 Drawing Sheets

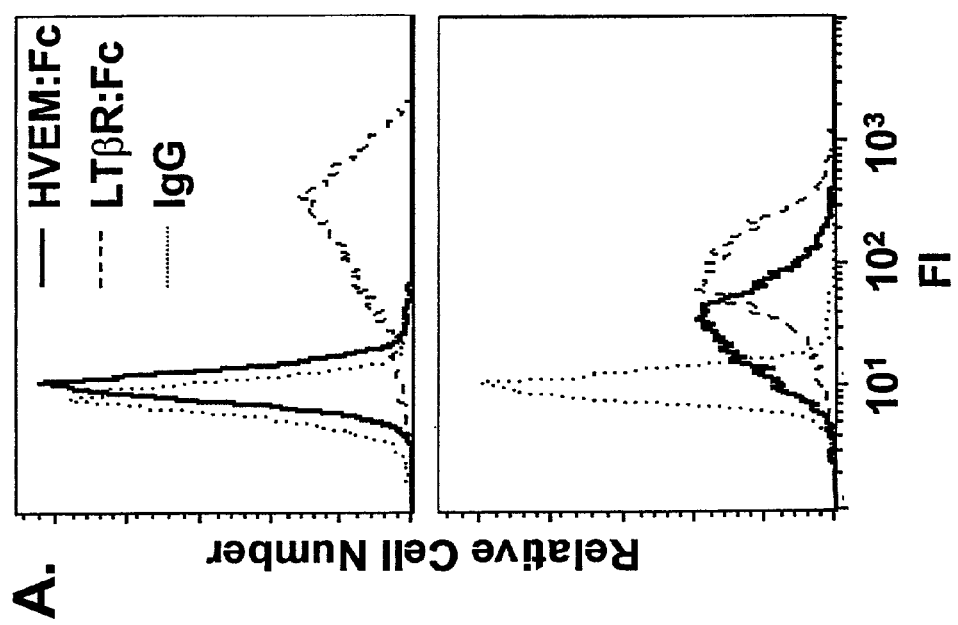

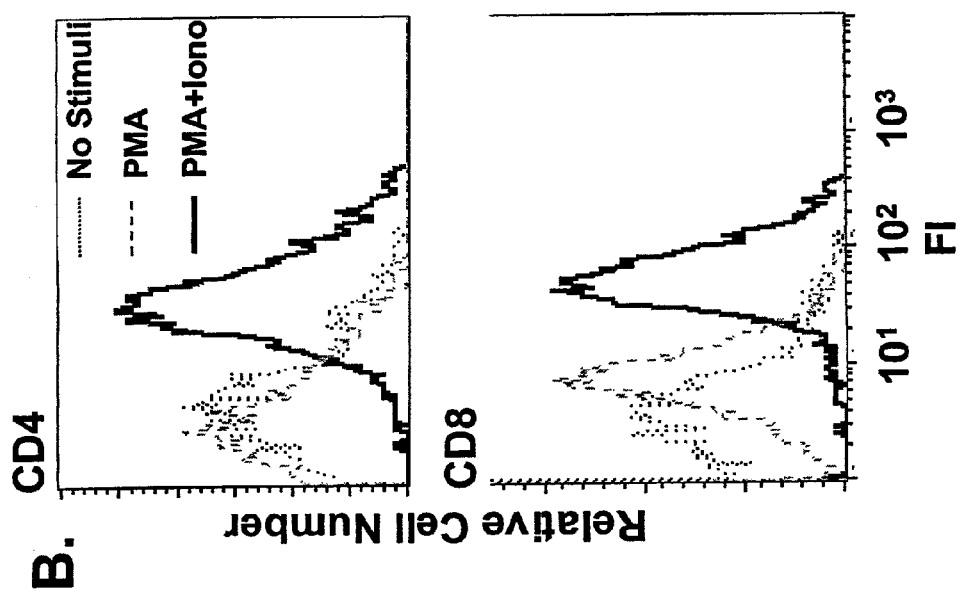
Patent Fig. 1B

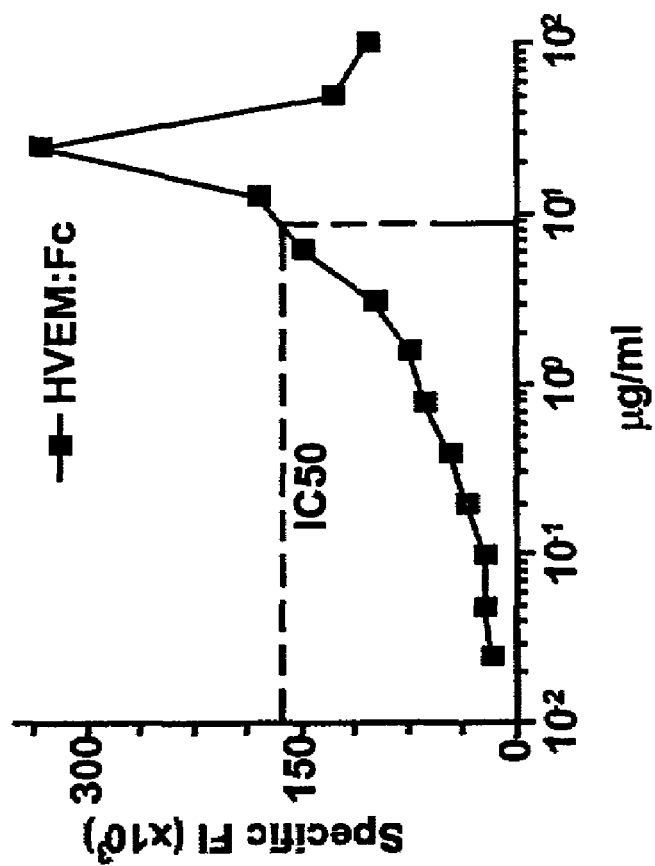
Patent Fig. 1C

LIGAND FOR HERPES SIMPLEX VIRUS ENTRY MEDIATOR AND METHODS OF USE

CROSS REFERENCE TO RELATED APPLICATIONS

This application is a continuation-in-part of U.S. Ser. No. 09/549,096, filed Apr. 12, 2000, now abandoned, which is a continuation-in-part of U.S. Ser. No. 08/898,234, filed Jul. 30, 1997 (now U.S. Pat. No. 6,140,467), which claims priority to U.S. Ser. No. 60/051,964, filed Jul. 7, 1997, and which are incorporated herein by reference in their entirety for all purposes.

STATEMENT AS TO FEDERALLY-SPONSORED RESEARCH

The United States Government has certain rights in this invention pursuant to grant nos. AI33068 and CA69381 awarded by National Institutes of Health (NIH), DHHS.

FIELD OF THE INVENTION

The invention relates generally to compounds and methods useful in regulating immune responses and viral infection.

BACKGROUND OF THE INVENTION

Herpes simplex virus (HSV), types 1 and 2, causes recurrent infections that range in severity from benign to serious. HSV emerges from latency in neurons to infect the skin and other tissues in the presence of a competent cellular immune system. The D glycoprotein (gD) of HSV, a transmembrane protein located in the virion envelope, initiates infection by binding to cellular receptors (Spear et al. (1993) Viral Fusion Mechanisms. Ed. Bentz. CRC press, Boca Raton). Recently, a cellular protein used by HSV for infection was identified and given the term HSV entry mediator (HVEM) (Montgomery (1996) Cell 87:427). HVEM is a transmembrane type 1 protein with a cysteine-rich extracellular domain that exhibits significant homology with receptors for tumor necrosis factor (TNF)-related cytokines (Smith et al. (1994) Cell 76:959; Ware et al. (1995) in, Pathways of Cytolysis. Eds. Griffiths and Tschopp. Springer-Verlag, Basel). Many of the TNF superfamily members initiate a variety of cellular responses necessary to mount effective inflammatory and immune responses.

TNF is a type 2 transmembrane protein (Pennica (1984) Nature 312:724) that is proteolyzed to form the secreted protein (Black (1997) Nature 385:729), whereas LTα lacks a transmembrane domain (Gray (1984) Nature 312:721) and is exclusively secreted as a homotrimer (in this form it was also known as TNFβ). When expressed as a surface protein, LTα is associated with a 33 kDa protein (Androlewicz (1992) J. Biol. Chem. 267:2542), termed LTβ (Browning (1993) Cell 72:847), also a type 2 transmembrane glycoprotein, in heterotrimers of α1β2 and α2β1 subunit ratios (Androlewicz (1992) supra; Browning (1996) J. Biol. Chem. 271:8618). LTα and TNF both bind and signal through two receptors, the 55–60 kDa TNF receptor (TNFR60; CD120a or type 1) (Schall (1990) Cell 61:361; Loetscher (1990) Cell 61:351) and the 75–80 kDa TNFR (TNFR80; type 2 or CD120b) (Smith (1990) Science 248:1019). By contrast, the surface LTα1β2 complex is recognized specifically by the LTβ receptor (LTβR) (Crowe (1994) Science 264:707), which does not bind either LTα or TNF (Crowe (1994) supra) whereas both TNFRs bind the LTα2β1 heterotrimer (Crowe (1994) supra; Browning (1995) J. Immunol. 154:33).

Genetic deletions of LTα and LTβ genes in mice have revealed roles for these two genes in the development of lymph nodes and Peyer's patches (De Togni (1994) Science 264:703; Banks (1995) J. Immunol. 155:1685), and along with TNF and TNFR60, are also critical cytokines controlling the formation of germinal centers and immunoglobulin isotype switching (e.g., IgA production) during immune responses in adults (Matsumoto (1996) Science 271:1289; Mariathasan (1995) J. Inflammation 45:72). Most studies have pointed towards the LTα1β2/LTβR as the critical cytokine-receptor system controlling these functions (Crowe (1994) Science 264:707; Koni (1997) Immunity 5:491; Ettinger (1996) Proc. Natl. Acad. Sci. USA 93:13102; Rennert (1996) J. Exp. Med. 184:1999).

SUMMARY OF THE INVENTION

The present invention is based on the identification of an endogenous polypeptide that functions as a ligand for HVEM, which previously was known only to bind HSV gD. This HVEM-binding ligand, also referred to as p30, or LIGHT, is provided, as well as nucleic acid sequences encoding p30 and antibodies which bind to p30. The invention also includes methods for identifying compounds that modulate viral infection, e.g., herpesvirus (e.g., CMV or HSV) infection, and methods for modulating lymphoid cell responses. Thus, the methods of the invention are useful for treating subjects with autoimmune diseases, lymphoid malignancies and viral infection associated with herpesviridae including, for example, herpesvirus and cytomegalovirus infection.

In one embodiment the invention features an assay for identifying a compound which affects an HVEM-binding agent-mediated cellular response. Also within the invention is an assay for identifying a compound which affects an LTβR-p30-mediated cellular response.

The present invention provides a method for inhibiting an inflammatory disorder in a subject, by contacting the subject with an inhibiting effective amount of an agent which prevents the interaction of p30 (LIGHT) with its receptor. The subject, tissue or cell used in the methods of the present invention may be any subject, tissue or cell, including of a mammalian specie, but is preferably human. The agents can be administered in vivo, ex vivo, or in vitro depending upon the source (e.g., whole organism, tissue or cell). For in vivo administration or contacting, delivery may be by systemic methods or topical. The agent may be any agent which prevents interaction of p30 with its receptor. Examples of such agents include the antibodies (e.g., anti-p30 antibodies), peptidomimetics, polypeptides, and fragments of HVEM of the invention.

In another embodiment, the present invention provides a fusion polypeptide comprising an HVEM polypeptide or fragment thereof operatively linked to a polypeptide of interest. The HVEM polypeptide can be from amino acid 1 to SER205 of HVEM and the polypeptide of interest an Fc region of an antibody.

In yet another embodiment, the present invention provides a polynucleotide sequence encoding the fusion polypeptide comprising an HVEM polypeptide or fragment thereof operatively linked to a polypeptide of interest.

In another embodiment, the present invention provides a vector containing the polynucleotide sequence encoding the HVEM fusion polypeptide.

In yet a further embodiment, the present invention provides pharmaceutical composition comprising the fusion polypeptide and/or polynucleotides and a pharmaceutically acceptable carrier.

The invention provides an isolated or recombinant homotrimeric p30 polypeptide comprising a monomer polypeptide having an apparent molecular weight (MW) of about 30 kilodaltons (kDa), wherein the homotrimeric polypeptide binds to a herpes virus entry mediator (HVEM) polypeptide or a lymphotoxin receptor (LTR) polypeptide under physiologic conditions. In alternative embodiments, the isolated or recombinant homotrimeric p30 polypeptide comprises isomers having a pI from about 7 to about 8.5.

The invention provides a soluble isolated or recombinant homotrimeric p30 polypeptide lacking a transmembrane domain, wherein the homotrimeric polypeptide binds to a herpes virus entry mediator (HVEM) polypeptide or a lymphotoxin β receptor (LTβR) polypeptide under physiologic conditions.

The invention provides a fusion protein comprising a p30 polypeptide of the invention and a heterologous sequence. In one embodiment, the heterologous sequence is a tag or another detectable moiety.

The invention provides a liposome comprising a p30 polypeptide of the invention, including a homotrimeric p30 polypeptide of the invention, a soluble homotrimeric p30 polypeptide lacking a transmembrane domain, a fusion protein of the invention, or a combination thereof.

The invention provides a pharmaceutical composition comprising a p30 polypeptide of the invention, including a homotrimeric p30 polypeptide of the invention, a soluble homotrimeric p30 polypeptide lacking a transmembrane domain, a fusion protein of the invention, or a liposome of the invention, or a combination thereof, and a pharmaceutically acceptable excipient.

The invention provides a pharmaceutical composition comprising a LTβR or TNFR1 agonist. In one embodiment, the agonist comprises a ligand such as a polypeptide p30 (LIGHT), LTα, TNF or LTα1β2, or an antibody, such as a fully human or humanized form, or a fusion protein or functional fragment thereof. In a particular aspect, the antibody is a monoclonal antibody denoted 3C8, 3H4 and 4H8. Pharmacuetical compositions additionally ionclude those having one or more antiviral agents (e.g. an agent for treatment of herpesvirus, such as CMV).

The invention provides antibodies having a LTβR or TNFR1 agonist activity. In one embodiment, an antibody has the binding specificity of a monoclonal antibody denoted 3C8, 3H4 or 4H8. In particular aspects, the antibody having the binding specificity of a monoclonal antibody denoted 3C8, 3H4 or 4H8 is humanized or fully human.

The invention provides a kit comprising a pharmaceutical composition and printed matter, wherein the pharmaceutical composition comprises a p30 polypeptide, wherein the p30 polypeptide comprises a homotrimeric p30 polypeptide comprising a monomer polypeptide having an apparent molecular weight of about 30 kDa, wherein the bomotrimeric polypeptide binds to a herpes virus entry mediator (HVEM) polypeptide or a lymphotoxin receptor (LTR) polypeptide under physiologic conditions, or, a soluble homotrimeric p30 polypeptide lacking a transmembrane domain, wherein the soluble homotrimeric polypeptide binds to a herpes virus entry mediator (HVEM) polypeptide or a lymphotoxin β receptor (LTβR) polypeptide under physiologic conditions, and a pharmaceutically acceptable excipient, wherein the printed matter comprises instructions for a use of the pharmaceutical composition, wherein a use comprises inhibiting virus entry into a cell or virus proliferation in a cell. The instructions can include use of the pharmaceutical composition for inhibiting virus entry into a cell or inhibiting virus proliferation in a cell in vivo. In alternative embodiments, the inhibited virus is a herpesvirus, a herpes simplex virus (HSV), a cytomegalovirus (CMV), a γ-herpesvirus or an Epstein Barr virus (EBV). The inhibition of virus entry or virus proliferation in the cell can be in a mammal, including a human.

The invention provides a kit comprising a pharmaceutical composition and printed matter, wherein the pharmaceutical composition comprises a p30 polypeptide, wherein the p30 polypeptide comprises a homotrimeric p30 polypeptide comprising a monomer polypeptide having an apparent molecular weight of about 30 kDa, wherein the homotrimeric polypeptide binds to a herpes virus entry mediator (HVEM) polypeptide or a lymphotoxin receptor (LTR) polypeptide under physiologic conditions, or, a soluble homotrimeric p30 polypeptide lacking a transmembrane domain, wherein the soluble homotrimeric polypeptide binds to a herpes virus entry mediator (HVEM) polypeptide or a lymphotoxin β receptor (LTβR) polypeptide under physiologic conditions, and a pharmaceutically acceptable excipient, wherein the printed matter comprises instructions for a use of the pharmaceutical composition, wherein a use comprises modulating diseases with unwanted lymphocyte proliferation. In alternative embodiments, the instructions comprise use of the pharmaceutical composition to modulate a T or a B lymphoma or leukemia, or an autoimmune disease. The autoimmune disease can be rheumatoid arthritis, insulin-dependent diabetes mellitus, multiple sclerosis, systemic lupus erythematosus or myasthenia gravis.

The invention provides a pharmaceutical composition comprising an expression vector encoding a p30 polypeptide having an apparent molecular weight of about 30 kDa or a p30 polypeptide lacking a transmembrane domain, wherein the p30 polypeptide forms a homotrimeric polypeptide that binds to a herpes virus entry mediator (HVEM) polypeptide or a lymphotoxin β receptor (LTβR) polypeptide under physiologic conditions.

The invention provides a kit comprising a pharmaceutical composition and printed matter, wherein the pharmaceutical composition comprises an expression vector encoding a p30 polypeptide having an apparent molecular weight of about 30 kDa or a p30 polypeptide lacking a transmembrane domain, wherein the p30 polypeptide forms a homotrimeric polypeptide that binds to a herpes virus entry mediator (HVEM) polypeptide or a lymphotoxin β receptor (LTβR) polypeptide under physiologic conditions, and a pharmaceutically acceptable excipient, and, wherein the printed matter comprises instructions for a use of the pharmaceutical composition, wherein a use comprises targeting of tumor cells or activated lymphocytes. In one embodiment, the use comprises treatment of a tumor by direct injection of the pharmaceutical composition into the tumor.

The invention provides a kit comprising an LTβR or TNFR1 agonist, and instructions for use in treating a subject having or at risk of having a herpesvirus infection. The invention provides a kit comprising a pharmaceutical composition comprising an LTβR or TNFR1 agonist and instructions for use in treating a subject having or at risk of having a herpesvirus infection. The invention provides a kit comprising an LTβR or TNFR1 agonist, an antiviral agent, and instructions for use in treating a subject having or at risk of having a herpesvirus infection. The invention provides a kit comprising a pharmaceutical composition comprising an LTβR or TNFR1 agonist, an antiviral agent, and instructions for use in treating a subject having or at risk of having a herpesvirus infection.

The invention provides a method for inducing a proliferation-inducing signal to a lymphocyte comprising (a) providing a composition that binds to cell surface expressed HVEM, and (b) contacting the lymphocyte with a proliferation-inducing amount of the composition. In alternative embodiments, the composition comprises an anti-HVEM antibody or a polypeptide comprising an anti-HVEM antibody binding site. In alternative embodiments, providing a composition that binds to cell surface expressed HVEM comprises providing a composition comprising a p30 polypeptide, a soluble p30 polypeptide, a liposome-associated p30 polypeptide, or, a vector encoding a p30 polypeptide or a cell expressing a recombinant p30 as a cell-associated p30 polypeptide. In this method, the lymphocyte can be a T cell or a B cell. The lymphocyte can be contacted in vivo.

The invention provides a method for inhibiting a p30 polypeptide-mediated cellular response comprising (a) providing an composition that inhibits binding of a cell surface expressed p30 polypeptide to a cell surface expressed HVEM or LTβR, and, (b) contacting the cell expressing the cell surface expressed p30 polypeptide or the cell surface expressed HVEM or LTβR with an amount of the composition sufficient to inhibit a p30 polypeptide-mediated cellular response. In this method, the cell can be contacted with the composition in vivo. In alternative embodiments, the inhibited p30 polypeptide-mediated cellular response comprises inhibition of a lymphocyte cellular response, the inhibited lymphocyte response is lymphocyte proliferation, and the inhibited lymphocyte is a pathogenic effector cell. The inhibited lymphocyte response can comprise modulation of a T or a B lymphoma or leukemia or an autoimmune disease. The autoimmune disease can be rheumatoid arthritis, insulin-dependent diabetes mellitus, multiple sclerosis, systemic lupus erythematosus or myasthenia gravis. The inhibited lymphocyte response can comprise modulation of a reaction to a transplant.

In one embodiment, the contacted cell expresses HVEM and the composition is a soluble p30 polypeptide. In an alternative embodiment, the contacted cell expresses LTβR and the composition is a soluble p30 polypeptide. In other embodiments, the contacted cell expresses p30 polypeptide on its cell surface and the composition is a soluble HVEM polypeptide; and, the contacted cell expresses p30 polypeptide on its cell surface and the composition is an anti-p30 antibody.

The invention provides a method for treating tumors comprising (a) providing a pharmaceutical composition comprising an expression vector encoding a p30 polypeptide having an apparent molecular weight of about 30 kDa or a p30 polypeptide lacking a transmembrane domain, wherein the p30 polypeptide forms a homotrimeric polypeptide that binds to a herpes virus entry mediator (HVEM) polypeptide or a lymphotoxin β receptor (LTβR) polypeptide under physiologic conditions, and (b) directly injecting the pharmaceutical composition into the tumor.

The invention provides a method of modulating a lymphotoxin beta receptor (LTβR)-mediated cellular response, the method comprising: (a) providing a composition that inhibits binding of an LTβR to a p30 polypeptide; and (b) contacting a cell expressing the LTβR or the p30 polypeptide with an amount of the composition sufficient to modulate the lymphotoxin beta receptor (LTβR)-mediated cellular response. In one embodiment, the cell expresses LTβR and the composition comprises a pharmaceutical composition comprising a p30 polypeptide comprising a homotrimeric p30 polypeptide comprising a monomer polypeptide having an apparent molecular weight of about 30 kDa, wherein the homotrimeric polypeptide binds to a herpes virus entry mediator (HVEM) polypeptide or a lymphotoxin receptor (LTR) polypeptide under physiologic conditions, or, a soluble homotrimeric p30 polypeptide lacking a transmembrane domain, wherein the soluble homotrimeric polypeptide binds to a herpes virus entry mediator (HVEM) polypeptide or a lymphotoxin β receptor (LTβR) polypeptide under physiologic conditions, and a pharmaceutically acceptable excipient. In one embodiment, the cell expresses a p30 polypeptide and the composition comprises an anti-p30 antibody. In another embodiment, the lymphotoxin beta receptor (LTβR)-mediated cellular response comprises binding of a herpesvirus to a cell. In one embodiment, the herpesvirus is blocked from entry into the cell. In another embodiment, the herpesvirus is inhibited from proliferating in the cell. In alternative embodiments, the herpesvirus is a herpes simplex virus (HSV), a cytomegalovirus (CMV), a γ-herpesvirus or an Epstein Barr virus (EBV).

The invention provides a method for inhibiting virus production in a cell, the method comprising (a) providing a p30 polypeptide; and, (b) contacting a cell infected with a herpesvirus or a cell susceptible to infection by a herpesvirus with an effective amount of a p30 polypeptide, thereby inhibiting herpesvirus production in the cell. In one embodiment, the entry of the herpesvirus into the cell is inhibited. In another embodiment, the contacting is in vivo and the p30 composition is provided as a pharmaceutical composition, wherein the pharmaceutical composition comprises a homotrimeric p30 polypeptide comprising a monomer polypeptide having an apparent molecular weight of about 30 kDa, wherein the homotrimeric polypeptide binds to a herpes virus entry mediator (HVEM) polypeptide or a lymphotoxin receptor (LTR) polypeptide under physiologic conditions, or, a soluble homotrimeric p30 polypeptide lacking a transmembrane domain, wherein the soluble homotrimeric polypeptide binds to a herpes virus entry mediator (HVEM) polypeptide or a lymphotoxin β receptor (LTβR) polypeptide under physiologic conditions, and a pharmaceutically acceptable excipient.

The virus can be a herpes simplex virus (HSV), a cytomegalovirus (CMV), a γ-herpesvirus or an Epstein Barr virus (EBV). In one embodiment, the contacting is in a mammal, such as a human.

In another embodiment, a herpesvirus infection (e.g., CMV, a β-herpesvirus or a γ-herpesvirus) or a disorder associated with herpesvirus infection is treated. In one aspect, a method includes contacting a subject having or at risk of having a herpesvirus infection or a disorder associated with herpesvirus infection with an amount of a LTβR or TNFR1 agonist sufficient to treat herpesvirus infection. Agonists include ligands, such as polypeptides (e.g., p30 (LIGHT), LTα, TNF or LTα1β2) and antibodies, such as fully human or humanized forms, as well as agonists that do not produce substantial apoptosis in cells infected with the virus. In additional aspects, virus proliferation, nucleic acid replication or protein expression, or virus reactivation from latency is reduced in the subject following treatment. Target subjects include subjects that are or are at risk of being immunosuppressed, subjects having an HIV infection or a tumor, subjects having or is at risk of having a blood or bone marrow, organ, or tissue transplant. Target subjects further include neonates. Disorders include pneumonia, arteriosclerosis, CMV hepatitis, CMV retinitis, CMV pneumonitis, CMV nephritis or CMV mononucleosis, child febrile illness, cytomegalic inclusion disease or a demyelinating disease (e.g., multiple sclerosis), Kaposis sarcoma, Hodgkins leukemia or non-Hodgkins leukemia or lymphoma. Various embodiments include additionally contacting the subject with an antiviral agent or other form of herpesvirus treatment.

The invention provides a method for identifying a compound that inhibits CMV infection, including (a) contacting LTβR or TNFR1 with a test compound under conditions allowing binding; (b) measuring LTβR or TNFR1 activity in the presence of the test compound; and (c) comparing activity in the presence of the test compound to the absence of the test compound, wherein an increase in LTβR or TNFR1 activity in the presence of the test compound identifies the test compound as a compound that inhibits CMV infection. In one aspect, the test compound is a library of compounds, for example, a peptide or small molecule library. In other aspects, the activity comprises activation of an NFkB target gene (e.g., ICAM1, VCAM1, interleukin-8 (IL-8) or secondary lymphoid organ chemokine (SLC), for example), or activation of IFNgamma or IFNbeta gene expression. In yet other aspects, the identified compound is tested for inhibiting CMV infection in cells or animals.

The invention provides a method for identifying a compound that inhibits CMV infection, including (a) contacting a cell that expresses LTβR or TNFR1 in the presence of CMV with a test compound under conditions allowing binding between LTβR or TNFR1 and the test compound; (b) measuring CMV proliferation, replication, protein expression or cytopathicity in the presence of the test compound; and (c) comparing CMV proliferation, replication, protein expression or cytopathicity in the presence of the test compound to the absence of the test compound, wherein a decrease in CMV proliferation, replication, protein expression or cytopathicity in the presence of the test compound identifies the test compound as a compound that inhibits CMV infection. In one aspect, the test compound is a library of compounds, for example, a peptide or small molecule library.

All publications, patent applications, patents, and other references mentioned herein are incorporated by reference in their entirety. In case of conflict, the present application, including definitions, will control. In addition, the materials, methods and examples described herein are illustrative only and not intended to be limiting.

Other features and advantages of the invention, e.g., therapy for a variety of human diseases, will be apparent from the following detailed description, from the drawings and from the claims.

BRIEF DESCRIPTION OF THE FIGURES

FIG. 1A is a pair of flow cytometric histograms showing the binding of HVEM:Fc fusion protein to II-23.D7 cells after activation with PMA (upper histogram) or PMA and ionomycin (lower histogram).

FIG. 1B is a pair of flow cytometric histograms showing the binding of HVEM:Fc fusion protein to normal human CD4+ (upper histogram) and CD8+ (lower histogram) T cells.

FIG. 1C is a line graph showing saturation binding of HVEM:Fc fusion protein to activated II-23.D7 cells.

FIG. 15A. Purification of LIGHTt66-FLAG from 293 cell supernatant. Top panel. Coomassie stained SDS PAGE gel (15%). 20 µl was loaded per well. Starting supernatant and ion-exchange purified LIGHT t66 appeared as multiple bands. Affinity purified LIGHT t66 appeared as a single band, Mr=27 kDa. Lower Panel. Western blot stained with anti-FLAG (M2). 20 µl was loaded per well. LIGHTt66-FLAG was detected with Mr=27 kDa. Relative intensity of the bands agreed with ELISA data indicating that LIGHT t66-FLAG was concentrated ×30 after the ion exchange procedure and ×100 after affinity purification. Final yield was 60–80% of starting material.

FIG. 15B. Purification of mutants of LIGHTt66-FLAG from 293T cell supernatants. Top Panel. Silver stained SDS PAGE gel. Mutants of LIGHTt66-FLAG produced using 293T cells as described. FLAG-tagged proteins were affinity purified from tissue culture supernatant using monoclonal M2 anti-FLAG antibody coupled to Affigel. 100 ng purified protein was loaded per well. All four mutants appeared as single bands, Mr=27 kDa. In some preparations an additional faint band Mr=52 kDa was present. No other contaminating proteins were detected. Lower panel. Western blot stained with M2 anti-FLAG. LIGHTt66-FLAG and its mutants were detected with Mr=27 k. In some cases a weakly reactive band with Mr=52 kDa was also detected, corresponding to the 52 kDa band detected by silver staining. This band is likely to be a dimer.

FIG. 15C. Crosslinking of LIGHTt66-myc. LIGHTt66 was crosslinked by addition of glutaraldehyde (0.1%) or BSCOES (5 nM) for 30 min at 4° C.; the reaction was stopped by addition of TRIS (20 mM, pH 8.0). Samples were analyzed by Western blotting using 9ElO (anti-myc) antibody. 200 ng was loaded per well. A, control LIGHTt66-myc, B, crosslinking with glutaraldehyde, C, crosslinking with BSCOES. In crosslinked samples bands of 52 and 76 kDa were detected, corresponding to expected Mrs for dimer and trimer.

FIG. 15D. Gel filtration analysis of LIGHTt66-FLAG. LIGHT t66-FLAG and mutants were analyzed by FPLC gel filtration on a Superose 12 column. Upper Panel. Fractions from gel filtration of LIGHTt66-FLAG were analyzed by ELISA using HVEM:Fc as capture molecule and M2 anti-FLAG as detecting antibody. Active LIGHT t66 eluted with Mr=76 kDa, indicating a homotrimeric molecule. Lower Panel. Dot blot stained with M2 anti-FLAG. Fractions from gel filtration analysis of LIGHTt66-FLAG and mutants were further analyzed by dot blotting (from above down, t66, G119E, Y173F, Q117T, L120Q). Anti-FLAG reactive material was detected only in those fractions determined by ELISA to contain homotrimeric LIGHT, demonstrating that the preparations contained no free monomer and no aggregated material.

FIG. 16A. HT29 cells were incubated with serial dilutions of LIGHT t66, LTα1β2, or TNF in the presence of IFNγ (80 U/ml)After 72 h cell viability was assessed by M1T assay. LIGHT t66 inhibited growth of HT29s with comparable efficiency to LTα1β2.

FIG. 16B. LIGHT t66 cytotoxicity is dependent on IFNγ. HT29 cells were incubated with serial dilutions of LIGHT t66 in the presence or absence of IFNγ (80 U/ml) and MTT assay was performed after 72 h.

FIG. 16C. LIGHT t66 cytotoxicity is blocked by coincubation with LTβR:Fc and HVEM:Fc. LIGHT t66 (200 pM) was pre-incubated with varying dilutions of LTβR:Fc, HVEM:Fc or Fas:Fc for 30 min before addition to HT29 cells in the presence of IFNγ. MTT assay was performed after 72 h. LTβR:Fc and HVEM:Fc, inhibited cytotoxicity of LIGHT t66 in a dose-dependent manner, whereas Fas:Fc did not affect LIGHT t66-mediated cytotoxicity.

FIG. 20A. Binding of anti-huHVEM and anti-huLTβR antibodies to HT29 cells. Cells were incubated with primary antibody (5 µ/ml) or normal mouse IgG (filled area) for 30 min at 4'C, followed by goat anti-mouse PE and analyzed by flow cytometry. Both anti-HVEM antibodies (CW1 and CW8) and both anti-LTβR antibodies (BDA8 and CDH10) stained the cells.

FIG. 20B. Effect of anti-hu HVEM antibodies on binding of LIGHT to hu HVEM. Wells of an ELISA plate coated with huHVEM:Fc (3 pg/ml) were incubated with varying concentrations of goat polyclonal anti-HVEM or the monoclonal anti-HVEM antibodies CW1 or CW8 for 30 min and then with LIGHT (0.25 nM) for 1 h before detection of bound LIGHT with monoclonal anti-FLAG (M2) and goat anti-mouse IgG-HRP. Goat anti-HVEM and CW8 markedly inhibited LIGHT binding to HVEM whereas CW1 had no effect.

FIG. 20C. Effect of anti-LTβR antibodies on binding of LIGHT to huLTβR. The experiment was conducted as described in FIG. 20B. Goat anti-LTβR and monoclonal anti-LTβR BDA8 markedly inhibited LIGHT binding to LTβR whereas CDH10 had no effect.

FIG. 20D. Effect of antibody crosslinking of huHVEM and huLTβR on growth of HT29 cells. HT29 cells were incubated with varying doses of polyclonal anti-HVEM, polyclonal anti-LTβR, or a mixture of the two. MTT assay was performed after 72 h. Antibody crosslinking of LTβR significantly reduced cell number in a dose-dependent manner, whereas antibody crosslinking of HVEM had no effect.

Inclusion of polyclonal anti-HVEM antibody had no effect on the cytotoxicity of polyclonal anti-LTβR.

Figure 20:
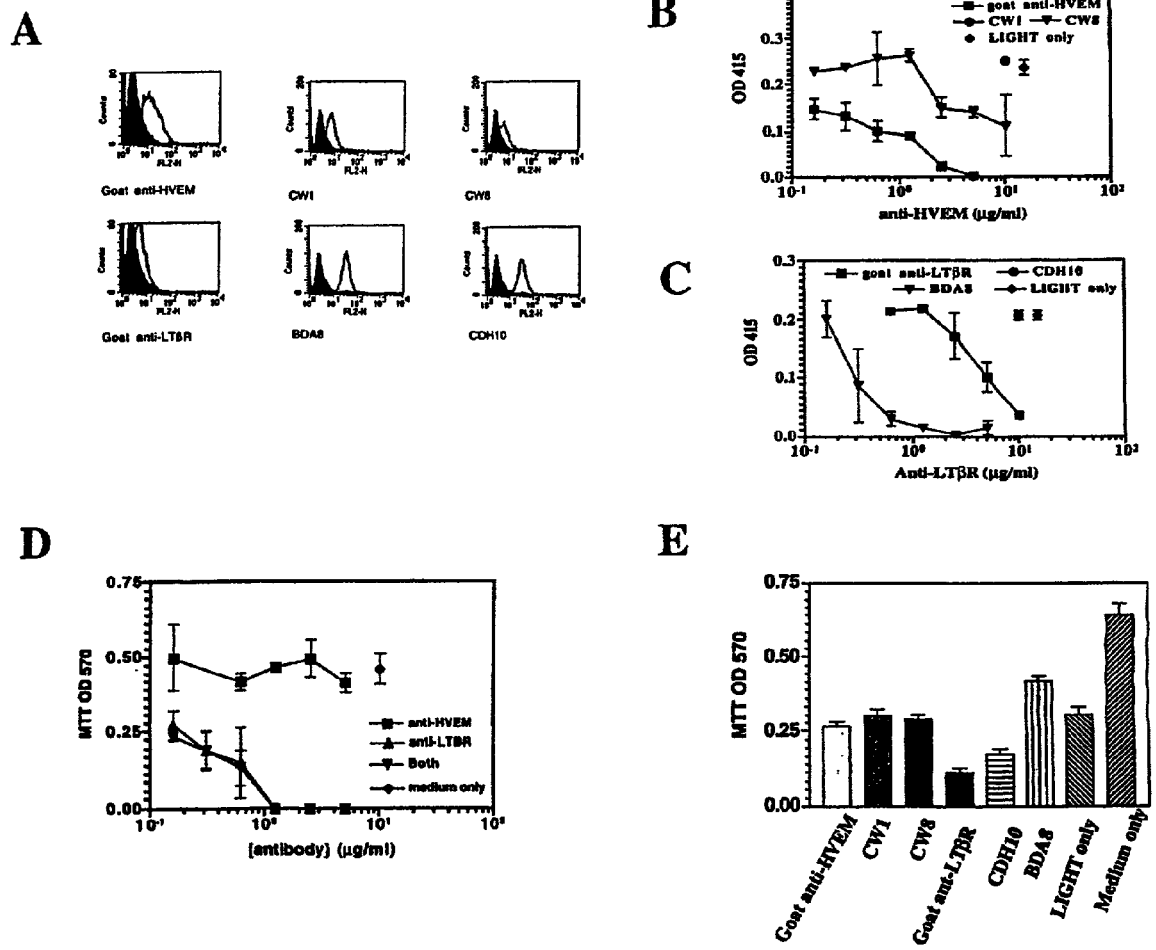
FIG. 20 shows the effect of anti-LTβR and anti-HVEM antibodies on HT29 cells.

FIG. 20E. Effect of polyclonal anti-huHVEM and anti-huLTβR on LIGHT-mediated cytotoxicity. Hi29 cells were incubated with 10 pg/ml of goat polyclonal anti-huHVEM, goat polyclonal anti-huLTβR, or the stated monoclonal antibodies for 10 min before addition of LIGHT (0.25 nM). MTT assay was performed after 72 h in culture. LIGHT alone resulted in 50% growth inhibition. Inclusion of goat polyclonal anti-LTβR and the monoclonal anti-LTβR CDH10 markedly enhanced LIGHT-mediated cytotoxicity, whereas monoclonal anti-LTβR BDA8 had a slight protective effect. Goat polyclonal anti-huHVEM and the monoclonal anti-HVEM antibodies CW1 and CW8 did not affect LIGHT-mediated cytotoxicity.

Figure 21:
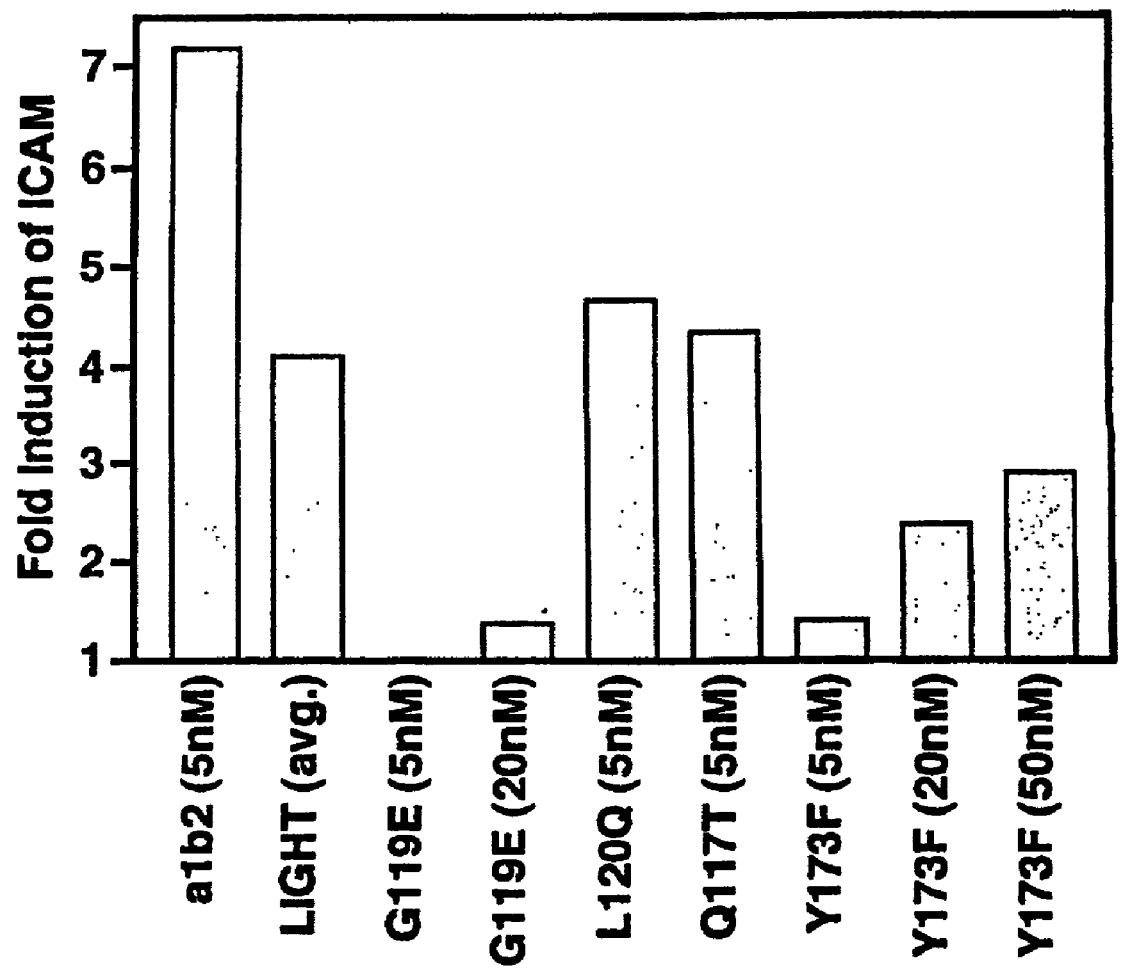

FIG. 21 shows the effect of LIGHT t66 on the up-regulation of ICAM expression in NHDF cells. NHDF cells (60,000/well) were incubated with the stated concentrations of cytokine in 600 μl of tissue culture medium. After 36 h cells were and analyzed by FACS with mAb P2A4 (Chemicon International Inc.) to determine the surface levels of ICAM-1. The fold induction represents the specific fluorescence of the cytokine-treated wells over an untreated negative control.

Figure 22:

FIG. 22 shows TRAF recruitment by receptors.

FIG. 22A. Co-immunoprecipitation of HVEM and FLAG-tagged TRAFs from the lysates of transfected 293 T cells. Protein complexes were precipitated using polyclonal rat anti-HVEM specific antibodies. Immunoblots were detected using mouse monoclonal anti-FLAG antibodies.

FIG. 22B. Coimmuno-precipitations of LTβR and FLAG-tagged TRAFs from the lysates of transfected 293 T cells. Protein complexes were precipitated using goat anti-LTβR specific antibodies. Immunoblots were detected using mouse monoclonal anti-FLAG antibodies. Cells were transfected with single vectors or with vectors in combination as indicated in the figure and described in experimental procedures. pBABE was included as a negative control.

Figure 23:
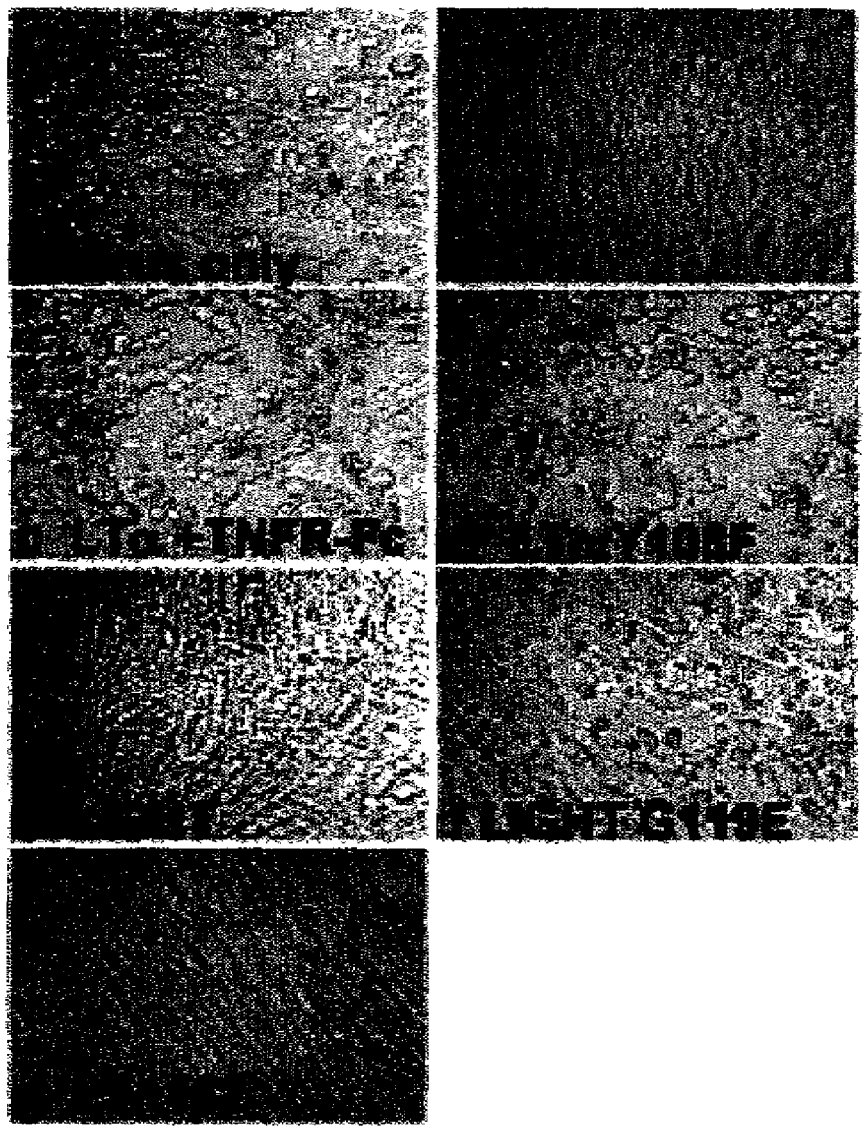

FIG. 23 shows inhibition of HCMV-induced cytopathicity by lymphotoxins and LIGHT. NHDF were infected with HCMV at an MOI of 0.01, and various purified recombinant cytokines were added to medium at a final concentration of 5 nM. After culture for 7 days the cytopathic effect was visualized by light microscopy (20× magnification). (a) NHDF infected with virus in medium or in medium with, (b) LTα; (c) LTα with TNFR1-Fc (25 pg/ml); (d) mutant LTαY108F; (e) LIGHT; f. mutant LIGHTG119E; g. LTαP1β2.

Figure 24:
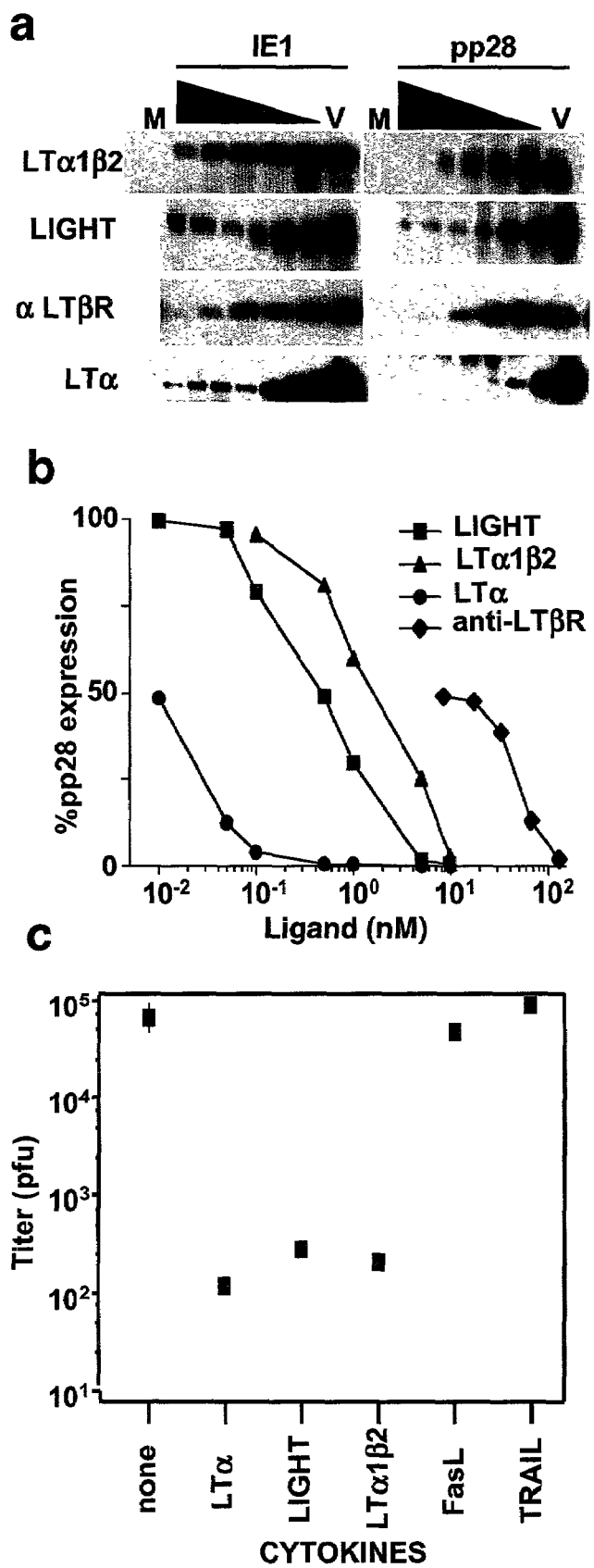

FIG. 24 shows HCMV protein expression in lymphotoxin-treated cells. a. HCMV infected fibroblasts (MOI=0.01) treated with indicated purified cytokines, and cells were harvested and analyzed for the major immediate early I protein (IE1) or late tegument protein (pp28). M, mock; V, virus with no cytokine added. b. The percentage of maximal protein expression in the western blot was calculated as a ratio of the pp28 band density in cytokine treated cells to cells infected with virus in the absence of cytokine. c. Infectious virus production (±SD) was measured in supernatants collected from NHDF infected with HCMV alone, or infected in the presence of LTα (0.1 nM), LTα1β2 (1 nM), or LIGHT (1 nM), FasL (12 nM) or TRAIL (12 nM). Cytokine dose response curves and viral titers were performed at least 3 times; data from a single representative experiment is shown.

Figure 25:
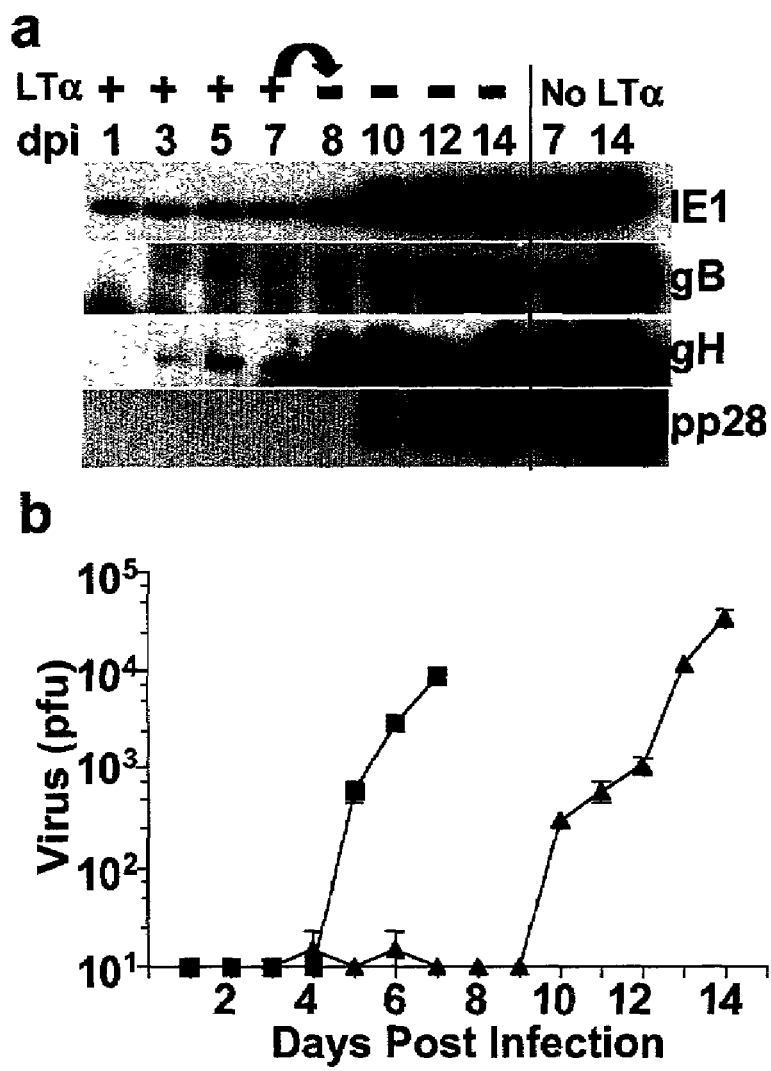

FIG. 25 shows that the anti-viral effect of LT is reversible. a. NHDF were infected with HCMV at an MOI of 0.01 and cultured with LTα (1 nM)(+). After 7 days, the medium was replaced with fresh medium without LTα(−), and virus replication was allowed to proceed for an additional 7 days. Cells were harvested at the indicated time post infection and virus protein expression analyzed by Western blot (IE1, gB, gH and pp28). The "no LTα" lanes represent HCMV proteins at 7 or 14 in the absence of LTα. b. HCMV titers (±SD) were measured every 24 hours after infection of NHDF (MOI=0.01) for cells infected in the absence of LTα (n), or with LTα for the initial 7 days and then was removed for days 8–14 (s).

Figure 26:
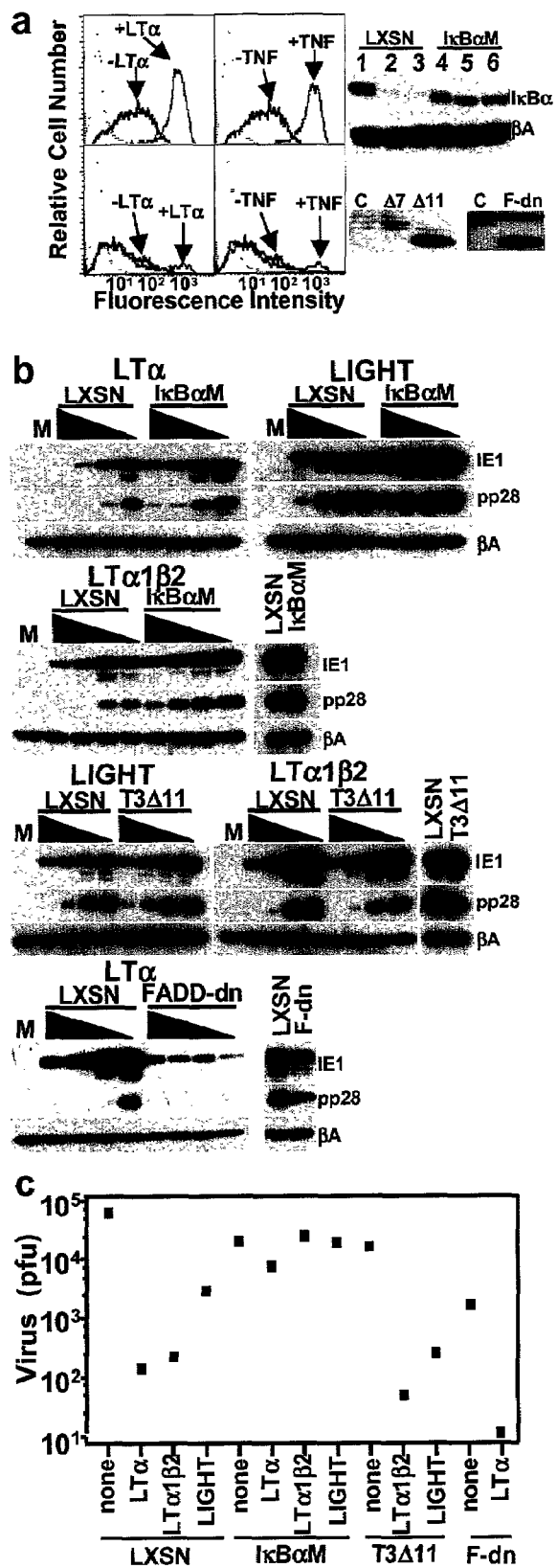

FIG. 26 shows that NFκB, but not TRAF3 or FADD, is critical for anti-HCMV signaling by TNFR1 and LTβR. a. NHDF were transduced with retroviral vectors expressing either a dominant negative (dn) IκBα mutant (IkBαM), TRAF3.D11 mutant, FADD-dn (F-dn), or empty vector (LXSN). NHDF-IκBαM cells were treated with TNF or LTα (1 nM) for 24 hrs and ICAM-1 expression was measured by flow cytometry (LXSN, upper 2 panels; IκBαM, lower 2 panels). Cell lysates were prepared and analyzed by Western blot for expression of IkBα, FLAG tagged TRAF3.D11 and FADD-dn mutants. For the IκBα degradation assay, cells were either mock treated (lanes 1,4) or treated with 1 nM TNF (lanes 2,5) or LTα (lanes 3,6) in the presence of 10 μg/ml cycloheximide for 4 hours. C, control LXSN cell lysate. b. NHDF expressing dominant negative mutants were compared to control cells (LXSN) for the ability of LTα, LTα1β2 or LIGHT to inhibit expression of IE1 and pp28. Blots were reprobed with an anti-β-actin (βA) antibody. Concentrations of cytokines or antibodies added to the culture medium were: LIGHT and LTα, serial 10 fold dilution starting at 10 nM; LTα1β2, 5 nM, 1 nM, 0.1 nM and 0.01 nM. c. Supernatants were collected from HCMV infected NHDF cell lines treated with cytokine (LTα, 0.1 nM; LTα1β2, 1 nM; LIGHT, 1 nM) 7 days and then analyzed for plaque forming units (PFU). HCMV PFU were determined in quadruplicate, and SD are contained within the symbols. Western blots and titers were performed at least 3 independent times, and representative results are shown.

Figure 27:
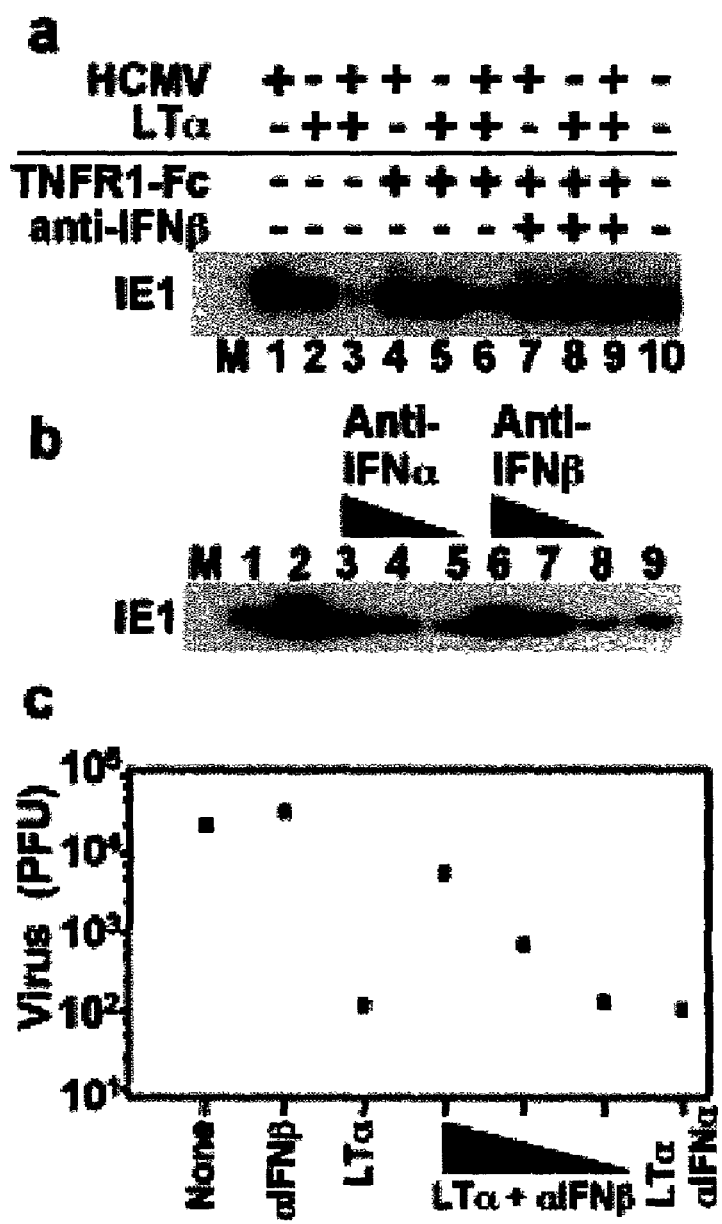

FIG. 27 shows that the anti-HCMV activity of LT is mediated through induction of IFNβ. a. Medium from NHDF infected with HCMV (MOI=0.01)(lanes 1,4,7), treated with 1 nM LTα (lanes 2, 5, 8), or infected and treated with LTα (lanes 3, 6, 9) was collected after 2 days and transferred to NHDF freshly infected with HCMV (MOI=0.01). The medium from infected cells was untreated (lanes 1–3), or treated with 25 μg/ml TNFR1-Fc (lanes 4–6), or 25 μg/ml TNFR1-Fc and 500 units anti-IFNβ neutralizing antibody (lanes 7–9). Cells were harvested and analyzed for IE1 expression by Western blot. b. NHDF cells were infected with HCMV (MOI=0.01) and at the time of infection, treated with LTα (1 nM) (except for lane 2) with anti-IFNα, or anti-IFNβ neutralizing antibodies. Cells were harvested 7 days after infection and analyzed for expression of IE1 by western blot. M, mock infected cells; lane 1, LTα alone; lane 2, virus only. Cells were treated with 1 nM LTα (lanes 3–9). Dose titration (500 units serial diluted 10 fold) with anti-IFNα (lanes 3–5), anti-IFNβ (lanes 6–8) or anti-IFNγ neutralizing antibodies (25 mg/ml) (lane 9). c. Supernatants were collected from NHDF infected with HCMV alone (none), or infected in the presence of anti-IFNβ neutralizing antibody (αIFNβ, 500U), LTα (1 nM), LTα plus neutralizing anti-IFNβ (500U, 50U, 5U) or anti-IFNα antibody (500U) as in (b).

Figure 28:
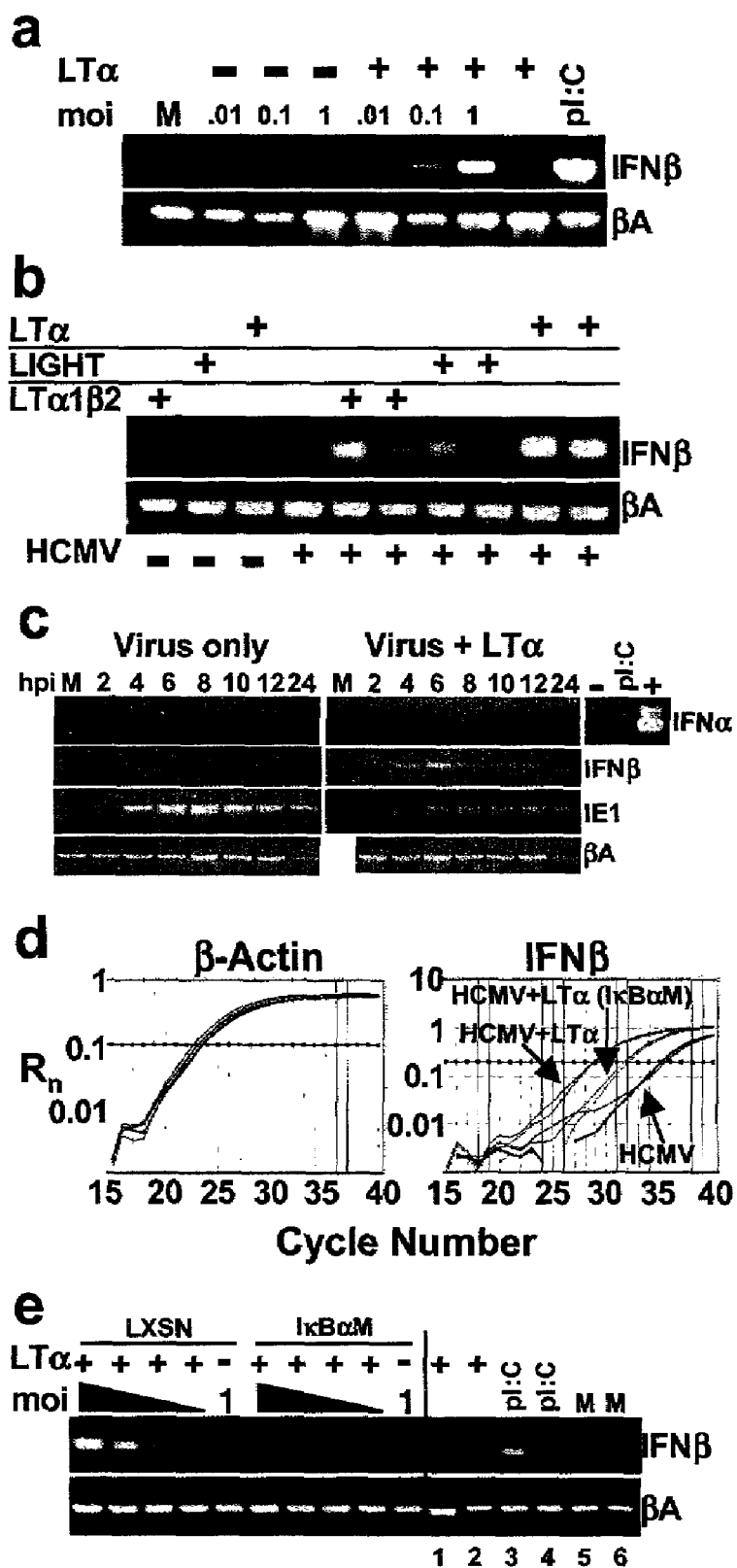

FIG. 28 shows that signaling through TNFR1 and LTβR induces transcription of IFNβ in HCMV infected cells. a. NHDF were infected with HCMV at indicated MOI in medium with or without LTα (1 nM). b. NHDF were infected with HCMV (MOI=1) and treated with LTα, LTα1β2 or LIGHT (5 nM and 1 nM each) or treated with cytokine without virus infection (5 nM). c. NHDF infected with HCMV (MOI=1) plus or minus LTα (1 nM) were harvested at various hours post infection (hpi) for analysis of IFNα, IFNβ and HCMV IE1 expression levels. +, amplification of IFNα from NHDF genomic DNA. d. Real time PCR was performed on NHDF-LXSN and NHDF-IκBαM cells infected with HCMV (MOI=1) with or without LTα (1 nM) in order to quantify induction of IFNβ mRNA. Quantification of βactin (βA) mRNA was performed in parallel to allow for normalization and calculation of fold difference in IFNβ induction. Four independent experiments were performed, and the level of IFNβ in infected cells treated with LTα was increased by 48–103 fold (mean=77+/−26). e. NHDF-LXSN or NHDF-IκBαM cells were infected with HCMV at MOI (1, 0.5, 0.25, 0.125 from left to right) and incubated in medium with or without LTα (1 nM). Right panel, NHDF-LXSN (lanes 1,3,5) and NHDF-IκBαM (lanes 2,4,6) cells were treated with LTα (lanes 1,2), polyI:C (lanes 3,4) or mock infected (M) (lanes 5,6). For all panels except c, cells were harvested 4 hours post infection for isolation of total cell RNA; M, mock infected. NHDF were treated with polyI:C (100 mg/ml) with (panel a,c) or without (panel e) cycloheximide (10 mg/ml) for 4 or 6 (panel c) hours. All PCR was performed in the linear range excepting panels (a) and (c) (IFNα only) to allow for detection of low level induction.

Figure 29:
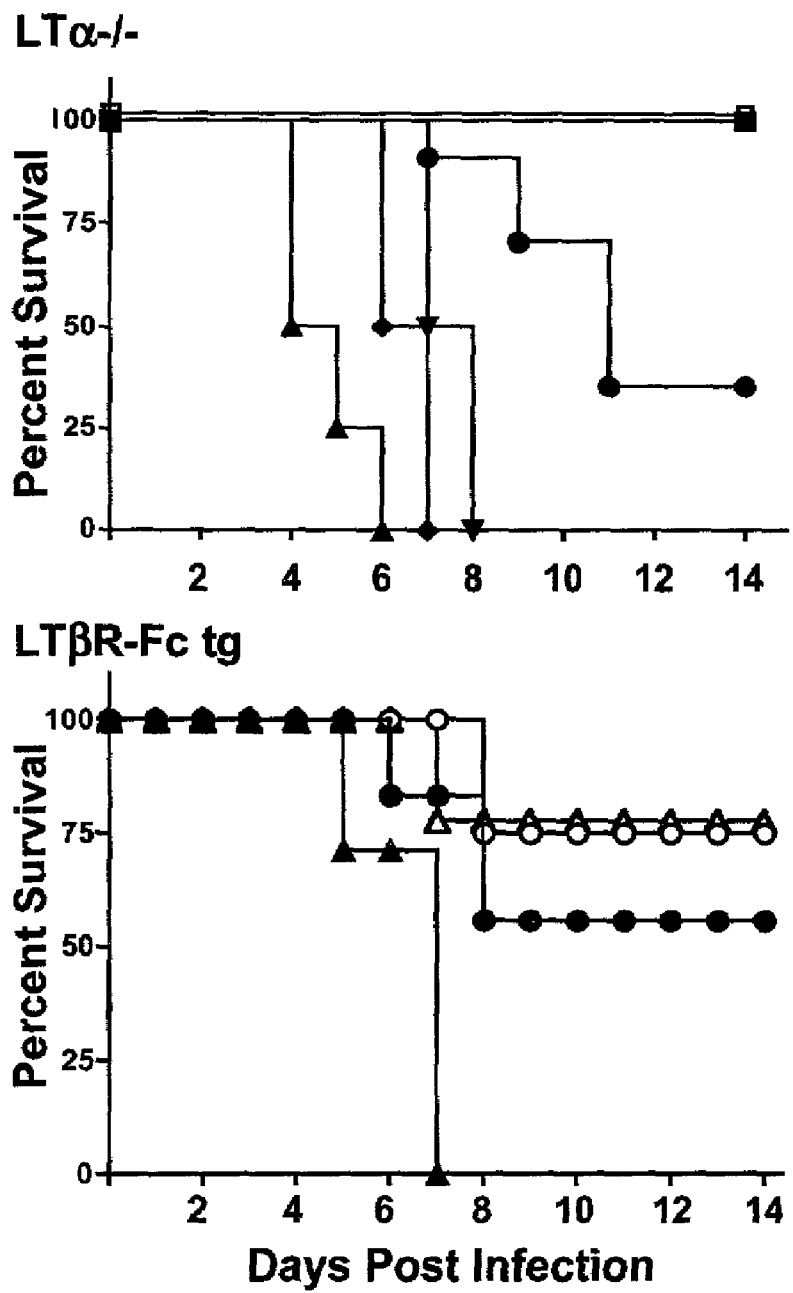

FIG. 29 shows the increased susceptibility of LTα−/− and LTβR-Fc Tg mice to MCMV infection. Upper panel. Groups of LTα deficient mice (n=4 to 6) were infected with MCMV Smith strain at a dose of MCMV, $5\times10^3$, $4\times10^4$, $8\times10^4$, $2\times10^5$, or $5\times10^5$ PFU per mouse. Control wild type mice (C57/BL6; n=4 per group) were infected with $1\times10^6$ PFU/mouse and the viability of all mice was monitored daily for 2 weeks. Lower panel. Groups of LTβR-Fc transgenic mice (filled symbol) or age/sex matched littermate control mice (open symbol)(n=4 to 6) were infected with MCMV at $8\times10^4$ or $2\times10^5$ PFU per animal. Both LTβR-Fc(+) and control mice infected with doses at or below $4\times10^4$ PFU/mouse demonstrated 100% survival at 14 days post infection. These studies were repeated on three separate occasions for the LTα−/− and twice for the LTβR-Fc(+) mice.

Figure 30:
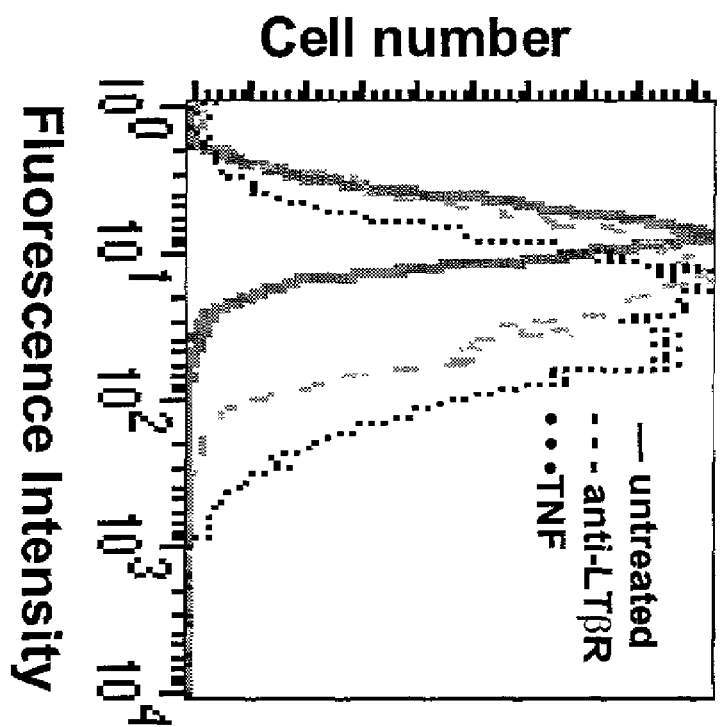

FIG. 30 shows the agonist activity of the LTβR antibody (denoted anti-LTβR). Fluorescence intensity indicates the amount of VCAM-1.

DETAILED DESCRIPTION OF THE INVENTION

The invention provides a novel ligand for HVEM, or p30 and functional variations and fragments thereof. This novel ligand, which can be found as a membrane protein and can function as a cytokine, is also called LIGHT, because this polypeptide is homologous to Lymphotoxins, exhibits Inducible expression, and competes with HSV Glycoprotein D for HVEM, a receptor expressed by T lymphocytes. Because LIGHT can compete with HSV glycoprotein D for HVEM, homotrimeric soluble forms of this polypeptide can be used to block the entry of herpesvirus into cells. Thus, this novel HVEM ligand can be used to treat or prevent herpesvirus infections, such as β-herpesvirus and cytomegalovirus.

LIGHT also bind to the lymphotoxin beta receptor (LTβR).

Experiments involving inhibition of binding of a fusion protein containing the extracellular domain of the TNF receptor (TNFR) related polypeptide, HVEM, showed that the both malignant and normal human T-cells expressed LIGHT, the cell surface ligand for HVEM.

The present invention is also based upon the discovery that HVEM polypeptides have an antagonistic effect on inflammation. In particular, HVEM fusion proteins are capable of inhibiting inflammation when administered to a subject.

Definitions

It must be noted that as used herein and in the appended claims, the singular forms "a", "and", and "the" include the plural unless the context clearly dictates otherwise. Thus, for example, reference to "a cell" includes a plurality of such cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

As used herein, to "inhibit" or "inhibiting" activity is to reduce that activity a measurable amount, such as a reduction of at least 30% or more. Where there are multiple different activities that may be inhibited (for example, preventing cell recruitment, production of pro-inflammatory mediators, cell or viral entry, viral activation, viral replication, or viral progression), the reduction of any single activity (with or without the other activities) is sufficient to fall within the scope of this definition. In addition, where a single or multiple agents are administered to inhibit activity, the reduction by a single agent of any single activity or the reduction by a combination of agents of any single activity is sufficient to fall within the scope of this definition. An "inflammation inhibiting amount" means that amount of an inflammatory agent necessary to modulate, inhibit, or suppress inflammatory responses or symptoms.

Inflammation

Inflammation results from a number of individual and related cascades or reactions caused by pro-inflammatory mediators including cytokines, prostaglandins, leukotrienes, chemokines, adhesion molecules (e.g., LFA-1) and others known to those of skill in the art. For example, receptors play a pivotal role in permitting viral entry into cells. The ligands for these receptors are also important. The ligands along with pro-inflammatory mediators such as cytokines are the main stimulators of cells but also play another role in amplification of the inflammatory cascade. These soluble inflammatory mediators are derived mainly from T cells. Once produced they can act in a paracrine and autocrine fashion to further activate cells in their vicinity and recruit additional T cells to the site of inflammation. These additional lymphocytes are themselves activated, contributing to the amplifying inflammatory cascade. Immunosuppressive activity, as used herein, refers to inhibiting or decreasing the ability of B and T cells to react or to be recruited or become activated to a site of inflammation.

Other signals which activate inflammatory cells include binding of an adhesion receptor, for example, LFA-1 (CD11a and CD18), to one of its counter-receptors such as ICAM-1 (CD54) (Staunton et al. (1990) Cell 61:243–254). If the second signal is blocked, the antigen-specific T-cells are induced to die by apoptosis or to enter a state of cellular anergy. Blockage of this interaction by monoclonal antibodies to LFA-1 and ICAM-1 results in increased survival time for mice receiving a heart allograft (Isobe (1992) Science 255:I 125–1 127). Accordingly, the compositions and methods of the invention may be used alone or in combination with other anti-inflammatory agents including non-steroidal anti-inflammatory drugs, steroids, antibodies, receptor antagonists and others easily identifiable in the art.

As used herein "inflammation" means the process or series of events that are elicited by numerous stimuli (e.g., infectious agents, ischemia, antigen-antibody interactions, and thermal or other physical injury). Inflammation is characterized by an increase in erythema, edema, tenderness (hyperalgesia), and pain at the inflamed site. An inflammatory reaction or cascade is generally recognized as having a number of distinct stages, for example, vasodilation and increased capillary permeability; an infiltration of leukocytes and phagocytes; and a stage of tissue degeneration and fibrosis. As used herein an "inflammatory disorder" means any number of diseases characterized as having part of its pathogenesis and inflammatory cascade or reaction resulting in inflammation. Such disorders include, for example, arthritis, psoriasis, inflammatory bowel disease, infectious agents such as herpes, and others known to those of skill in the art.

Experiments involving inhibition of binding of a fusion protein containing the extracellular domain of the TNF receptor (TNFR) related polypeptide, HVEM, showed that both malignant and normal human T-cells expressed a cell surface ligand for HVEM. Competitive inhibition experiments showed that the HVEM ligand has characteristics in common with LTαβ heterotrimers and LTα, but also has features that distinguish it from LTα1β2 and TNF. Thus, LTα2β1 could be a putative surface ligand recognized by HVEM, with the caveat that the HVEM binding site on LTα2β1 is not the same as TNFR60. Alternatively, HVEM might recognize a novel ligand. A biochemical approach was used to distinguish between these possibilities.

Figure 4:
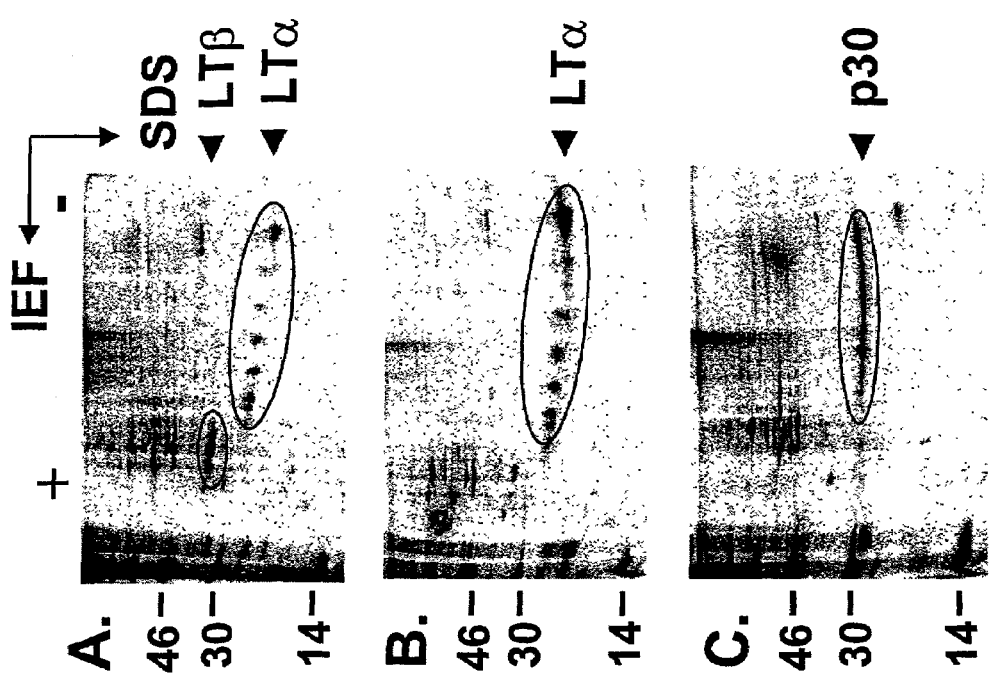
FIG. 4A is an autoradiogram obtained from a 2 dimensional isoelectric focusing/SDS-PAGE gel of a precipitate obtained by treating an extract of activated II-23.D7 cells with mLTβR:Fc fusion protein.
FIG. 4B is an autoradiogram obtained from a 2 dimensional isoelectric focusing/SDS-PAGE gel of a precipitate obtained by treating an extract of activated II-23.D7 cells with TNFR60:Fc fusion protein.
FIG. 4C is an autoradiogram obtained from a 2 dimensional isoelectric focusing/SDS-PAGE gel of a precipitate obtained by treating an extract of activated II-23.D7 cells with HVEM:Fc fusion protein.

Immunoprecipitation and sodium dodecyl sulfate polyacrylamide gel electrophoresis (SDS-PAGE) studies demonstrated the presence of a novel 30 kDa polypeptide ligand (p30) for HVEM on the surface of T cells that was antigenically distinct from both LTβ and LTα. Affinity chromatography purification and two-dimensional electrophoresis showed that p30 is also physically distinct from LTα and LTβ in that it has a molecular weight of 30 kDa and a pI of about 7–8.5 (FIG. 4C). In addition, these studies showed that active p30 (e.g. its trimeric form) is also recognized by LTβR but not by TNFR. The p30 polypeptide is also referred to as LIGHT in the recent literature (see for example, Mauri et al., Immunity, 8:21(1998)).

Binding inhibition experiments demonstrated that soluble gD-1 (gD from HSV-1) and a mutant of gD-1, gD-1 Δ290–299t) bind to HVEM but not to LTβR or TNFR60. This result suggests that gD-1 has co-evolved specifically for binding to HVEM, even though HVEM binds to ligands that are recognized by TNFR60 and LTβR. Furthermore, the findings indicate that gD-1 is a membrane-anchored virokine of the lymphotoxins and may modulate HVEM signaling activities during entry or egress of HSV from the infected cell.

In vitro cell culture studies showed that anti-HVEM antibody enhanced proliferation of both naive and memory T cells. Similar experiments indicated that signaling through HVEM provided an activating stimulus to B cells and that a positive stimulus, without a counterbalancing negative stimulus via the TNFR, may be a unique property of the p30 HVEM ligand. These results indicate that the physiologic functions of the HVEM ligand is likely to be distinct from TNF and LTα1β2. The identification of a novel 30 kDa ligand for HVEM raises the possibility that this ligand, may be responsible for physiological responses previously ascribed to LTα or LTβ. The discoveries presented here provide a deeper understanding of the LT/TNF cytokine system and herpes virus that suggest new approaches for controlling these cytokines in disease processes as well as affecting inflammation due to infection and injury.

Together, the results indicate that antagonist and binding agents such as, for example, Fc fusion proteins containing HVEM or LTβR will modulate the action of LTα and the 30 kDa HVEM ligand, p30. The results also indicate that antagonists and binding agents (e.g., antibodies and the fusion protein of the invention (e.g., HVEM:Fc)) are also useful in modulating inflammation and inflammatory responses. As discussed above, HVEM binding activates B cells and thus a modulation in the interaction of HVEM with its ligand reduces the activation of inflammatory cells and activation of the inflammatory cascade. Similarly, fusion protein HVEM could be used to identify specific inhibitors of the ligand receptor-complexes, such as monoclonal antibodies or peptides or small organic compounds. Inhibitors of p30 or LTα interactions with HVEM, or p30 interactions with LTβR, could be used to modulate diseases where unwanted lymphocyte proliferation occurs, including T and B lymphomas or leukemias, or in autoimmune diseases, such as rheumatoid arthritis, insulin-dependent diabetes mellitus, multiple sclerosis, systemic lupus erythematosus, myasthenia gravis, and inflammation, for example, arthritis, psoriasis, inflammatory bowel disease, asthma, and other known in the art.

Similarly, herpesvirus gD-1 could be used to inhibit immune reactions where LTα, p30 and HVEM signaling are implicated as effector molecules. LTα or soluble forms of the 30 kDa HVEM ligand (generated by deletion of its predicted cytoplasmic and transmembrane domains e.g. LIGHT-t66 described below) may function as inhibitors of viral infection including, for example, infection by Herpes viridae (e.g., alphaherpes virinae, betaherpes virinae and gammaherpes virinae) and recrudesces by blocking the ability of virus to enter a cellular target.

Like TNFRs, HVEM has a dual ligand specificity, binding to LTα and the trimeric form (e.g., 90 kD form) of LIGHT, a membrane bound form of the ligand, p30. The LTα Tyr108Phe mutation destroys HVEM binding as it does for TNFR60 and TNFR80. The inability of TNFR60 to block HVEM binding to the surface 30 kDa form indicates that surface LTα2β1 is not an HVEM ligand.

Furthermore, LIGHT (p30) differs from LTα because it is antigenically distinct and remains cell-associated, unlike LTα which is exclusively secreted. Thus, the HVEM binding protein (p30) is predicted to contain a stretch of hydrophobic residues forming a transmembrane domain arranged as a type-II transmembrane configuration similar to other proteins related to TNF. This does not exclude the possibility that p30 might also be modified in other ways (e.g., lipid modification) to allow attachment to the cell surface. Furthermore, this protein should share regions of sequence homology with LTα and LTβ and related cytokines that define this superfamily and contain a C-terminal extracellular domain of approximately 150–160 residues.

The inventors' findings also indicate that HVEM is a specific receptor for LTα, a property that clearly distinguishes it from the TNF binding receptors, TNFR60, also referred to as TNFR1, and TNFR80, also referred to as TNFR2. This property will allow an HVEM fusion protein or similar protein to antagonize LTα specifically without inhibiting TNF or LTα1β2 functions.

Figure 8:
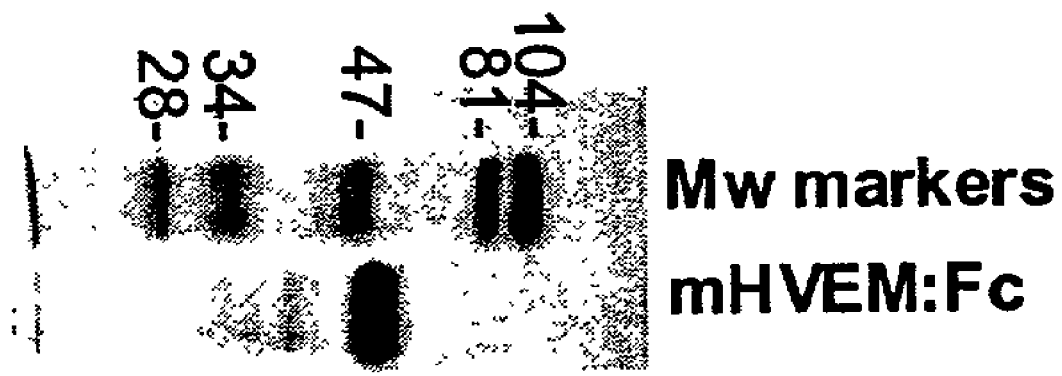
FIG. 8 shows an SDS-PAGE gel stained for protein that shows a definitive band of about 58 kDa, representative of the fusion protein mHVEM:Fc, see Example 6.

The present invention provides antagonists and binding agents, such as, e.g., a soluble, homotrimeric LIGHT or an HVEM fusion polypeptide. The HVEM fusion polypeptide can be characterized as having a molecular weight of about 58 kDa as determined by reducing SDS-PAGE, as demonstrated in FIG. 8, see Example 6.

The present invention also provides a substantially pure LIGHT, or p30 polypeptide. The p30 polypeptide is characterized as having a predicted molecular weight of 30 kDa as determined by reducing SDS-PAGE and a pI in the range of about 7–8.5 (FIG. 4C). p30 exists in less than ten, such as less than eight, particularly less than six, (e.g., three, four or five) isomeric forms. The invention also provides LIGHT, or p30, as a homotrimer. As demonstrated in the examples, below, p30 can be expressed as a homotrimer, and, when expressed as a recombinant, truncated, soluble form, it is secreted exclusively as a homotrimer. The LIGHT polypeptide can be cell bound, i.e., is not secreted. In its cell surface form, p30 binds HVEM and LTβR.

The term "substantially pure" as used herein refers to polypeptide which is substantially free of other proteins, lipids, carbohydrates or other materials with which it is naturally associated. One skilled in the art can purify such polypeptides and fusion proteins using standard techniques for protein purification (see, e.g., Protein Purification, Principles and Practice, second edition (1987) Scopes, Springer Verlag, N.Y.). For example, a substantially pure HVEM:Fc polypeptide will yield a single major band of about 58 kDa on a reducing SDS-PAGE gel. The LIGHT p30 polypeptide will yield a single major band of about 30 kDa on a reducing SDS-PAGE gel; in its homotrimeric form, it forms a single major band of about 90 kDa on a non-reducing gel (which does not disturb the trimeric tertiary structure).

The invention includes a functional fusion polypeptide and functional fragments thereof. As used herein, the term "functional polypeptide" refers to a polypeptide which possesses a biological function or other activity, such as the ability to bind to a receptor, which can be identified through routing and defined functional and receptor binding assays (see, e.g., the Examples below), and which, e.g., are associated with particular biologic, morphologic, or phenotypic alterations in the cell, or binding events, such as the ability of a soluble LIGHT polypeptide of the invention to block entry of a herpesvirus.

"Functional fragments" as used herein include subsequences of the polypeptides of the invention which a biological function, as described above. For example, fusion polypeptides of the invention can include fragments of, e.g., LIGHT or HVEM. For example, the invention provides fragments of HVEM and a second polypeptide sequence so long as an activity of substantially the same as that of HVEM:Fc remains, e.g., modulation of cellular responses by inhibiting binding of HSV to HVEM, antigenicity, or inhibition of inflammation. Smaller peptides containing the biological activity of HVEM or HVEM fusion polypeptides are included in the invention. One of skill in the art can assay for functional activity of such polypeptides by standard methods, e.g., viral plaque reduction assay or cell activation assays including cytokine production assays and measurement of inflammatory responses as described in the Examples. Similarly, functional fragments of p30 may be determined through a defined functional assay and which is associated with a particular biologic, morphologic, or phenotypic alteration in the cell.

The invention provides polypeptides with minor modifications of the LIGHT (p30), HVEM or fusion proteins (e.g., p30 of HVEM fusion protein) primary amino acid sequences. This can result in proteins which have substantially equivalent activity, e.g., as compared to the p30, the LIGHT-t66, and other mutants described below; and, HVEM:Fc polypeptide, as described herein. Such modifications can be specifically engineered, e.g., as generated by site-directed mutagenesis. Alternatively, they can be spontaneous mutations. All of the polypeptides produced by these modifications are within the scope of the invention so long as the binding or biological activity of LIGHT (p30) or HVEM:Fc is present, e.g., modulation of cellular responses by binding to HVEM and LTβR or inhibiting binding of HSV to HVEM or modulation of inflammation. Further, deletion of one or more amino acids can also result in a modification of the structure of the resultant molecule without significantly altering its activity (e.g. LIGHT-t66, see below).

Thus, the invention includes smaller, active (i.e., "functional") LIGHT (p30), including truncated, soluble homotrimeric forms, and HVEM molecules having alternative utilities. For example, amino or carboxyl terminal amino acids which are not required for activity can be removed. For example, the HVEM:Fc fusion polypeptide (described below) is characterized as having amino acids 1 through 205 of HVEM. Another example includes a truncated soluble homotrimeric p30 protein, the LIGHT-t66, described in detail in Example 12, below.

The polypeptides of the invention also include conservative variations, mimetics and peptidomimetics of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The terms "mimetic" and "peptidomimetic" refer to a synthetic chemical compound that has substantially the same structural and/or functional characteristics of the polypeptides, e.g., translocation domains or odorant-ligand binding domains or chimeric receptors of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_{2-O}$), thioether (CH$_2$-S), tetrazole (CN$_{4-}$), thiazole, retroamide, thioamide, or ester (see, e.g., Spatola (1983) In: *Chemistry and Biochemistry of Amino Acids, Peptides and Proteins*, Vol. 7, pp 267–357, "Peptide Backbone Modifications," Marcell Dekker, NY). A polypeptide can also be characterized as a mimetic by containing all or some non-natural residues in place of naturally occurring amino acid residues; non-natural residues are well described in the scientific and patent literature.

Antagonists and binding agents of the invention can also include antibodies to p30 (LIGHT), antibodies and polypeptides which bind to or act as antagonist of HVEM (as discussed more fully below) and antibodies which act as agonists of LTβR or TNFR1 (see, e.g., Examples 21 and 22), as well as the fusion proteins describe herein.

The fusion protein of the invention includes the full length HVEM polypeptide sequence as well as fragments of the sequence which may exclude certain peptides sequences. Similarly, the LIGHT (p30) polypeptide of the invention includes the full length p30, homotrimer forms, fusion proteins comprising p30 sequence, as well as fragments of the sequence which may exclude certain amino acids, peptides or sequences, and homo- or hetero-trimeric forms of these fragments, such as, e.g., LIGHT-t66, as described below. Such fragments can be useful in the creation of the antibodies of the invention, including polyclonal and monoclonal antibodies.

For example, such excluded sequences may include fragments lacking the carboxyl terminal region of the full length HVEM polypeptide. In addition, the fusion polypeptides of the invention can include an HVEM polypeptide sequence or a fragment thereof.

The "second" polypeptide sequence of the fusion protein can be any polypeptide desired to be linked to a polypeptide sequence of the invention (e.g., p30 or HVEM sequence) so long as the p30/HVEM:second polypeptide fusion protein retains a binding (e.g., virus blocking or receptor binding) or biological activity that is substantially similar to the binding (e.g., to receptors) or biological activity of a p30:Fc or HVEM:Fc (e.g., inhibits or modulates inflammation). The identification and determination of second polypeptide sequences useful in the present invention are readily identifiable to one skilled in the art. For example, one skilled in the art can determine whether a fusion construct retains the desired receptor binding or biological activity by using the methods and techniques described in Examples below.

The invention also provides isolated nucleic acid sequences or polynucleotides encoding the polypeptide of the invention. Nucleic acids encoding any of the above polypeptides, fragments, modifications and fusion proteins are also encompassed by the present invention. Thus, the term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode antagonists, binding agents or a fusion polypeptide of the invention. For example, it is understood that all polynucleotides encoding all or a portion of LIGHT or HVEM or fusion polypeptides thereof are also included herein, so long as they encode a polypeptide with LIGHT:Fc or HVEM:Fc activity, as described herein. Such polynucleotides include (isolated) naturally occurring, recombinant, synthetic, and intentionally manipulated polynucleotides. For example, portions of the mRNA sequence may be altered due to alternate RNA splicing patterns or the use of alternate promoters for RNA transcription. As another example, the polynucleotide may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention so long as the amino acid sequence of LIGHT or HVEM and (in the case of a fusion protein) a second polypeptide encoded by the nucleotide sequence are functionally unchanged.

The nucleic acids of the invention comprise sequences that encode an polypeptide of the invention, an antagonist, a binding agent or a fusion protein (e.g., LIGHT-FLAG or HVEM:Fc), as well as fragments of naturally occurring LIGHT or HVEM and any nucleotide sequence that can hybridize to the complement of these sequences under stringent conditions. The invention also includes degenerate variants of these sequences for both p30 and the fusion polypeptides of the invention. For example, the LIGHT p30 nucleic acids of the invention include sequences that encode naturally occurring p30 and any nucleotide sequences that hybridize to the complement of the sequences under stringent conditions as described herein.

The phrase "stringent conditions" refers to hybridization or wash conditions under which a nucleic acid, e.g., a sample nucleic acid or a probe will primarily hybridize to its target subsequence, typically in a complex mixture of nucleic acid, but to no other sequences in significant amounts. A positive signal (e.g., identification of a nucleic acid of the invention) is about 10 times background hybridization. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point (Tm) for the specific sequence at a defined ionic strength and pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium).

Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Stringent hybridization conditions that can be used to identify nucleic acids within the scope of the invention can include hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1%

SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be used to identify and isolate nucleic acids within the scope of the invention. Those of ordinary skill will readily recognize that alternative but comparable hybridization and wash conditions can be utilized to provide conditions of similar stringency.

However, the selection of a hybridization format is not critical, as is known in the art, it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14_base oligos), 48° C. (for 17-base oligos), 55° C. (for 20-base oligos), and 60° C. (for 23-base oligos). See Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997), or Tijssen (1993) supra, for detailed descriptions of equivalent hybridization and wash conditions and for reagents and buffers, e.g., SSC buffers and equivalent reagents and conditions.

These nucleic acid molecules may encode or act as p30 antisense molecules, useful, for example, in p30 regulation (for and/or as antisense primers in amplification reactions of p30 nucleic acid sequences). Still further, such molecules may be used as components of screening methods whereby, for example, the presence of a p30 gene may be detected.

In addition to the nucleotide sequences described above, full length cDNA or genomic sequences can be identified and readily isolated, without undue experimentation, by molecular biological techniques well known in the art. The invention encompasses these nucleic acid molecules.

DNA sequences of the invention can be obtained by several methods. For example, the DNA can be isolated using hybridization or computer-based techniques which are well known in the art. These include, but are not limited to: (a) hybridization of genomic or cDNA libraries with probes to detect homologous nucleotide sequences; (b) antibody screening of expression libraries to detect cloned DNA fragments with shared structural features; (c) polymerase chain reaction (PCR) on genomic DNA or cDNA using primers capable of annealing to the DNA sequence of interest; (d) computer searches of sequence databases for similar sequences; (e) differential screening of a subtracted DNA library; and (f) large scale genomic sequencing by expressed sequence tags (EST) of a T cell cDNA library. Preferably the polynucleotides (e.g., p30 polynucleotide and HVEM:fusion protein polynucleotide) of the invention are derived from a mammalian organism.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace et al. (1981) Nucl. Acid Res. 9:879). Alternatively, a subtractive library, is useful for elimination of non-specific cDNA clones.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., (1983) Nucl. Acid Res. 11:2325). Appropriate oligonucleotide probes and primers can be constructed by "back-translating" the amino acid sequence of the p30 polypeptide obtained by N-terminal amino acid sequencing. A cDNA expression library, such as lambda gt11, can be screened indirectly for p30 peptides having at least one epitope, using antibodies specific for p30. Such antibodies can be either polyclonally or monoclonally derived and used to detect expression product indicative of the presence of p30 cDNA.

Alterations in p30 nucleic acid include intragenic mutations (e.g., point mutation, nonsense (stop), missense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Such proteins can be analyzed by standard SDS-PAGE and/or immunoprecipitation analysis and/or Western blot analysis, for example.

The invention also encompasses DNA vectors that contain any of the foregoing p30 coding sequences and/or their complements (i.e., antisense) and expression vectors that contain any of the foregoing p30 coding sequences.

The invention also encompasses DNA vectors that contain any of the foregoing fusion polypeptide coding sequences and/or their complements and expression vectors that contain any of the foregoing coding sequences. An expression vector is composed of or contains a nucleic acid in which a polynucleotide sequence encoding a peptide or polypeptide of the invention is operatively linked to a promoter or enhancer-promoter combination. A promoter is a transcriptional regulatory element composed of a region of a DNA molecule typically within 100 nucleotide pairs in front (upstream of) of the point at which transcription starts. Another transcriptional regulatory element is an enhancer. An enhancer provides specificity in terms of time, location and expression level. Unlike a promoter, an enhancer can function when located at variable distances from the transcription site, provided a promoter is present. An enhancer can also be located downstream of the transcription initiation site. A coding sequence of an expression vector is operatively linked to a transcription terminating region. To bring a coding sequence under control of a promoter, it is necessary to position the translation initiation site of the translational reading frame of the peptide or polypeptide between one and about fifty nucleotides downstream (3') of the promoter. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast α mating factors.

Expression vectors and methods for their construction are known to those familiar with the art. Suitable vectors include plasmids, and viral vectors such as herpes viruses, retroviruses, canary pox viruses, adenoviruses and adeno-associated viruses, among others.

The invention includes suitable host cell lines transfected with expression vectors containing the nucleic acid sequences described. Cells to be used for transfection include, but are not restricted to HEK293 cells of mammalian origin or Sf9 and TN5 insect cells, for example, for expression of a fusion polypeptide of the invention in its various natural or engineered forms. Cells are transfected by a variety of methods commonly used in the art, for example, electroporation or calcium phosphate precipitation. Genes can also be introduced into the cells by transduction with viral vectors, e.g., retroviruses. Successfully transfected cell lines are selected by appropriate means familiar to those of average skill in the art, e.g., using tissue culture medium supplemented with a drug such as Geneticin™ (G418) or puromycin, for example, for which the relevant expression vector contains a resistance gene. Successfully transfected cell lines are screened expression of the fusion molecules by a variety of possible methods, e.g., flow cytometry analysis.

"Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

Antibodies that specifically recognize antigenic epitopes within an amino acid sequence of p30 or HVEM or LTβR or TNFR1 are also encompassed by the invention. Such antibodies include but are not limited to non-human, humanized and fully human antibody sequences. For example, humanized and fully human antibodies having the binding specificity of a monoclonal antibody denoted 3C8, 3H4 or 4H8. Antibodies include polyclonal antibodies (IgG, IgM, IgA, IgE and IgD), monoclonal antibodies, chimeric antibodies, single chain antibodies, Fab fragments, F(ab')$_2$ fragments, Fv, and epitope-binding fragments of any of the above. The term "antibody" therefore includes intact antibody molecules as well as fragments thereof. Exemplary fragments include, for example, those capable of binding to an antigenic determinant present in p30 or HVEM or LTβR or TNFR1 or a functional subsequence thereof, and having agonist or antagonist activity. Generally, antigenic determinants have at least 3–5 contiguous amino acids.

Such antibodies can act as antagonists or binding agents in modulation an inflammatory reaction. For example, antibodies to p30 can act by interaction with p30 and preventing p30's binding to its receptor. Similarly, antibodies that bind to or interact with HVEM can also act to prevent binding of HVEM with its ligand (e.g., p30). Such antibodies can also act in modulation of viral infection. For example, antibodies that bind LTβR or TNFR1 and which have agonist activity (e.g., antibody having the binding specificity of a monoclonal antibody denoted 3C8, 3H4 or 4H8) can be used to activate LTβR or TNFR1 activity which, in turn inhibits or prevents herpesvirus (e.g., CMV) infection, reactivation from latency or disorders associated with herpesvirus (e.g., CMV) infection.

The antibodies of the invention can be used, for example, in the treatment of autoimmune diseases and lymphocytic malignancies. They can also be used to test for expression of p30 on a cell and may thus be utilized as part of a screening procedure to select an appropriate treatment for a particular subject. For example, if the tumor cells of a lymphoma or leukemia patient express p30, anti-p30 antibody or immunotoxin conjugates of anti-p30 antibody or immunotoxin conjugates of anti-p30 antibody may be used as therapy in that patient. Such antibodies may also be utilized in the screening assays of the invention. Antibodies that bind LTβR or TNFR1 and which have agonist activity can be used to treat, inhibit or prevent herpesvirus (e.g., CMV) infection.

Protein suitable for generating antibodies can be produced by any of a variety of standard synthetic or recombinant expression techniques known in the art. For example, protein can be produced by standard peptide synthesis techniques, such as solid-phase synthesis. Nucleic acid encoding protein may be expressed in a cell and the protein produced by the cells may be purified. For example, using a baculovirus expression construct and isolating the produced protein from infected Tn5 insect cells. The protein may be expressed as a part of a larger protein by recombinant methods. The protein may then be purified with a protein A column or affinity column. Alternatively, the protein may contain an amino acid sequence such as a T7 tag or polyhistidine sequence to facilitate purification of the expressed or synthesized protein.

Antibodies may be produced using intact polypeptide, functional subsequences thereof or small peptide fragments, or fusion protein as the immunizing antigen. To produce antibodies that specifically bind to the N- or C-terminal domains of a protein, or internal amino acid sequences, appropriate regions can be used as immunizing antigen.

For the production of antibodies of the invention, a host animal is immunized by injection with either the fusion polypeptide, the individual polypeptides comprising the fusion polypeptide (e.g., HVEM), with cells expressing the fusion polypeptide, or the p30 polypeptide. Alternatively, peptides corresponding to specific regions (i.e., antigenic epitopes) of these polypeptides may be used as immunogens. Such host animals may include but are not limited to rabbits, mice, and rats. Various adjuvants may be used to increase the immunological response, depending on the host species, including but not restricted to Freund's (complete and incomplete) adjuvant, mineral gels such as aluminum hydroxide, lysolecithin, pluronic polyols, polyanions, peptides, oil emulsions, BCG (bacille Calmette-Guerin) and *Corynebacterium parvum*. Polyclonal antibodies are heterogeneous populations of antibody molecules derived from the sera of the immunized animals.

In order to further enhance immunogenicity, the immunogen may be coupled to a carrier. Examples of such carriers are keyhole limpet hemocyanin (KLH) and bovine serum albumin (BSA). Other albumins such as ovalbumin, mouse serum albumin or rabbit serum albumin can also be used as carriers. Methods of coupling a peptide to a carrier are well known in the art and include the use of glutaraldehyde, carbodiimide and m-maleimidobenzoyl-N-hydroxysuccinimide ester.

The amount of antigen to be used can be determined readily by those with average skill in the art without undue experimentation. The antigen can be administered by a number of routes (e.g., subcutaneous, intramuscular, intradermal, intravenous and intraperitoneal). The production of polyclonal antibodies is monitored by sampling blood of the immunized animal at various time points after administration. When the desired level of antibody is obtained, the animal is bled and the serum is stored.

Monoclonal antibodies, which are homogeneous populations of antibodies to a particular antigen, may be obtained by any technique which provides for the production of antibody molecules by continuous cell lines in culture. These include, but are not limited to, the hybridoma technique (Kohler and Milstein (1975) Nature 256:495–497; U.S. Pat. No. 4,376,110; Howell and Lane (1988) Antibodies, A Laboratory Manual, Cold Spring Harbor Press, N.Y.), the human B-cell hybridoma technique (Kosbor (1983) Immunology Today 4:72; Cole et al. (1983) Proc. Natl. Acad. Sci. USA 80:2026), and the EBV-hybridoma technique (Cole et al. (1985), Monoclonal Antibodies And Cancer Therapy, Alan R. Liss, Inc.). Monoclonal antibodies can be isolated and purified from hybridoma cultures by a variety of well-established techniques which include, for example, affinity chromatography with Protein-A Sepharose, size-exclusion chromatography, and ion-exchange chromatography (see, e.g., Coligan et al. (1994) In: *Current Protocols in Immunology*, Wiley; and Barnes et al. (1992) In: *Methods in Molecular Biology*, Vol. 10, pages 79–104, Humana Press). Such antibodies may be of any immunoglobulin class including IgG, IgM, IgE, IgA, IgD and any subclass thereof.

In addition, techniques developed for the production of "chimeric antibodies" can be used (Morrison et al. (1984) Proc. Natl. Acad. Sci. USA 81:6851; Neuberger (1984) Nature 312:604; Takeda (1985) Nature 314:452). These involve, for example, splicing a portion of a gene encoding a mouse antibody of appropriate antigen specificity to a portion of a gene encoding a human antibody of appropriate biological activity. A chimeric antibody is a molecule in which different portions are derived from different animal species, such as those having a variable region derived from a murine monoclonal antibody and a human immunoglobulin constant region. Such chimeric antibodies could also be generated, for example, by immunizing mice containing the human genetic loci encoding IgH and κ and λ light chain loci.

Chimeric antibodies can be produced using recombinant DNA technology and expression of the recombinant construct in cells to produce the antibody chimera. Alternatively, techniques described for the production of single chain antibodies (U.S. Pat. No. 4,946,778; Bird (1988) Science 242:423; Huston et al. (1988) Proc. Natl. Acad. Sci. USA 85:5879; and Ward et al. (1989) Nature 334:544) can be adapted to produce single chain antibodies against epitopes of the fusion polypeptide of the invention. Single chain antibodies are formed by linking the heavy and light chain fragments of the Fv region via an amino acid bridge, resulting in a single chain polypeptide. They are conveniently produced by recombinant DNA techniques. The antibody may be purified as discussed herein, for example, protein A or G purification or affinity purification, or using other methods known in the art.

Antibody fragments which recognize specific epitopes may be generated by known techniques. For example, such fragments include but are not limited to the F(ab')2 fragments which can be produced by pepsin digestion of the antibody molecule, and the Fab fragments which can be generated by reducing the disulfide bridges of the $F(ab')_2$ fragments. Alternatively, Fab expression libraries may be constructed (Huse (1989) Science 246:1275) to allow rapid and easy identification of monoclonal Fab fragments with the desired specificity. Methods for screening antibodies for binding specificity are well known in the art.

Humanized antibodies can be produced by transferring non-human complementarity determining regions (CDR's) from heavy and light variable chains into a human variable domain, and then substituting human residues in the framework regions of the non-human counterparts. Techniques for producing humanized monoclonal antibodies are described, for example, by Jones et al. (1986) Nature 321:522; Riechmann et al. (1988) Nature 332:323; Verhoeyen et al. (1988) Science 239:1534; Carter et al. (1992) Proc. Natl. Acad. Sci. USA 89:4285; Sandhu (1992) Crit. Rev. Biotech. 12:437; and Singer et al. (1993) J. Immunol. 150:2844. The use of fully human and humanized antibodies obviates potential problems associated with immunogenicity of non-human sequences.

In order to produce fully human antibodies, a protein antigen can be produced using techniques known in the art and subsequently used to immunize human transchromosomic (Tc) mice, which contain kappa or lambda human IgG chains in their chromosomes (Tomizuka et al., (2000) Proc. Natl. Acad. Sci. USA 97:722 and Tomizuka et al., (1997) Nat. Genet. 16:133). Mice exhibiting positive antibody titer can be used for spleen cell fusions and monoclonal antibodies prepared using the general method of Kohler and Milstein (Nature 256:495 (1975)). The resulting hybridomas are assayed for the production of heavy or kappa chains and then for antibody production. Cells may be cloned and rescreened for antibody production. The selected or cloned hybridomas are then cultured either in vitro (e.g., in tissue culture), or in vivo (as ascites in mice) and human antibodies purified. Suitable purification techniques include affinity purification, non-denaturing gel purification, HPLC or RP-HPLC, purification on protein A column, or any combination of these techniques. The antibodies are confirmed to be human Ig by using mouse Ig-absorbed anti-human Ig in an ELISA assay.

Thus, in another embodiment, the invention provides methods of producing human antibodies that modulate activity of LTβR or TNFR1. In one embodiment, a method includes administering LTβR or TNFR1 or an immunogenic fragment thereof to an animal (e.g., a mouse) capable of expressing human immunoglobulin; screening the animal for expression of human LTβR or TNFR1 antibody; selecting an animal that produces a human LTβR or TNFR1 antibody; isolating the antibody from the animal; and determining whether the human LTβR or TNFR1 antibody modulates an activity of LTβR or TNFR1 thereby identifying a human LTβR or TNFR1 antibody that modulates an activity of LTβR or TNFR1. In yet another embodiment, a method includes administering human LTβR or TNFR1 or an immunogenic fragment thereof to an animal (e.g., a mouse) capable of expressing human immunoglobulin; isolating spleen cells from the animal that produces human LTβR or TNFR1 antibody; fusing the spleen cells with a myeloma cell to produce a hybridoma; and screening the hybridoma for expression of a human LTβR or TNFR1 antibody that modulates an activity of LTβR or TNFR1 thereby identifying a hybridoma that produces a human LTβR or TNFR1 antibody.

The invention features in vitro systems designed to identify compounds capable of modulating cellular responses mediated via either the HVEM or LTβR receptor polypeptides. "Cellular responses" refers herein to cell activation, cell internalization of HSV or changes in activation or production of inflammatory mediators such as inflammatory cells, cytokines, prostaglandins and leukotrienes. These cellular responses are elicited by an interaction of (a) HVEM with p30, gD or LTα; or (b) LTβR with p30.

The term "ligand" refers to a polypeptide or a compound that binds to a receptor protein in a high affinity and specific manner to elicit a functional response. For example ligands of the invention include p30, gD or LTα. The term "receptor" refers herein to a polypeptide which, when bound by a ligand, induces a cellular response. Receptors of the invention include HVEM or LTβR or TNFR1. The term "binding agent" refers to a polypeptide or a compound that binds to a receptor or a ligand in a high affinity and specific manner and may or may not elicit a functional response.

In one embodiment the invention features an assay for identifying a compound which affects an HVEM-binding agent-mediated cellular response. This assay involves: (a) incubating the compound with an HVEM polypeptide or a cell expressing an HVEM polypeptide, and an HVEM-binding agent, under conditions which allow the components to interact; and (b) determining the effect of the compound on the HVEM-binding agent-mediated cellular response. Also within the invention is an assay for identifying a compound which affects an LTβR-p30-mediated cellular response. This assay involves: a) incubating the compound with an LTβR polypeptide or a cell expressing an LTβR polypeptide, and with p30, under conditions which allow the components to interact; and (b) determining the effect of the compound on the LTβR-p30-mediated cellular response. In the assays of the invention compounds are screened for their ability to either modulate a cell activation mediated by interaction HVEM or LTβR with a ligand or to inhibit infection of susceptible cells by HSV.

In another embodiment the invention features an assay for identifying a compound that inhibits herpesvirus (e.g., CMV) infection. This assay involves: (a) contacting LTβR or TNFR1 with a test compound under conditions allowing binding; (b) measuring LTβR or TNFR1 activity in the presence of the test compound; and (c) comparing activity in the presence of the test compound to the absence of the test compound. An increase in LTβR or TNFR1 activity in the presence of the test compound identifies the test compound as a compound that inhibits herpesvirus (e.g., CMV) infection. The identified compound may further be tested for inhibiting herpesvirus (e.g., CMV) infection in cells or in vivo (e.g., in animals).

In yet another embodiment the invention features an assay for identifying a compound that inhibits herpesvirus (e.g., CMV) infection. This assay involves: (a) contacting a cell that expresses LTβR or TNFR1 in the presence of herpesvirus (e.g., CMV) with a test compound under conditions allowing binding between LTβR or TNFR1 and the test compound; (b) measuring herpesvirus (e.g., CMV) proliferation, replication, protein expression or cytopathicity in the presence of the test compound; and (c) comparing herpesvirus (e.g., CMV) proliferation, replication, protein expression or cytopathicity in the presence of the test compound to the absence of the test compound. A decrease in herpesvirus (e.g., CMV) proliferation, replication, protein expression or cytopathicity in the presence of the test compound identifies the test compound as a compound that inhibits herpesvirus (e.g., CMV) infection.

The invention features cellular response assays. These cellular response assays measure either protein activity, changes in gene expression (e.g., nuclear factor κB(NFκB) responsive genes such as intercellular adhesion molecule-1 (ICAM1) and vascular adhesion molecule 1 (VCAM1) and chemokines such as interleukin-8 and secondary lymphoid organ chemokine), cell activation, cell infection by herpesvirus or modulation of inflammation via affecting inflammatory mediators such as inflammatory cell recruitment, activation, and production of pro-inflammatory cytokines (e.g., interleukins (IL) and interferons (IFN), prostaglandins and leukotrienes.

Test compounds can be tested for their ability to modulate a response of cells expressing receptors (e.g., HVEM or LTβR or TNFR1) stimulated by ligands (e.g., p30, LTα or gD) and a suboptimal dose of a stimulus appropriate for the cells. The "responder" receptor expressing cells can be freshly obtained from a subject or they can be a cultured cell line. The cells can express endogenously encoded receptor or a receptor encoded by a transfected gene. The ligand may be added to the cellular response cultures in the form of an isolated polypeptide or by addition to the cultures of cells expressing the ligands. The ligand expressing cells may express an endogenous gene encoding the ligand or may express a transfected gene encoding the ligand. Furthermore the ligand may be expressed on the cell surface (p30 or gD) or be may be secreted (p30, gD or LTα). In order for p30 or gD to be secreted, the gene encoding it would need to have the region encoding the transmembrane domain deleted. Cellular activation can be measured by, for example, cell proliferation, de novo expression of cell-surface activation markers, or soluble factor production.

In a preferred embodiment, the cells are lymphocytes. In the case of T cells, the receptor (HVEM) expressing responder T cells can be cultured in the presence of the test compound, the ligand and a suboptimal dose of a T cell activator, e.g., anti-CD3 antibody, a lectin such as phytohemoglutinin (PHA) or a superantigen such as staphylococcal enterotoxin C (SEC). Controls will be cultures containing: (a) T cells alone; (b) T cells with T cell activator, with ligand and without test compound; (c) T cells with T cell activator, without ligand and without test compound; (d) T cells with T cell activator, without ligand and with test compound, (e) T cells without T cell activator, with ligand and without test compound; (f) T cells without T cell activator, without ligand and without test compound and (g) T cells without T cell activator, without ligand and with test compound. T-cell activation can be measured in terms of T cell proliferation by incorporation of $^3$H-thymidine (see Example 5), induction of activation markers such as CD69 or CD25, or production of cytokines such as interleukin-2 (IL-2), interleukin-4 (IL-4) or interferon-γ (IFNγ).

In the case of B lymphocytes similar response assays can be carried out. The B cell activators may be mitogens such as poke weed mitogen, staphylococcal protein A or anti-immunoglobulin. Cell activation cell can be measured by cell proliferation (again by $^3$H-thymidine incorporation) or Ig secretion. Alternatively, the survival of B cells in nutritionally suboptimal medium may be measured (see Example 5).

The ability of a test compound to inhibit lymphocyte activation would be an indication that such a compound may be useful in the treatment of an autoimmune disease largely involving T-cells (rheumatoid arthritis, insulin dependent diabetes mellitus and multiple sclerosis, for example) or T and B cells (systemic lupus erythematosus and myasthenia gravis, for example) as well as inflammatory disorders, for example, arthritis, psoriasis, and inflammatory bowel disease. The ability of a test compound to stimulate lymphocyte activation would be an indication that such a compound may be useful in stimulating immune responses in subjects with infectious diseases, or in which the subject is immunosuppressed as, for example, in patients undergoing chemotherapy or radiation therapy for cancer or in patients with AIDS.

In assays for test compounds that prevent herpesvirus infection, the test compounds can be added to cultures of herpesvirus susceptible cells and herpesvirus. Permissive cell lines for virus infection include human dermal fibroblasts, peripheral blood lymphocytes treated with agents that cause activation (e.g., anti-CD3 antibody, or phytohemagglutinin), and transformed cell lines (e.g., Hela cells). Virus production can be measured by any number of methods known by those skilled in the art including viral plaque assays, production of specific virus proteins measured by an ELISA or use of recombinant virus that contains an indicator gene product like β-galactosidase, an enzyme easily detectable by colorimetric assays (Montgomery (1996) supra).

The ability of a test compound to inhibit cell infection by HSV would be an indication that such a compound may be useful in the treatment of a subject with an HSV infection. In order to test whether compounds which affect cellular responses function by binding either member of the relevant receptor-ligand pair, they can be tested for their ability to bind to soluble forms of the receptor or ligand by assays well known in the art, for example, ELISAs, Western blotting or radioimmunoassays. Furthermore, to test whether binding of a test compound to either the receptor or the ligand results in inhibition of their binding to each other, the test compound can be tested for its capacity to inhibit binding of soluble forms of the receptor and the ligand. Examples of these assays are competitive ELISAs, competitive Western blotting and competitive radioimmunoassays.

Test compounds include purified and unpurified compounds, e.g. extracts from living organisms. Natural compounds in the form of bacterial, fungal, plant and animal cell or tissue extracts are available or can be readily produced. Generally test compounds will be found among biomolecules including, but not limited to: polypeptides, peptidomimetics, saccharides, fatty acids, steroids, purines, pyrimidines, derivatives, structural analogs or combinations thereof. Test compounds further include chemical compounds (e.g., small organic molecules having a molecular weight of more than 50 and less than 5,000 Daltons, such as hormones). Candidate organic test compounds comprise functional groups for interaction with proteins, particularly hydrogen bonding, and typically include at least an amine, carbonyl, hydroxyl or carboxyl group, preferably at least two of the functional chemical groups. Candidate organic compounds often comprise cyclical carbon or heterocyclic structures and/or aromatic or polyaromatic structures substituted with one or more of the above functional groups. Known pharmacological agents are considered test compounds and may further include agents subjected to directed or random chemical modifications, such as acylation, alkylation, esterification, amidification, etc., to produce structural analogs, for example.

Test compounds include libraries of compounds, for example, synthetic or natural compounds in a combinatorial library such as peptides (e.g., antibodies, or other peptides having common functional or structural features, such as nucleic acid binding, intracellular signaling, binding activity, etc.), and small organic molecules, such as drugs. Numerous libraries are commercially available or can be readily produced; means for random and directed synthesis of a wide variety of organic compounds and biomolecules, including expression of randomized oligonucleotides and oligopeptides, are known. Additionally, natural or synthetically produced libraries and compounds are readily modified through conventional chemical, physical and biochemical means, and may be used to produce combinatorial libraries. Such libraries are useful for the screening of a large number of different test compounds. Moreover, such test compounds additionally can be modified so as to facilitate their identification or purification. Such modifications are well known to the skilled artisan (e.g., biotin and streptavidin conjugated compounds, polyhistidine and T7 tags). The test compounds may therefore be a defined, isolated and purified candidate compound (e.g., a synthetic small molecule), a member of a combinatorial library or may be present in a biological sample such as a biological fluid, tissue extract, subcellular fraction or cellular lysate.

Peptides and polypeptides used in the screening assays of the invention may be obtained by a variety of means. Smaller peptides (less than 50 amino acids long) may be conveniently synthesized by standard chemical methods. Some polypeptides (e.g. antibodies) may be purchased from commercial sources. Where otherwise unavailable, antibodies can be generated as described supra. Detectably labeled antibodies either can be purchased from commercial sources or are readily prepared by those of ordinary skill in the art.

Polypeptides such as HVEM, LTβR, p30 (LIGHT), gD or LTα may be purified from biological sources by methods well-known to those skilled in the art (Protein Purification, Principles and Practice, second edition (1987) Scopes, Springer Verlag, N.Y.). They may also be produced in their naturally occurring, truncated, fusion or chimeric protein forms by recombinant DNA technology using techniques well known in the art. These methods include, for example, in vitro recombinant DNA techniques, synthetic techniques, and in vivo genetic recombination. See, for example, the techniques described in Sambrook et al. (1989) Molecular Cloning, A Laboratory Manual, Cold Spring Harbor Press, N.Y.; and Ausubel et al., cited supra. Alternatively, RNA encoding the proteins may be chemically synthesized. See, for example, the techniques described in Oligonucleotide Synthesis, (1984) Gait, M. J. ed., IRL Press, Oxford, which is incorporated by reference herein in its entirety.

A variety of host-expression vector systems may be utilized to express the nucleotide sequences. Where the peptide or polypeptide is soluble, it can be recovered from: (a) the culture, i.e., from the host cell in cases where the peptide or polypeptide is not secreted or (b) from the culture medium in cases where the peptide or polypeptide is secreted by the cells. The expression systems also encompass engineered host cells that express the polypeptide in situ, e.g., anchored in the cell membrane. Purification or enrichment of the polypeptide from such an expression system can be accomplished using appropriate detergents, lipid micelles and other methods well known to those skilled in the art. Alternatively, such engineered host cells themselves may be used in situations where it is important not only to retain the structural and functional characteristics of the protein, but also to assess biological activity.

The expression systems that may be used for purposes of the invention include but are not limited to microorganisms such as bacteria (for example, E. coli and B. subtilis) transformed with recombinant bacteriophage DNA, plasmid DNA or cosmid DNA expression vectors containing the nucleotide sequences; yeast transformed with recombinant yeast expression vectors; insect cells infected with recombinant viral expression vectors (baculovirus); plant cell systems infected with recombinant viral expression vectors (e.g., cauliflower mosaic virus, CaMV; tobacco mosaic virus, TMV) or transformed with recombinant plasmid expression vectors; or mammalian cells (e.g., COS, CHO, BHK, 293, 3T3) harboring recombinant expression constructs containing promoters derived from the genome of mammalian cells (e.g. metallothionein promoter) or from mammalian viruses.

In bacterial systems, a number of expression vectors may be advantageously selected depending upon the use intended for the gene product being expressed. For example, when a large quantity of such a protein is to be produced, e.g. for raising antibodies to the protein, vectors which direct the expression of high levels of fusion protein products that are readily purified may be desirable. Such vectors include, but are not limited to, the E. coli expression vector pUR278 (Ruther et al. (1983) EMBO J. 2:1791), in which the coding sequence may be ligated individually into the vector in frame with the lacZ coding region so that a fusion protein is produced; pIN vectors (Inouye (1985) Nucleic Acids Res. 13:3101; Van Heeke (1989) J. Biol. Chem. 264:5503); and the like. pGEX vectors may also be used to express foreign polypeptides as fusion proteins with glutathione S transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. It is understood that the polypeptides used for the screening assays can be either the naturally occurring forms of the polypeptides or fusion proteins containing the polypeptides. The irrelevant part of the fusion protein can be, for example, the Fc portion of immunoglobulin G, hexahistidine or GST.

In mammalian host cells, a number of viral-based expression systems may be utilized. In cases where an adenovirus is used as an expression vector, the nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (e.g., See Logan & Shenk (1984) Proc. Natl. Acad. Sci. USA 81:3655). Specific initiation signals may also be required for efficient translation of inserted nucleotide sequences. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (Bittner (1987) Methods in Enzymol. 153: 516).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Appropriate cell lines or host systems can be chosen to ensure the correct modification and processing of the foreign protein expressed. Mammalian host cells include but are not limited to CHO, VERO, BHK, Held, COS, MDCK, 293, 3T3, and WI38.

For long-term, high-yield production of recombinant proteins, stable expression is preferred. For example, cell lines which stably express the sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1 to 2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the gene product. Such engineered cell lines may be particularly useful in screening and evaluation of compounds that affect the endogenous activity of the gene product.

A fusion protein may be readily purified by utilizing an antibody or a moiety that specifically binds to the fusion protein being expressed. For example, a system described by Janknecht (1991) Proc. Natl. Acad. Sci. USA 88:8972, allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers. If desired, the histidine tag can be selectively cleaved with an appropriate enzyme.

Chimeric proteins may also be derived by methods known to those in the art. These involve splicing a portion of a gene encoding a given protein to one or more portions derived from one or more genes encoding different proteins. A chimeric polypeptide is a molecule in which different portions are derived from different proteins. For example, a chimeric protein may contain a domain of HVEM and another domain of LTβR or a domain of HVEM and a domain of an Fc region of an antibody.

The invention provides methods for modulating an HVEM-mediated cellular response by contacting a cell expressing the receptor polypeptide, HVEM, with an HVEM binding agent. Alternatively, an HVEM-mediated cellular response is modulated by contacting a ligand for HVEM with a ligand binding agent. Such ligands include LIGHT (p30), LTα or gD. LIGHT (p30) can be expressed on the surface of a cell or it can be soluble, e.g., in homotrimeric form. LTα can be secreted and gD can be expressed on an HSV virion or on the surface of an HSV-infected cell.

The phrase "cellular responses" refers again herein to cell activation (e.g., an increase in production or inflammatory mediators) or to internalization of HSV by the cell. The invention also features methods for modulating LTβR-mediated cellular responses by contacting a cell expressing LTβR or a cell expressing the LTβR ligand, p30, with a binding agent that binds either to HVEM or the p30.

As used herein, the term "contacting" means exposing the receptor or the ligand to the binding agent, in a receptor-modulating effective amount, so that the binding agent can effectively modulate the cellular response initiated by interaction of the ligand with the receptor. Modulation can result in inhibition or activation of the cellular response. These alternative properties of a particular binding agent for a particular receptor-ligand pair can be tested for in advance using the screening assays described (see, e.g., Examples 6–8).

With respect to receptor binding agents, HVEM binding agents include soluble gD, soluble p30 (e.g. LIGHT-t66) or a peptide fragment of LTα, preferably a peptide fragment that contains the amino acid Tyr at a position corresponding to position 108 from the N-terminus of naturally occurring LTα. An LTβR binding agent is soluble p30.

With respect to ligand binding agents, p30 binding agents include soluble HVEM, soluble LTβR, chimeric constructs (e.g., fusion proteins) such as for example, HVEM:Fc or antibody that binds specifically to p30. An LTα binding agent is soluble HVEM, for example, an HVEM:Fc fusion protein or chimeric construct.

Contacting may be in vitro, for example, by adding a binding agent or antagonist to a culture of cells expressing HVEM or LTβR, e.g., lymphocytes, undergoing activation by HVEM ligands (p30, LTα or gD) or the LTβR ligand, p30. Binding agents may also be added, for example, to a culture of HVEM expressing cells exposed to gD on the surface of HSV virions or on the surface of HSV infected cells. The ability of the binding agent to modulate these cellular responses could be tested for in advance using the screening methods described. The binding agent may be added as an isolated polypeptide or as cells transfected with an expressing vector containing a binding agent encoding nucleic acid molecule. In these in vitro methods, a "receptor-modulating effective amount" of binding agent, is the amount required to modulate cell activation or HSV infection by greater than 20%, preferably greater than 50%, more preferably greater than 80% and most preferably greater than 95%.

Contacting maybe in vivo in a subject. The subject may be a mammal, preferably a human, with an autoimmune disease such as rheumatoid arthritis, insulin dependent diabetes mellitus, multiple sclerosis, systemic lupus erythematosus or myasthenia gravis, a lymphoid (T or B cell) malignancy, an HSV infection, an infection with an organism other than HSV, an inflammatory disorder, or for immunosuppression. Inhibition of a HVEM-p30 or a LTβR-p30 mediated cellular response could be advantageous in patients with autoimmune diseases or lymphoid malignancies in that it could prevent T cell proliferation or activation (as in rheumatoid arthritis, insulin dependent diabetes mellitus, multiple sclerosis, systemic lupus erythematosus, myasthenia gravis and T cell malignancies) and B cell proliferation (as in systemic lupus erythematosus, myasthenia gravis and B cell malignancies). Inhibition of an HVEM-gD mediated cellular response (i.e., HSV internalization) could be therapeutic for subjects with an HSV infection in that it would prevent viral spread mediated by internalization of gd-expressing HSV virions present in the extracellular space or from HSV-infected cells expressing gD on their surface. Stimulation of an HVEM-p30 or a LTβR-p30 mediated cellular response would be useful in treating subjects with an infection other than HSV or immunosuppressed subjects (e.g., patients undergoing radiation and/or chemotherapy for cancer, other than lymphoid malignancies) or AIDS patients in that both T and B cell proliferation would be stimulated. Naturally, one would avoid using binding agents that stimulate an HVEM-p30 mediated cellular response in a subject with an HSV infection in that such an agent might also enhance an HVEM-gD cellular response and, thereby, the spread of HSV virus. However, this activity in the relevant binding agent could be tested for in advance using the screening assays described supra. Similarly, these stimulatory binding agents would not be used in lymphoid malignancies as they could promote growth of the tumor cells.

The binding agents to be used for in vivo modulation of cellular responses include the naturally occurring forms of HVEM, LTβR, p30, antibodies, gD and LTα as well as engineered forms such as HVEM:Fc constructs. These will be produced by the methods described supra. Peptides derived from LTα and which modulate the HVEM-LTα interaction will also be used. The peptides will contain about 205 amino acids or less. For example, they may contain five, eight, twelve, fifteen or eighteen amino acids. The peptides will preferably contain the residue Tyr, or a conservative replacement thereof, at a position corresponding to amino acid residue 108 from the N-terminus of naturally occurring LTα.

Also included as binding agents are peptidomimetics of the peptides described supra. Peptidomimetic compounds are synthetic compounds having a three-dimensional structure (i.e. a "peptide motif") based upon the three-dimensional structure of a selected peptide. The peptide motif provides the peptidomimetic compound with the activity of modulating cellular responses that is the same or greater than the activity of the peptide from which the peptidomimetic was derived. Peptidomimetic compounds can have additional characteristics that enhance their therapeutic application such as greater affinity and/or avidity and prolonged biological half-life. The peptidomimetics of the invention typically have a backbone that is partially or completely non-peptide, but with side groups identical to the side groups of the amino acid residues that occur in the peptide on which the peptidomimetic is based. Several types of chemical bonds, e.g. ester, thioester, thioamide, retroamide, reduced carbonyl, dimethylene and ketomethylene bonds, are known in the art to be generally useful substitutes for peptide bonds in the construction of protease-resistant peptidomimetics.

Polypeptide and peptide binding agents may be modified by the addition at either or both the amino- and carboxyl-terminal ends, of a blocking agent in order to facilitate survival of the relevant polypeptide or peptide in vivo. This can be useful in those situations in which the peptide termini tend to be degraded ("nibbled") by proteases. Such blocking agents can include, without limitation, additional related or unrelated peptide sequences that can be attached to the amino and/or carboxyl terminal residues of the polypeptide or peptide to be administered. This can be done either chemically during the synthesis of the peptide or polypeptide or by recombinant DNA technology. Alternatively, blocking agents such as pyroglutamic acid or other molecules known to those of average skill in the art may be attached to the amino and/or carboxyl terminal residues, or the amino group at the amino terminus or carboxyl group at the carboxyl terminus replaced with a different moiety. Likewise, the binding agents can be covalently or noncovalently coupled to pharmaceutically acceptable "carrier" proteins prior to administration.

In vivo delivery involves administering to a subject either the binding agent itself, a nucleic acid encoding the binding agent, an expression vector encoding the binding agent, or cells transfected or transduced with the vector. Expression systems therefore further include vectors specifically designed for in vivo or ex vivo applications including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979) and retroviral vectors (U.S. Pat. Nos. 5,624,820, 5,693,508 and 5,674,703 and WIPO publications WO92/05266 and WO92/14829). Bovine papilloma virus (BPV) and CMV based vectors have also been employed for in vivo uses (U.S. Pat. No. 5,719,054 and 5,561,063).

Binding agents may be delivered to a cell of a mammal using techniques substantially the same as those described infra for delivery to human subjects. Examples of appropriate mammals include but are not restricted to humans, non-human primates, horses, cattle, sheep, dogs, cats, mice, rats, guinea pigs, hamsters, rabbits and goats.

A binding agent may be delivered to cells of a patient in its unmodified state, dissolved in an appropriate physiological solution, e.g. physiological saline. Naturally, it is desirable that these peptides be selectively targeted to relevant tissues and cell types. This can be achieved by contacting the peptides directly with the affected organ or tissue, e.g., by localized injection or implantation. Thus, in autoimmune diseases such as rheumatoid arthritis or insulin-dependent diabetes mellitus, the peptides could be introduced directly into affected joints or the pancreas, respectively, or, preferably, into draining lymphoid tissue in which the active autoimmune response occurs.

Alternatively, the binding agents may be delivered in liposomes into which have been incorporated ligands for receptors on relevant cells (e.g., T cells or B cells) or antibodies to cell-surface markers expressed by these cells. Thus an antibody specific for the CD4 T cell surface marker may direct liposomes containing both the anti-CD4 antibody and the relevant binding agent to a $CD4^+$ T cell. This approach could be used in both autoimmune diseases and HSV infection. In autoimmune diseases in which the T cell receptor (TCR) expressed by a dominant pathogenic T-cell clone has been defined, an antibody specific for the relevant TCR component (e.g. Vβ) may be used. The latter methodology would represent an ideal form of immunotherapy in which pathogenic effector cells are specifically targeted for inhibition while the immune system as a whole and the cells of the target organ remain uncompromised.

In lymphoma or leukemia patients, anti-proliferative binding agents are preferably directed to cancer cells. The peptides could, for example, be injected directly into the tissues surrounding the lymphoma tumor site after surgery to remove the tumor, in order to inhibit growth of residual tumor cells. Instead of surgery, the tumor could be treated by in situ injection of the binding agent into the tumor. The liposome methodology described supra, could also be exploited. In this case antibodies specific for tumor-specific antigens (TSA) or tumor-associated antigens (TAA) would be exploited.

It is well known in the medical arts that dosages for any one patient depend on many factors, as well as the particular compound to be administered, the time and route of administration and other drugs being administered concurrently. Dosages for the binding agents of the invention will vary, but can be, when administered intravenously, approximately 0.01 mg to 10 mg/ml blood volume. Routes and doses of administration are well known to skilled pharmacologists and physicians. Routes, in addition to those described supra, include, but are not restricted to: intraperitoneal, intramuscular, intrapulmonary, transmucosal, subcutaneous and intravenous.

An in vivo gene therapy approach requires delivery of a genetic construct directly into the patient, preferably targeting it to the cells or tissue of interest. Targeting of tumor cells or activated lymphocytes, for example, can be accomplished by the use of a retrovirus, which stably transfects primarily proliferating cells. In another embodiment, the inflammatory disorder may be arthritis, and the tissue target the cartilage in the joint of a subject. In such an instance the fusion construct of the invention may be attached to a gene activated matrix (i.e., coated on a polymer material) so as to provide a slow release material or injected directly into the joint.

Tissue specific targeting may also be achieved by the use of a molecular conjugate composed of a plasmid or other vector attached to poly-L-lysine by electrostatic or covalent forces. Poly-L-lysine binds to a ligand that can bind to a receptor on tumor cells (Cristiano (1995) J. Mol. Med 73:479). Similarly, tumor and cell specific antibodies of the type described supra can be bound to vectors and thereby target them to lymphoid tumors or cells such as T-lymphocytes. The latter would be useful in autoimmune diseases and HSV infection. A promoter inducing relatively tumor-specific expression can be used to achieve a further level of targeting. Tissue-specific promoters for use in autoimmune or transplant patients include, for example, the inducible IL-2 (Thompson (1992) Mol. Cell. Biol. 12:1043), IL-4 (Todd (1993) J. Exp. Med. 177:1663) and gamma-interferon (Penix (1993) J. Exp. Med. 178:483) T-cell targeting promoters. Such inducible promoters would have an invaluable additional advantage in that expression would occur selectively in activated T-cells. Included in this population of activated T-cells are the effector cells that an ideal immunotherapeutic modality would selectively inhibit in autoimmune patients.

Vectors can also be delivered by incorporation into liposomes or other delivery vehicles either alone or co-incorporated with cell specific antibodies, as described supra.

Where the relevant binding agent is normally bound to the cell membrane (HVEM, LTβR, p30 or gD), the region of the nucleic acid encoding the transmembrane domain of binding agent will be deleted from the nucleic acid contained in the expression vector.

DNA or transfected cells may be administered in a pharmaceutically acceptable carrier. Pharmaceutically acceptable carriers are biologically compatible vehicles which are suitable for administration to a human, e.g., physiological saline. A therapeutically effective amount is an amount of the DNA of the invention which is capable of producing a medically desirable result in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is from approximately $10^6$ to $10^{12}$ copies of the DNA molecule. This dose can be repeatedly administered, as needed.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutical compositions comprising pharmaceutically acceptable carriers including invention compositions useful in practicing the methods of the invention are provided. Exemplary compositions include, for example, suppositories, pills, capsules, syrups, elixirs, drops, creams, ointments, lotions, salves, sprays, and other formulations known by those of skill in the art. Additional formulations include, for example, polymeric substances, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. Microcapsules prepared by coacervation techniques or by interfacial polymerization, for example, by the use of hydroxymethylcellulose or gelatin-microcapsules, or poly (methylmethacrolate) microcapsules, respectively, or in a colloid drug delivery system can be used for delivery of invention compositions and useful in practicing the methods of the invention. Colloidal dispersion systems include macromolecule complexes, nano-capsules, microspheres, beads, and lipid-based systems, including oil-in-water emulsions, micelles, mixed micelles, and liposomes.

The use of liposomes for introducing various compositions into cells, including protein and nucleic acid, is known to those skilled in the art (see, e.g., U.S. Pat. Nos. 4,844,904, 5,000,959, 4,863,740, and 4,975,282). Piperazine based amphilic cationic lipids useful for gene therapy also are known (see, e.g., U.S. Pat. No. 5,861,397). Cationic lipid systems also are known (see, e.g., U.S. Pat. No. 5,459,127).

Pharmaceutical formulations include carriers compatible with particular routes of administration. Solutions or suspensions used for parenteral, intradermal, or subcutaneous administration can include: water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, sodium chloride can be included in the composition. Including an agent which delays absorption, for example, aluminum monostearate and gelatin can prolong absorption of injectable compositions.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or aerosols, inhalation devices (e.g., aspirators) or suppositories. For transdermal administration, compositions may be formulated into ointments, salves, gels, or creams as generally known in the art.

Carriers that protect against rapid elimination from the body, such as a controlled release formulation or a time delay material such as glyceryl monostearate or glyceryl stearate may be used. The compositions can also be delivered using implants or microencapsulated delivery systems to achieve local or systemic sustained delivery or controlled release.

Biodegradable, biocompatible polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Alza Corporation and Nova Pharmaceuticals, Inc.

Additional pharmaceutical formulations appropriate for the compositions for administration in the methods of the invention are known in the art (see, e.g., *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; and *Pharmaceutical Principles of Solid Dosage Forms*, Technonic Publishing Co., Inc., Lancaster, Pa., (1993)).

The optimal concentration of the peptide, antibodies, fusion proteins, agonists, antagonists, nucleic acids or a derivative thereof in a pharmaceutically acceptable composition may vary, depending on a number of factors, including the preferred dosage of the compound to be administered, the chemical characteristics of the compounds employed, the formulation of the compound excipients and the route of administration. The optimal dosage of a pharmaceutical composition to be administered may also depend on such variables as the type and extent of, for example, an inflammatory disorder, or disease to be treated, the overall health status of the particular subject, the relative biological efficacy of the compound selected, the clinical endpoint desired, previous or simultaneous treatments, the general health, age, sex or race of the subject and other factors. For example, the compositions of the invention may be used for the treatment of inflammatory disorders including, but not limited to, arthritis, psoriasis, and inflammatory bowel disease. An "effective amount" or "inflammation inhibiting amount" means that amount of the compound necessary to modulate, inhibit, or suppress inflammatory responses or symptoms. In the methods of the invention, including prophylactic and treatment methods, dosages and protocols may be tailored or modified based on pharmacogenomic data. The skilled artisan will appreciate the factors that may influence the dosage and timing required to provide an amount sufficient for therapeutic benefit.

One of one of ordinary skill in the art can use the following teachings describing the methods and techniques for determining clinical dosages (Spilker B., *Guide to Clinical Studies and Developing Protocols*, Raven Press Books, Ltd., New York, 1984, pp. 7–13, 54–60; Spilker B., *Guide to Clinical Trials*, Raven Press, Ltd., New York, 1991, pp. 93–101; Craig C., and R. Stitzel, eds., *Modern Pharmacology*, 2d ed., Little, Brown and Co., Boston, 1986, pp. 127–33; T. Speight, ed., *Avery's Drug Treatment: Principles and Practice of Clinical Pharmacology and Therapeutics*, 3d ed., Williams and Wilkins, Baltimore, 1987, pp. 50–56; R. Tallarida, R. Raffa and P. McGonigle, *Principles in General Pharmacology*, Springer-Verlag, New York, 1988, pp. 18–20) to determine the appropriate dosage to use.

Combination compositions and treatment methods using the combinations and treatments in the methods of the invention are also included. For example, compositions described herein can be combined with compositions known in the art that improve or lessen side effects of treatment or in order to treat a p30 polypeptide mediated cellular response, or a herpesvirus (e.g. CMV) infection. Thus, for treatment of inflammation or risk of inflammation, for example, a steroid (e.g., dexamethasone, triamcinalone, prednisone, cortisone, hydrocortisone) or a non-steroid anti-inflammatory drug (e.g., aspirin) may be used in combination with an invention composition. For treatment of a tumor, for example, an antitumor drug or treatment (e.g., methotrexate, tamoxifen, 5-Fu, radiotherapy, surgical resection) may be used in combination with an invention composition. For a herpesvirus (e.g., CMV) infection, an antiviral agent, for example, inhibitor of virus fusion to a cell or entry into a cell, viral RNA or DNA replication, e.g., ganciclovir, foscarnet, and ciofovir; protein synthesis or virus assembly or budding; or an immune response stimulator such as an interleukine or interferon may be used in combination with an invention composition. Such combinations can additionally be formulated into pharmaceutical compositions and kits as set forth herein.

The invention further provides kits comprising one or more compositions of the invention, including pharmaceutical formulations, packaged into suitable packaging material. In one embodiment, a kit includes p30. In another embodiment, a kit includes a nucleic acid encoding p30. In additional embodiments, a kit includes an LTβR or TNFR1 agonist, and instructions for use in treating a subject having or at risk of having a herpesvirus (e.g., CMV) infection. In a particular embodiment, an LTβR or TNFR1 agonist comprises one or more ligands, for example, p30 (LIGHT), LTα, TNF or LTα1β2, or an antibody (e.g., human or humanized). In still another embodiment, a kit includes an antiviral agent (e.g., in a pharmaceutical carrier).

In other embodiments, a kit includes a label or packaging insert including instructions for identifying a compound that inhibits herpesvirus (e.g., CMV) infection. The instructions may comprise, for example, contacting LTβR or TNFR1 with a test compound under conditions allowing binding; measuring LTβR or TNFR1 activity in the presence of the test compound; and comparing activity in the presence of the test compound to the absence of the test compound in vitro (in solid phase, in solution or in cells), in vivo, or ex vivo.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating CMV infection. Kits of the invention therefore specifically include kits that include instructions for using the kit components in any of the methods of the invention.

Thus, invention pharmaceutical compositions can be included in a container, pack, or dispenser together with instructions for administration to a subject, e.g. a subject having or at risk of having herpesvirus (e.g., CMV). Instructions may additionally include indications of a satisfactory clinical endpoint or of any adverse symptoms that may occur, or additional information required by the Food and Drug Administration for use on a human subject.

The instructions may be on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a buffering agent, a preservative, or a protein/nucleic acid stabilizing agent. The kit can also include control components for assaying for activity, e.g., a control sample or a standard. Each component of the kit can be enclosed within an individual container or in a mixture and all of the various containers can be within single or multiple packages. For example, a composition can be packaged into an ampule or other dispenser having a label attached thereto including ingredients, or instructions or dosages for administering the composition locally or systemically to a subject having or at risk of having herpesvirus (e.g., CMV) infection.

As described in further detail below, the polypeptides of the invention (e.g., HVEM:Fc) have been demonstrated to have anti-inflammatory properties. Accordingly, using the methods and compositions described herein, the present invention provides a method of treating or inhibiting and inflammatory reaction or disorder in a cell, tissue or subject. The method includes contacting the cell, tissue or subject having an inflammatory reaction or disorder with an inhibiting effective amount of the fusion polypeptide or a composition containing the fusion polypeptide of the invention. As described herein, the formulation and compositions can be readily identified by one skilled in the art using teaching described herein or readily available to a person skilled in the art. For example, a fusion polypeptide of the invention may be administered topically to an inflamed site on a subject. Such topical administration includes administering the polypeptide of the invention in, for example, a lotion or salve. Alternatively, the polypeptides of the invention may be administered systemically. Such systemic administration includes, for example, intraperitoneal injections, subcutaneous injections, intravenous injections or orally.

The invention also provides methods of treating a subject having or at risk of having herpesvirus (e.g., CMV) infection. A method includes contacting the subject with an amount of a LTβR or TNFR1 agonist sufficient to treat herpesvirus (e.g., CMV) infection. In one embodiment, the agonist comprises a ligand (e.g., polypeptide such as p30

(LIGHT), LTα, TNF or LTα1β2) or an antibody (e.g., fully human or humanized antibody having the binding specificity of a monoclonal antibody denoted 3C8, 3H4 or 4H8). In one aspect, the amount is sufficient to reduce herpesvirus (e.g., CMV) proliferation, replication, protein expression, or apoptosis in cells infected with herpesvirus (e.g., CMV). In another aspect, the amount is sufficient to reduce one or more symptoms (e.g., cytopathicity) associated with CMV infection in the subject. In yet another aspect, the subject is further contacted with an antiviral agent. In still another aspect, the subject is a neonate.

Although infection with human cytomegalovirus (HCMV), a β-herpesvirus, is widespread and acquired early in life, this virus also causes disease in immune compromised individuals. Following primary infection, HCMV persists in a latent form, a characteristic of all herpesviruses. Disease results from reactivation of latent virus following immune system suppression, for example, due to immunosppressive drug use in organ or tissue transplantation, or chemotherapy/radiation for tumors, as well as disease or pathogens that cause immune suppression, such as HIV (AIDS).

The invention therefore further provides methods of treating a subject having or at risk of reactivating herpesvirus (e.g., CMV). A method includes contacting the subject with an amount of a LTβR or TNFR1 agonist sufficient to inhibit HSV (e.g., CMV) reactivation. In one embodiment, the subject is immune compromised, for example, suffers from cancer or HIV infection. In another embodiment, the subject has or is at risk of having a blood transfusion or bone marrow transplant, organ transplant (e.g., liver, kidney, heart) or tissue transplant (e.g., skin, cornea). In yet another embodiment, the subject has or is at risk of having arteriosclerosis or multiple sclerosis.

Primary CMV infection can cause disease. For example, infection of neonates when transmitted from mothers to the fetus is the leading cause of acquired deafness and mental retardation in children. Thus, in yet another embodiment, the subject is a female who is pregnant or is at risk of pregnancy.

The invention additionally provides methods of treating a subject having or at risk of having a disorder associated with herpesvirus (e.g., CMV) infection. A method includes contacting the subject with an amount of a LTβR or TNFR1 agonist sufficient to inhibit herpesvirus (e.g., CMV) thereby treating a subject having or at risk of having a disorder associated with herpesvirus (e.g., CMV) infection. In one embodiment, the disorder comprises pneumonia, vascular pathology (e.g., arteriosclerosis), CMV hepatitis, CMV retinitis, CMV pneumonitis, CMV nephritis or CMV mononucleosis. In another embodiment, the disorder comprises a demyelinating disease (e.g., multiple sclerosis). In still another embodiment, the disorder comprises congenital cytomegalaic inclusion disease.

The methods of the invention are also applicable to herpesvirus in general. herpesvirus infection and associated disorders therefore include β- and γ-herpesvirus infections and associated disorders. β-herpesvirus include, for example, HHV6 and HHV7, which are associated with febrile illness in children and demyelinating diseases, such as multiple sclerosis in adults. γ-herpesvirus include, for example, HHV8 and EBV, which are associated with Kaposis sarcoma, Hodgkins leukemia or non-Hodgkins leukemia or lymphoma.

The methods of the invention, including treating a p30 polypeptide-mediated disorder, an inflammatory reaction or disorder, a tumor or herpesvirus infection or reactivation in a subject, likely results in an improvement in the subjects' condition, a reduction of one or more symptoms or decreasing the subject's risk for developing one or more symptoms associated with the disorder. Improvements therefore include one or more decreased symptoms associated with autoimmunity, hypersensitivity, graft vs. host disease, inflammation (e.g., pain or swelling or immune cell infiltration into the affected tissue or organ, tissue damage caused by such inflammation, etc.), tumor size or tumor growth rate or tumor metastasis, herpesvirus (e.g., CMV, EBV) proliferation, cytopathicity (cell toxicity), viral titre, susceptibility to opportunistic infection, reduction of artherosclerotic lesions or plaque formation, symptoms of multiple sclerosis, etc.

An improvement may also mean a reduction in the frequency or amount of a drug used for treating a subject having or at risk of having the disorder. For example, autoimmune patients treated with steroids may require less steroid when additionally treated with an invention composition or method. Similarly, herpesvirus infected patients treated, for example, with ganciclovir, or other DNA polymerase inhibiting drug (e.g., foscamet, cidofovir) may require less of the drug when additionally treated with an invention composition or method. An improvement therefore includes reducing the dosage frequency or dosage amount of steroid that the subject was administered in comparison to the dosage frequency or amount administered without treatment with the invention composition or method.

An improvement may be relatively short in duration, e.g., several hours, days or weeks, or extend over a longer period of time, e.g., months or years. The improvement need not be a complete ablation of any or all symptoms of the disorder. For example, reducing a symptom of inflammation, such as the severity of pain for several hours is an improvement. Thus, a satisfactory clinical endpoint for a method of treatment is achieved when there is an incremental improvement in the subjects' condition or a partial reduction of associated symptoms, over a short or long duration.

Candidate subjects for the methods of the invention include those having an infection or a disorder as described herein or known in the art as well as subjects at risk of developing infection, reactivation or a disorder. The invention methods are therefore applicable to prophylactic treatment of a subject who is at risk of reactivation or developing a disorder associated with infection but either does not have or has not yet exhibited detectable symptoms of the disorder. A particular example of an at risk subject would be one with a family history or other genetic characteristic indicating predisposition to a cancer. Such at risk subjects can be identified using genetic screening for the presence of the genetic lesion or inquiry into the subjects' family history to establish that they are at risk of the disorder. Another example of an at risk subject would be one susceptible to HSV infection, for example, an immunocompromised subject or a subject exposed to HSV from contact with another person. Yet another example of an at risk subject would be a neonate at risk of HSV transmitted from the mother to the fetus. Subjects also include those who have had an initial HSV infection followed by a period of latency in which the virus is still present but infectious virus is not recovered. Latency can be reversed, for example, by immunosuppression which causes virus reactivation. Thus, subjects in which virus is latent are included in the methods of the invention, particularly at risk of immunosuppression.

The term "subject" refers to animals, typically mammalian animals, such as humans, non human primates (apes, gibbons, chimpanzees, orangutans, macaques), domestic animals (dogs and cats), farm animals (horses, cows, goats, sheep, pigs), experimental animals (mouse, rat, rabbit, guinea pig) etc. Subjects include neonates. Subjects also include animal disease models (e.g., inflammatory disease animals, animals susceptible to HSV infection, etc.).

The following examples are meant to illustrate the invention and not to limit it.

EXAMPLES

Materials for the Examples

Construction, expression and purification of the bivalent chimeric proteins formed with the Fc region of human IgG1 and the ligand binding domains of Fas:Fc (Brunner (1995) Nature 373:441), TNFR60 (Crowe (1994) J. Immunol. Methods 168:79) and human LTβR:Fc (Crowe (1994) Science 264:707) have been previously described. The extracellular region of HVEM was generated by PCR using Taq DNA polymerase amplified sequences from pBEC 10 DNA encoding 1 to K 184 using the forward primer 5' CGGAGATCTGAGTTCATCCTGCTAGCTGG-3' (SEQ ID NO:1) and reverse primer 5' ATAGGATCCCTTG-GTCTGGTGCTGACATTCC-3' (SEQ ID NO:2). The amplified HVEM product was ligated in-frame into the baculovirus vector pVL1392 (Pharmingen) containing the human Fc IgG1. A similar construct of HVEM:Fc with Fc region from rabbit IgG1 was produced in CHO cells, purified and used as an immunogen to produce rabbit anti-HVEM antibody. LTβR:Fc was constructed from a mouse LTβR (mLTβR) DNA fragment that encodes amino acid residues 1 to Met221 of the extracellular domain (Force et al. (1996) J. Immunol. 1995.1 155:5280) by PCR using Taq DNA polymerase with forward primer 5' GACGTCA-GATCTTCCCACCTTTCCTCCTA 3' (SEQ ID NO:3) and reverse primer 5' GAACAGAGATCTCATTGCTCCTG-GCTCTG 3' (SEQ ID NO:4).

LTα and LTαTyr108Phe were produced in insect cells using recombinant baculovirus as described (Crowe et al. (1994) J. Immunol. Methods 168:79). Recombinant soluble LTα1β2 (Browning et al. (1996), cited supra), TNF (Browning and Ribolini (1989) J. Immunol. 143:1859), and monoclonal antibodies to LTα (BF7), and LTβ (C37, B9 and B27) (Browning et al. (1995), cited supra) were gifts from Jeffrey Browning (Biogen, Inc.). The immunoprecipitating anti-LTα antibody (clone 9B9) was from Boehringer Mannheim. Anti-CD3 (OKT3) was produced in ascites in BALB/c mice and used at 1 µg/ml protein. Purified recombinant HSV gD_1 proteins and mutants were produced in baculovirus as previously described in detail (Nicola et al. (1996) J. Virol. 6:3815). FITC-anti-CD4 and CD8 antibodies were obtained from Becton-Dickenson. Normal human dermal fibroblasts (NHDF) (Clonetics, San Diego, Calif.), were cultured in DMEM (Gibco/BRL) supplemented with 10% fetal bovine serum. HCMV strain AD169 (American type culture collection) stocks were prepared and quantified by limiting dilution plaque formation assay on NHDF. Purified recombinant soluble LIGHT, (Rooney et al. (2000) J. Biol. Chem. 275:14307), mutant LIGHTG119E (Rooney et al. (2000) J. Biol. Chem. 275:14307), LTαY108F (Williams-Abbott et al. (1997) J. Biol. Chem. 272:19451) were purified as described. Anti-LTβR (goat) antibodies and decoy receptors TNFR1-Fc and LTβR-Fc were purified as described (Rooney et al. (2000a) Methods Enzymol. 322:345). Interferon-α, IFNβ, and their specific antibodies (sheep polyclonal) were from Research Diagnostics (Flanders, N.J.), and Fas ligand and TRAIL were from Alexis Biochemicals (San Diego, Calif.). ICAM-1 was detected with mAB 2146 (Chemicon) by flow cytometry (FACS Caliber, Becton-Dickinson) and staining with goat anti-mouse IgG conjugated to R-phycoerythrin. Anti-IκBα (rabbit polyclonal Ab, Upstate Biotech) and anti-FLAG epitope (Sigma) were used in western blotting as described (Benedict et al., 1999). Anti-HCMV monoclonal antibodies IE1, (clone 63 and 27); pp28, gB and gH were prepared as described (Sanchez et al. (1998) J. Virol. 72:3321).

Example 1

Expression of an HVEM Ligand on T Cells

This example demonstrates that both malignant and normal human T-cells express a cell surface ligand for HVEM. A fusion protein containing the extracellular domain of HVEM and the Fc region of human IgG (HVEM:Fc) was constructed. Experiments demonstrated that HVEM (as a soluble, recombinant HVEM:Fc) bound to normal (freshly isolated) human T cells.

Peripheral blood mononuclear cells were obtained from normal donors by Ficoll-Hypaque. They were activated with anti-CD3 antibody for 5 days in medium with IL-2. Cells were re-stimulated with PMA or PMA and ionomycin for 4 hours and then dual stained with FITC-CD4 or FITC-CD8 and HVEM:Fc detected with anti-huIgG-PE as described above. FITC fluorescence with compensation was used to gate on CD4 and CD8 T cell subpopulations.

Receptor binding was determined by incubating graded concentrations of HVEM:Fc or control IgG with activated II-23.D7 cells. The II-23.D7 cell line is a human CD4+T cell hybridoma (Ware (1986) Lymphokine Res. 5:313) and is maintained in RPMI1640 medium with 10% fetal bovine serum (FBS) and antibiotics. II-23.D7 cells were activated for 4 hours at 37° C. with phorbol myristate acetate (PMA) (100 ng/ml), or PMA (100 ng/ml) and ionomycin (1 µg/ml). The cells were washed and incubated for 30 minutes at 4° C. in Hanks Balance Salt Solution (HBSS) (supplemented with 10% bovine calf serum and 0.1% $NaN_3$) containing HVEM: Fc, LTβR:Fc or human IgG at 5 µg/ml, and then stained with goat anti-human IgG conjugated with phycoerythrin (anti-huIg-PE). Stained cells were analyzed by flow cytometry (FACSCaliber, Becton-Dickenson). Receptor binding was determined by calculating the fluorescence intensity=(mean fluorescent channel) (% positive fluorescent events), where a positive event has a fluorescence value>98% of the value for normal IgG. Specific fluorescence intensity represents the fluorescence intensity after subtraction of the value for control IgG. Each histogram represents $10_4$ events.

These experiments demonstrated that HVEM:Fc bound specifically to the human CD4+ T cell hybridoma, II.23.D7 (Ware et al. (1986) see infra) after activation with the calcium ionophore, ionomycin, and PMA, but not PMA alone was detected by flow cytometry (FIG. 1A). Specific HVEM:Fc binding was also detected on T lymphocytes derived from human peripheral blood (FIG. 1B). These findings indicated that the both malignant and normal human T-cells expressed a cell surface ligand for HVEM. Half-maximal binding of HVEM:Fc to II.23.D7 cells was achieved at ~20 nM (FIG. 1C). The II.23.D7 cell line is also induced by PMA to express LTα and β and TNF (see, e.g., Ware (1992)J. Immunol. 149:3881).

Example 2

Binding Characteristics of HVEM and its Ligands; HVEM Binds LTα

This example demonstrates the binding characteristics of HVEM using the soluble, recombinant HVEM:Fc. To determine whether HVEM might bind to TNF or LTαβ complexes, LTβR:Fc and TNFR:Fc were used as competitive inhibitors of HVEM:Fc binding to activated II-23.D7 cells. These experiments found that the LTα homotrimer, but not TNF or LTα1β2 competed for HVEM:Fc (soluble HVEM) binding.

Competition of Binding by LTβR:Fc. Activated II-23.D7 cells (PMA and ionomycin as described in Example 1) were pre-incubated with LTβR:Fc or TNFR60:Fc (100 μg/ml) for 30 minutes at 4° C. HVEM:Fc-rabbit (2 μg/ml) was then added, incubated for 30 minutes and the cells stained with goat anti-rabbit IgG-PE to detect HVEM:Fc-rabbit. Rabbit IgG was used to determine background staining. Binding of HVEM:Fc to activated II-23.D7 cells was competed with graded concentrations of LTβR:Fc, TNFR60, Fas:Fc, or IgG as described above.

Competition of Binding by LTα Homotrimer. II-23.D7 cells were activated and HVEM:Fc was preincubated with recombinant LTα or LTα1β2 for 30 minutes at 4° C. The mixture was added to activated II-23.D7 cells and then stained with anti-huIgG-PE. Fluorescence staining with HVEM:Fc+LTα was equal to background with normal IgG.

Figure 2A:
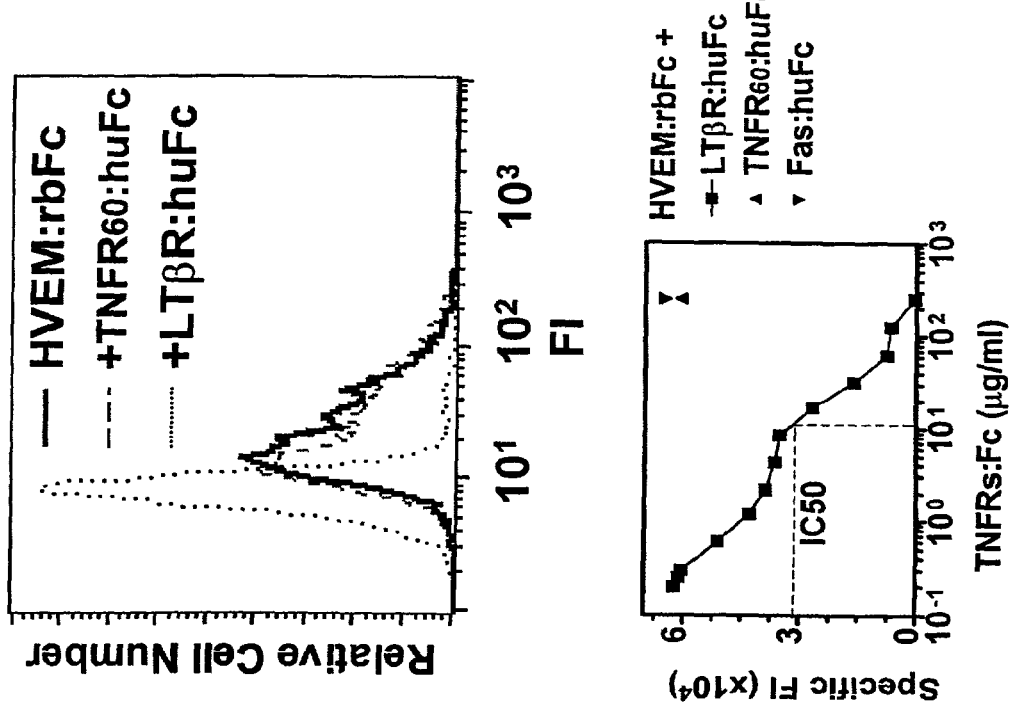
FIG. 2A is a pair of diagrams. The upper diagram is a flow cytometric histogram showing that HVEM:Fc fusion protein binding to activated 11–23.D7 cells is competed by LTβR:Fc fusion protein. The lower diagram is a line graph showing dose-dependent inhibition of HVEM:Fc fusion protein binding by LTβR:Fc fusion protein.
Figure 2B:
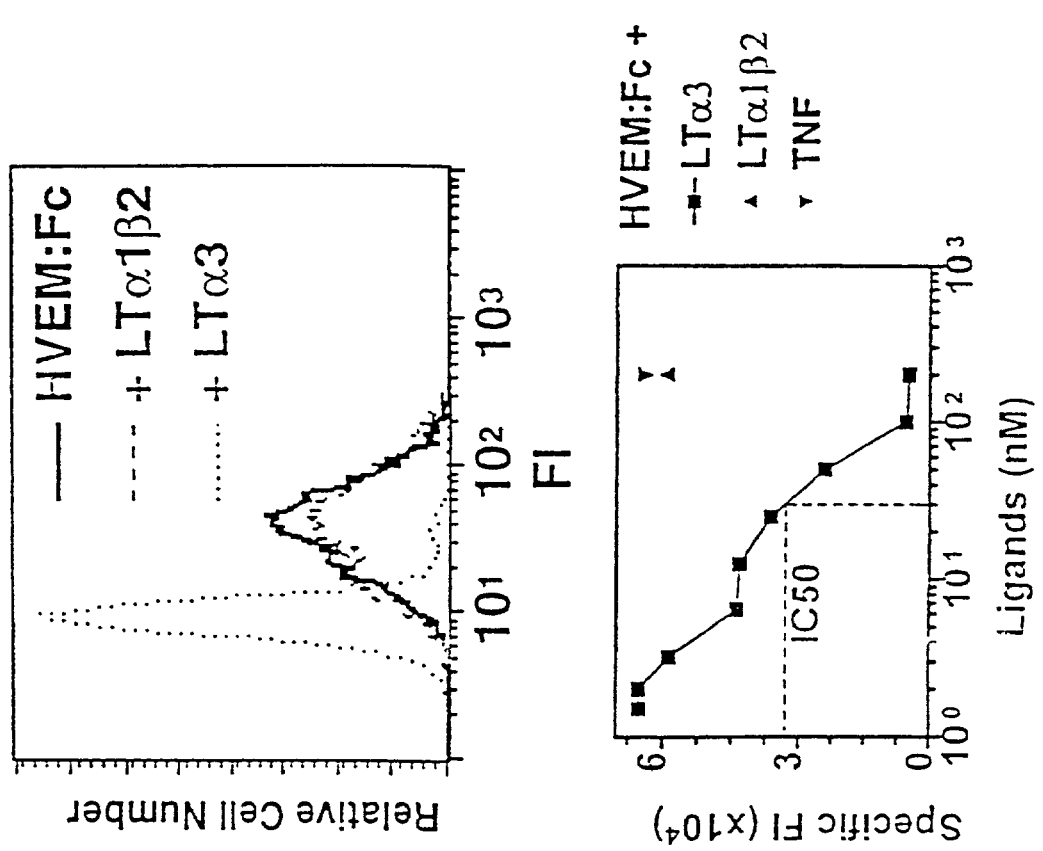
FIG. 2B is a pair of diagrams. The upper diagram is a flow cytometric histogram showing that HVEM:Fc fusion protein binding is competed by LTα homotrimer. The lower diagram is a line graph showing dose-dependent inhibition of HVEM:Fc fusion protein binding by the LTα homotrimer.
Figure 3:
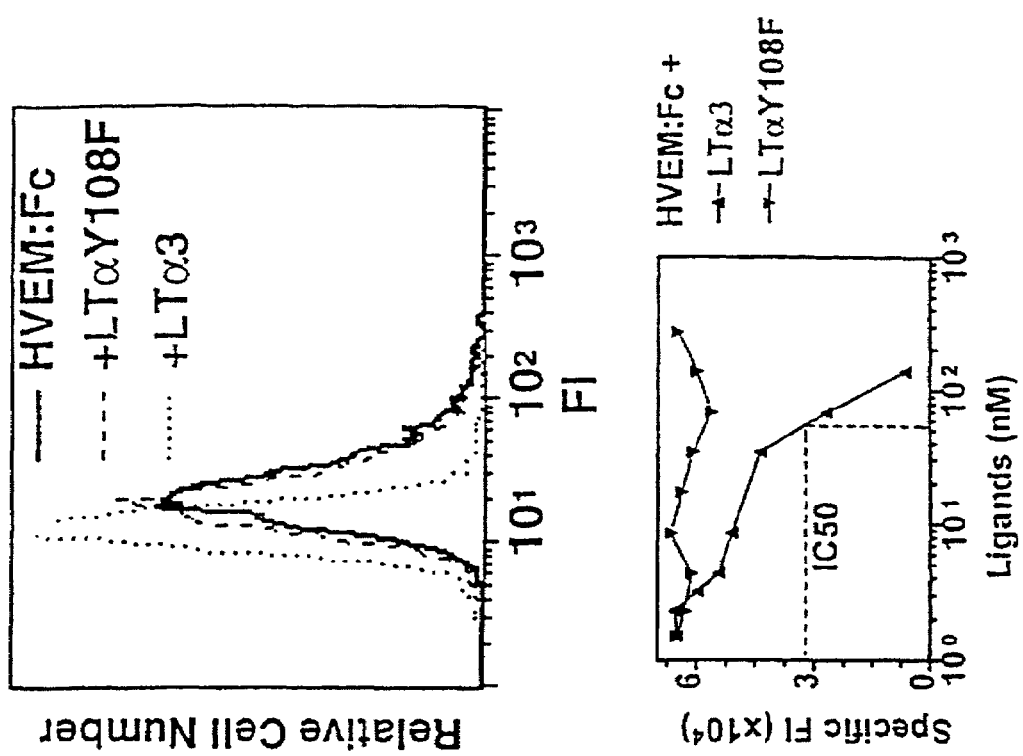
FIG. 3 is a pair of diagrams. The upper diagram is a flow cytometric histogram showing that the Tyr108Phe variant of naturally occurring LTα fails to compete for HVEM:Fc binding to II-23.D7 cells and the lower diagram is a line graph showing a LTα and LTα (Tyr108Phe) competition binding analysis.

To determine whether HVEM might bind to TNF or LTαβ complexes, LTβR:Fc and TNFR:Fc were used as competitive inhibitors of HVEM:Fc binding to II-23.D7 cells activated with PMA and ionomycin utilizing an HVEM:Fc construct with rabbit IgG Fc (Montgomery (1996) supra). The LTβR:Fc and HVEM:Fc (Fc of human IgG1), but not TNFR60:Fc competed for binding of HVEM:Fc (rabbit) (FIG. 2A). In addition, neither of the related receptor fusion proteins, Fas:Fc and TNFR80:Fc competed for binding of HVEM:Fc. However, surprisingly, the LTα homotrimer, but not TNF or LTα1β2 competed for HVEM:Fc binding (FIG. 2B). A TNFR60 binding mutant of LTα in which tyrosine (Tyr) at position 108 is replaced with phenylalanine (Phe) (Tyr108Phe) (Goh (1991) Protein Eng. 4:785) did not compete (FIG. 3). These results indicated that the putative HVEM ligand has characteristics in common with LTαβ heterotrimers and LTα, but also has features that distinguish it from LTα1β2 and TNF. Thus LTα2β1 could be a putative surface ligand recognized by HVEM:Fc, with the caveat that the HVEM binding site(s) on LTα2β1 is not the same as TNFR60. Alternatively, HVEM:Fc might recognize a novel ligand. A biochemical approach was used to distinguish between these possibilities.

Example 3

Biochemical Characterization of the HVEM Ligand (LIGHT)

This example demonstrates the purification of LIGHT (p30) by affinity chromatography using soluble, recombinant HVEM:Fc. Analysis of proteins that bind HVEM:Fc by Two-dimensional (2D) electrophoresis showed that p30 polypeptides migrated as a broad band (pI 7 to 8.5) and that under lower intensity p30 resolves into three bands.

SDS-PAGE Analysis. II-23.D7 cells were activated for 2.5 hours with PMA or PMA and ionomycin (as in Example 1); washed twice with phosphate buffered saline (PBS), once with cysteine-methionine deficient RPMI; and then resuspended in this medium containing 10% dialyzed FBS, 250 μCi each of $^{35}$S-methionine and $^{35}$S-cysteine, and activating agents for 1.5 hours. The culture supernatants were harvested and the cells lysed in buffer containing 2% NP40, HEPES pH7.0, 20 mM EDTA, 150 mM NaCl with leupeptin and aprotinin (at 10 μg/ml), PMSF (1 mM) and iodoacetamide (20 mM). The extract was precleared with human IgG (10 μg), where indicated, anti-LT antibodies and protein G beads. The receptor:Fc fusion proteins (10 μg/ml) were then added to the samples and precipitated with protein G beads. Labeled proteins were analyzed by reducing SDS-PAGE and phosphoimage (pixel range 6–200).

Cellular extracts prepared as in the above paragraph were first pre-cleared with 10 μg of mouse IgG or monoclonal antibodies to LTα or LTβ and then HVEM:Fc was added to precipitate ligands. The proteins bound to HVEM:Fc were then resolved by reducing SDS-PAGE and detected by phosphoimage.

Purification of HVEM Ligand, p30. II-23.D7 cells were activated with PMA (100 ng/ml) or PMA and ionomycin (1 μg/ml) for 2.5 hours, followed by labeling with $^{35}$S-methionine and -cysteine as in the above two paragraphs. Cell extracts were pre-cleared with human IgG (5 μg) and protein G beads to remove nonspecifically binding proteins. The extract was then depleted of LTα by treatment of the extract with TNFR60:Fc and protein G beads. HVEM:Fc and protein G beads were then added to the extract and incubated. In each case, the beads were washed three times to remove the contaminating proteins in the non-bound fraction. The beads were eluted in buffer containing 8M urea and analyzed in the first dimension by isoelectric focusing (gradient formed with an ampholine mixture of pI of 5–7 (50% 0, 3–10 (40%), 2–11 (10%) and reducing SDS-PAGE (15% gel) in the second dimension.

The purification of p30 by HVEM:Fc was monitored by comparison to samples purified by LTβR:Fc or TNFR60:Fc. LTβR:Fc purified proteins, LTα1β2, were isolated from II-23.D7 cells stimulated with PMA is shown in FIG. 4A and proteins bound to TNFR60:Fc that was used to deplete LTα from the extract is shown in FIG. 4B. p30 purified by HVEM:Fc as described above is shown in FIG. 4C. Shown in the first lane of each gel are $^{14}$C-labeled molecular weight markers and in the second lane are the receptor:Fc bound proteins run in the second dimension only.

LTα is secreted by II23.D7 cells after activation with PMA (Ware et al. (1992), cited supra; Crowe et al. (1994) Science 264:707). HVEM:Fc and TNFR:Fc precipitated secreted LTα from II-23.D7 cells stimulated with PMA and ionomycin as indicated by SDS-PAGE. LTα migrates as a range of molecular weights due to heterogeneity in glycosylation (Browning et al. (1991), cited supra). TNFR60:Fc, but not HVEM:Fc also precipitated TNF (17 kDa, thereby confirming the results of the competition studies described supra. LTβR:Fc, as expected, did not bind any secreted proteins, but precipitated the LTβ (33 kDa) and LTα (23–25 kDa) complex from detergent extracts of PMA activated II-23.D7 cells. However, when the stimulus included ionomycin and PMA, LTβR:Fc precipitated a major band at 30 kDa, as well as a small amount of LTβ at 33 kDa and LTα at 23–25 kDa. TNFR60:Fc precipitated a 23 kDa protein identical in size to the LTα precursor. By contrast, HVEM:Fc precipitated both the 30 kDa and 23 kDa proteins. Three different receptor blocking monoclonal antibodies to LTβ failed to remove the 30 kDa protein from the extract prior to the addition of HVEM:Fc indicating that the p30 protein is antigenically unrelated to LTβ. However, anti-LTα antibodies removed the 23 kDa band from the extracts indicating relatedness of it to LTα. The inability of LTα antibodies to preclear both the 30 kDa and 23 kDa bands demonstrate that these proteins are not associated with each other, unlike LTα and LTβ which form heterotrimers (Androlewicz et al., cited supra).

LIGHT (p30) was purified from II-23.D7 cells by affinity chromatography. Successive TNFR60:Fc and HVEM:Fc steps were used, such that LTα is removed from the extracts by TNFR60 and thus does not interfere with p30 binding to HVEM:Fc.

Two-dimensional (2D) electrophoresis of proteins that bind HVEM:Fc, TNFR60:Fc or murine LTβR:Fc revealed that p30 has a distinct charge-to-mass ratio when compared to LTα and LTβ. LTβ in the LTα1β2 complex precipitated by LTβR:Fc is acidic with four distinct charge isomers ranging in pI from 5–6.5 with a detectable increase in mass of the acidic forms (FIG. 4A). LTα, as a complex with LTβ or the LTα homotrimer bound to TNFR60 (FIG. 4B), has seven distinct isomers ranging in pI from 7 to 8.5; the 23 kDa LTα precursor has the most basic pI (> or =9). The pI of LTα without signal sequence is 8.9. These results are characteristic of glycosylation adducts and agree fully with previously published studies for LTα and LTβ (Browning et al. (1991), cited supra). By contrast, p30 migrated as a broad band (pI 7–8.5) that under lower intensity resolves into three bands (FIG. 4C). The charge heterogeneity with no discernable change in mass of p30 is possibly the result of post-translational modification such as addition of phosphates or phospholipids.

These results clearly demonstrate that HVEM binds a novel cell surface protein of 30 kDa (isolated from the human CD4+ T cell hybridoma II.23.D7) with isomers of pI 7 to 8.5, which is referred to as p30 or HVEM ligand (or LIGHT). p30 is antigenically and physically distinct from LTβ. The HVEM ligand is also recognized by LTβR:Fc, but not TNFR.

Example 4

HSV gD Envelope Glycoprotein Competes with the Endogenous HVEM Ligand (p30) for Binding to HVEM:Fc This example demonstrates the binding of herpesvirus HSV gD-1 protein to HVEM and that soluble gD-1 competes with HVEM-ligand, or p30 (LIGHT) for binding to HVEM. Data showing that HSV gD-1 protein is an antagonist of p30 (LIGHT) binding to HVEM also demonstrates that p30 can act as an antagonist of herpesvirus gD-1 protein to HVEM.

HVEM:Fc (2 µg/ml) was pre-incubated for 30 minutes at 4° C. with gD-1 (250 µg/ml) or gD-1 (Δ290–299) (100 µg/ml), and then added to PMA and ionomycin activated II-23.D7 cells (as in Example 1). Background staining was determined with huIgG and is equal to HVEM:Fc+gD-1 (Δ290–299). Binding of HVEM:Fc to activated II-23.D7 cells was competed with graded concentrations of gD-1 or gD-1 (Δ290–299) (for protocol, see Example 1).

Figure 5:
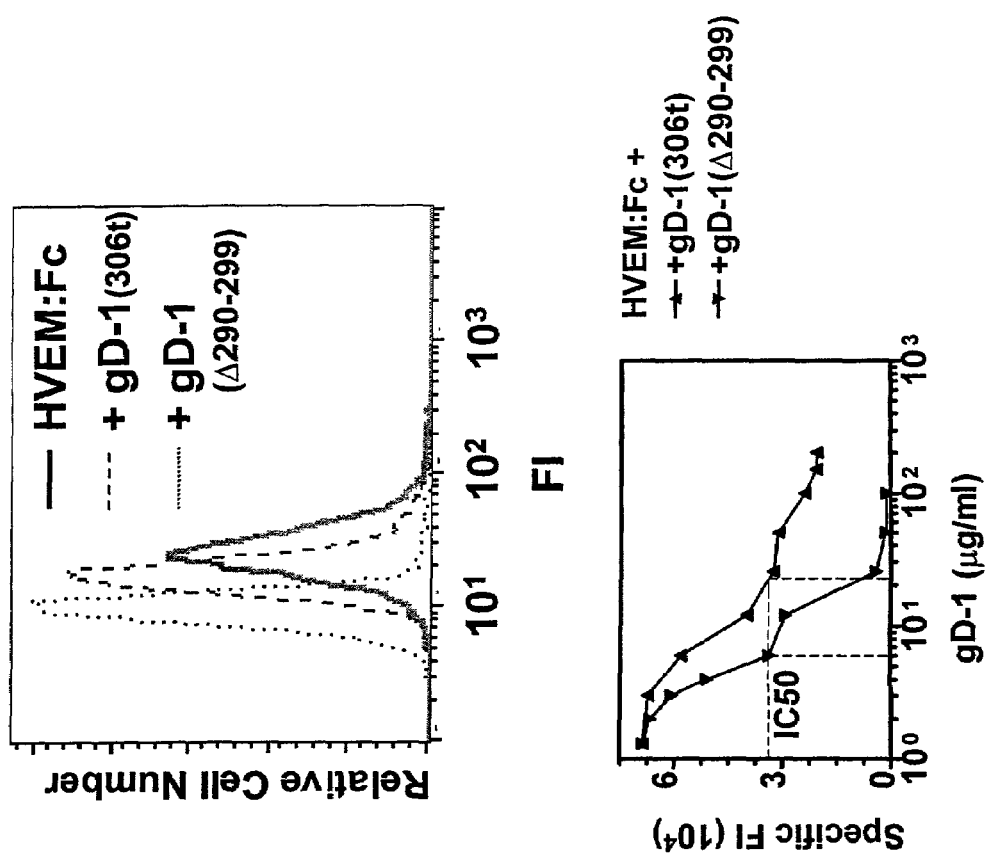
FIG. 5 is a pair of diagrams. The upper diagram is a flow cytometric histogram showing that HVEM:Fc fusion protein binding is competed by HSV gD-1 glycoprotein. The lower diagram is a line graph showing dose-dependent inhibition of HVEM:Fc fusion protein binding by HSV gD-1 glycoprotein.

The possibility that HSV gD might function as an antagonist of HVEM-ligand (cellular ligands, e.g., p30) binding to HVEM was suggested by the binding of HSV gD-1 protein to HVEM. Soluble gD-1 and a mutant of gD, gD-1 (Δ290–299t) with enhanced binding for HVEM, were both effective at blocking HVEM binding to the surface of activated 11–23.D7 cells (FIG. 5A) (expressing p30). The effective inhibitory concentration of the gD-1 proteins correlated with their affinity for HVEM (FIG. 5B). The binding of LTβR:Fc or TNFR60:Fc to PMA or PMA/ionomycin-activated II-23.D7 cells was not inhibited by gD-1 (Δ290–299t), indicating that the HVEM:gD-1 interaction is highly specific. This result suggests that gD-1 has co-evolved specifically for binding to HVEM, even though HVEM binds to ligands that are recognized by TNFR60 and LTβR. These results indicate that gD-1 is a membrane-anchored virokine and may modulate HVEM signaling activities during entry or egress of HSV from the infected cell.

Example 5

Crosslinking of Cell Surface HVEM Results in Lymphocyte Activation

This example demonstrates that anti-HVEM antibody promoted the enhanced proliferation of peripheral blood lymphocytes cells (PBLs), including T cells and B cells. Data showing that anti-HVEM antibody can promote proliferation of PBLs (which also express HVEM-ligand, p30, or LIGHT) also demonstrates that cell-associated p30 (LIGHT) can function as a proliferation-inducing signal for PBLs. Furthermore, the finding that anti-HVEM antibody added to B cell lines cultured in low serum medium stimulated their growth in a dose-dependent fashion also demonstrated that HVEM signaling, e.g., LIGHT binding to HVEM, can stimulate B cell proliferation.

T Cell Activation. Freshly isolated peripheral blood lymphocytes were incubated in medium containing graded dilutions of rabbit anti-HVEM or pre-immune sera (Montgomery (1996) supra) and PMA at a sub-mitogenic dose (1 µg/ml). Proliferation was measured after 3 days by incorporation of 3H-thymidine into DNA as assessed by β-scintillation counting.

Freshly isolated peripheral blood lymphocytes were activated with phytohemagglutinin (PHA) at 5 µg/ml and cultured in medium with IL-2. After 17 days the cells were re-stimulated with graded dilutions of anti-HVEM antiserum and anti-CD3 (OKT3) antibody at a sub-mitogenic concentration (1.5 µg/ml). Proliferation was measured after 3 days as above.

B Cellflow Cytometric Analysis. Human lymphoblastoid RAJI cells were subjected to flow cytometric analysis by incubation with anti-HVEM antiserum (1:100 dilution) or control rabbit IgG at 4° C. and the stained with goat anti-rabbit IgG conjugated with phycoerythrin. $10^4$ cells were analyzed for each histogram.

B Cell Activation. RAJI was transferred into medium containing 2% FBS for 24 hours and then incubated for 3 days in the presence of the indicated dilutions of rabbit anti-HVEM antibody or medium alone. Cell proliferation was assessed as described above.

Figure 6:
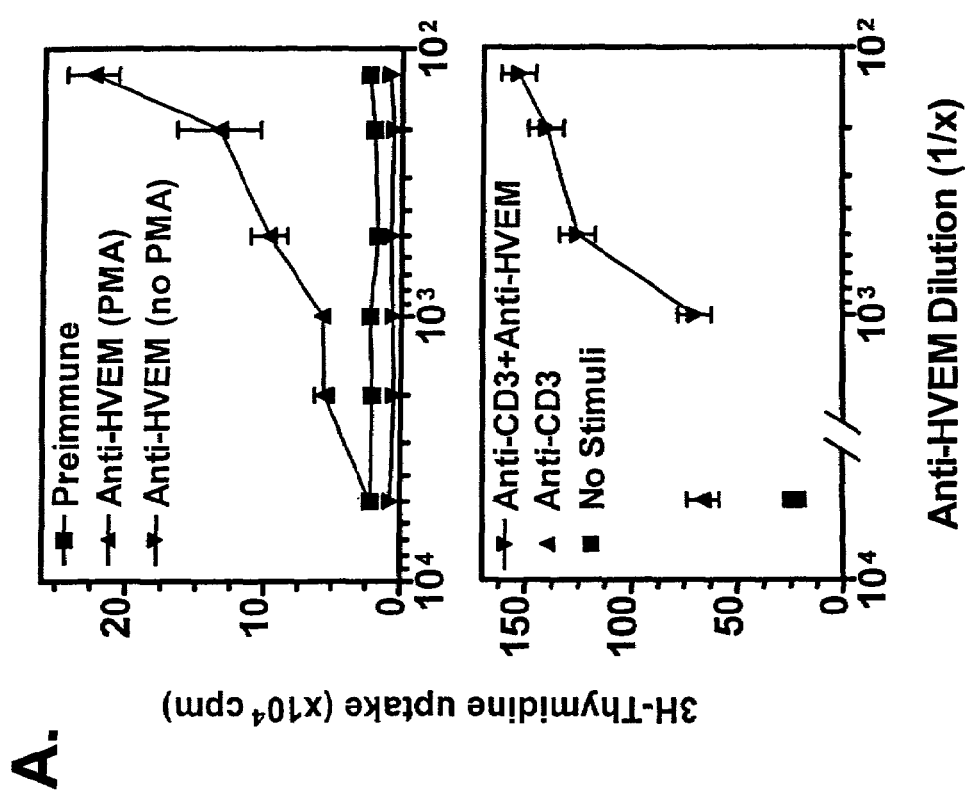
FIG. 6 is a pair of line graphs showing that anti-HVEM antibody stimulates dose-dependent proliferation in freshly isolated peripheral blood T cells (upper line graph) and memory T cells (lower line graph).

HVEM is expressed on resting CD4+ T cells suggesting that it could function as a co-stimulatory molecule for cellular proliferation during the initial phase of an immune response. At suboptimal concentrations of PMA, anti-HVEM antibody promoted the enhanced proliferation of peripheral blood lymphocytes indicated by an increase in the uptake of $^3$H-thymidine measured after 3 days in culture (FIG. 6A). Memory lymphocytes, generated by continued culture for 10 to 17 days after activation with PHA, were also reactivated with anti-HVEM antibody at suboptimal concentrations of anti-CD3 antibody (FIG. 6B). This result indicated that HVEM functions in the effector phase of the immune response. Because antibodies can mimic the action of TNF-related ligands (Engelmann (1990) J. Biol. Chem. 265:14497), these results indicate that the cell-associated 30 kDa HVEM ligand may function as a proliferation-inducing signal for T cells.

Figure 7:
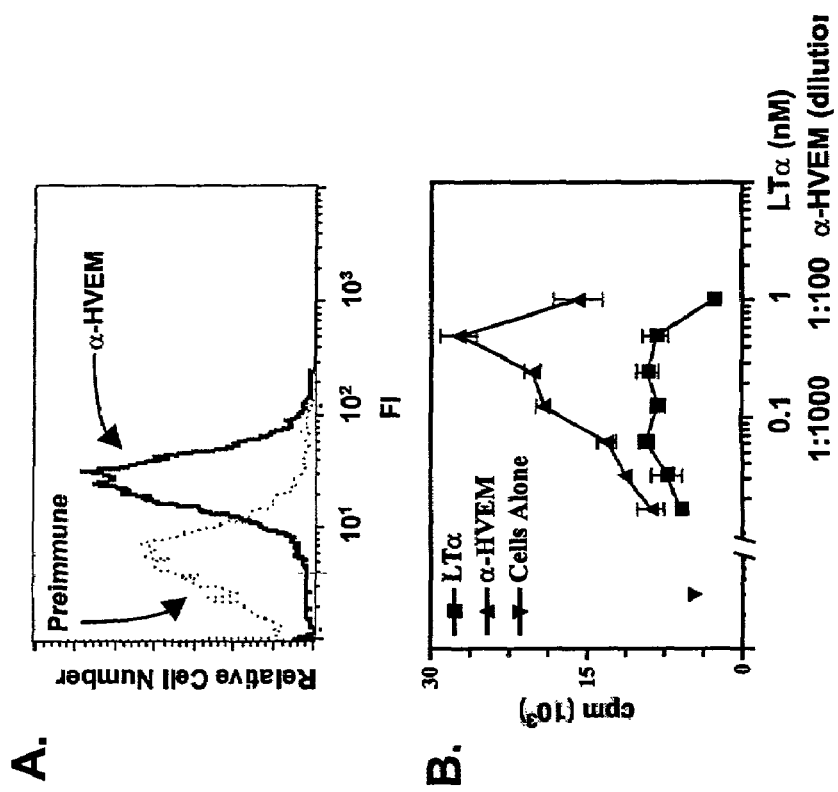
FIG. 7 is a pair of diagrams. The upper diagram is a flow cytometric histogram showing expression of HVEM on RAJI lymphoblastoid cells. The lower diagram is a line graph showing the dose-dependent proliferation of RAJI cells in response to anti-HVEM antibody.

LTα has previously been shown to stimulate growth enhancing activities for B lymphocytes, including Epstein-Barr virus transformed cell lines (Abken (1992) J. Immunol. 149:2785; Estrov (1993) J. Exp. Med. 177:76; Kehrl (1987) Science 238:1144; Gibbons (1994) Eur. J. Immunol. 24:1879). HVEM is also expressed on B lymphoblastoid lines (FIG. 7A). Anti-HVEM antibody, when added to cultures of RAJI B cell lines in medium with 2% serum, stimulated the uptake of $^3$H-thymidine in a dose-dependent fashion, indicating that HVEM can signal maintenance of B cell viability in low serum (FIG. 7B). LTα exhibited a 2 to 3 fold stimulatory effect in this assay. The presence of TNFR60 and TNFR80 as negative growth factors may contribute a low response to LTα. The positive effect of anti-HVEM antibody may be a property unique to p30 (HVEM-ligand, LIGHT).

Example 6

Production of Mouse HVEM:Fc

This example demonstrates the construction of a mouse HVEM:Fc recombinant construct.

The extracellular region of mouse HVEM was amplified by PCR from the mHVEM cDNA (Hsu et al., 1997) starting with Met1 and ending at Ser205 (forward primer=5' tatG-GATTCatggaacctctcccaggat-3'(SEQ. ID. NO. 26), and reverse primer=5'-tatGGATTCggaggagcaggt ggtgtctgt-3' (SEQ. ID. NO. 27); both primers contain a BamHI site. The 550 bp PCR product was purified by Wizard PCR Preps (Promega), digested with BamHI and then ligated in-frame into BglII cut Baculovirus vector pVL1392 (Pharmingen) containing the Fc region of human IgC1 at the 3' end of the HVEM insert (pVL1392-mHVEM:Fc). The ligation reaction mixture was used to transform XL-1 blue competent cells (Stratagene) for a plasmid preparation.

TN5 insect cells ($1.25 \times 10^6$) were plated on a T25 flask in 4 mL Excell 401 Medium (JRH Biosciences) and allowed to attach for 2 hours. TN5 cells were co-transfected with 1 μg pVL1392-HVEMFc plasmid and 250 ng Baculogold™ DNA (Pharmingen) using 14 μg Lipofectin™ (Gibco BRL). The following day the medium was exchanged and the supernatant containing virus was collected after 4 days. The virus was amplified to make a stock for protein production.

Mouse HVEM:Fc was produced in TN5 insect cells and purified to homogeneity as described (Crowe et al., 1994). Briefly, TN5 cells were infected with recombinant baculovirus containing mHVEM:Fc at an MOI of 10. After 3 days the supernatant was harvested, clarified of cells and debris and treated with protease inhibitors. Purified mHVEM:Fc protein was obtained by protein A affinity chromatography with an acidic elution (pH 2.5). Analysis of mHVEM:Fc by SDS-PAGE showed a single band of protein at 58 kDa under reducing conditions (see FIG. 8). The preparation was judged by the Limulus lysate test to be free of detectable endotoxin.

Example 7

Inhibitory Effect of Mouse HVEM:Fc on Inflammation (Delayed-type Hypersensitivity) in Mice This example demonstrates that the soluble, recombinant HVEM:Fc fusion protein of the invention has an inhibitory effect on inflammation in vivo using a art-recognized animal model.

Figure 9:
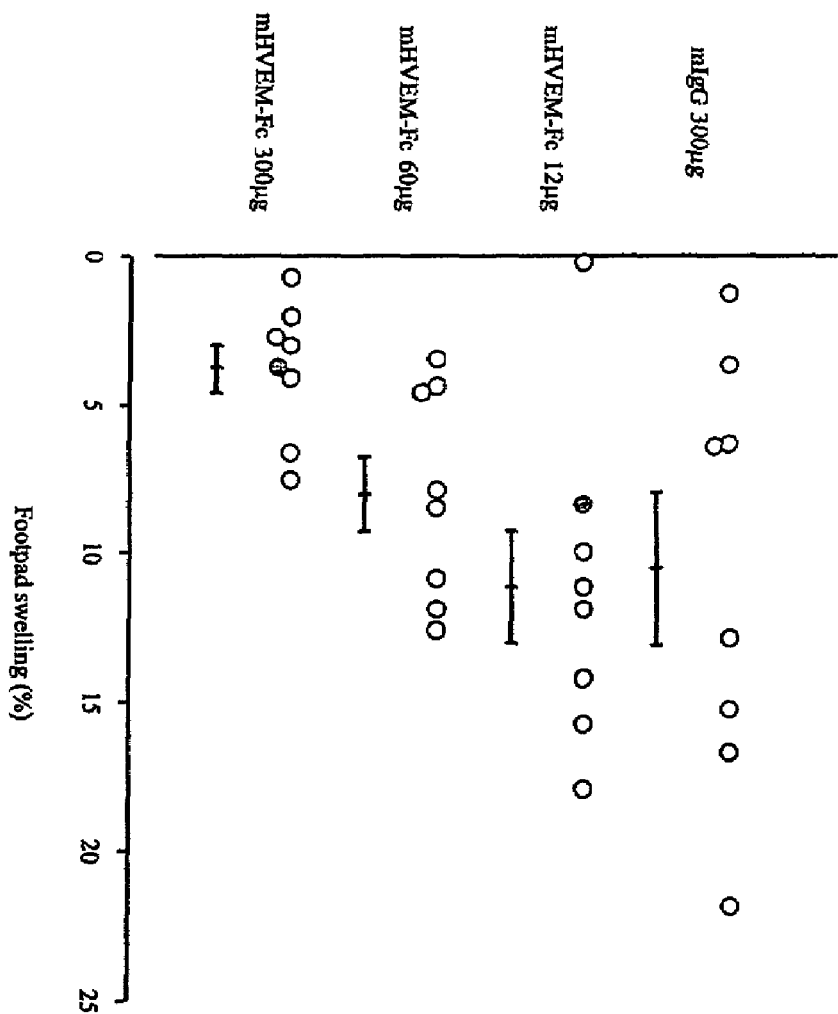
FIG. 9 is a graph demonstrating the effect of HVEM:Fc fusion protein on footpad swelling in mice. Various concentrations of mHVEM:Fc (12, 60 and 300:g) were used to treat inflammation and swelling in BDF1 mice immunized with 50:g OVA absorbed to 1 mg alum and challenged with antigen, see Example 7.

Eight week old female BDF1 mice (Japan SLC Inc., Shizuoka, Japan) (N=8) were immunized with 50 μg OVA adsorbed to 1 mg alum by subcutaneous injection. After 7 days mHVEM:Fc or control IgG was administered by intraperitoneal injection and the mice were challenged on footpad with 50 μg alum-absorbed 10 μg OVA. Measurements of the thickness of right footpads were performed just before and 24 hours after the antigen challenging, and swelling (percent increase) of footpad thickness was calculated. Suppression of 300 μg of mHVEM:Fc was statistically significant ($P<0.05$), as shown by the data summarized in FIG. 9.

Example 8

Inhibitory Effect of Mouse HVEM:Fc on Collagen-induced Arthritis in Mice

This example demonstrates that the HVEM:Fc fusion protein of the invention has an inhibitory effect on inflammation in vivo using a art-recognized animal model for arthritis.

Figure 10:
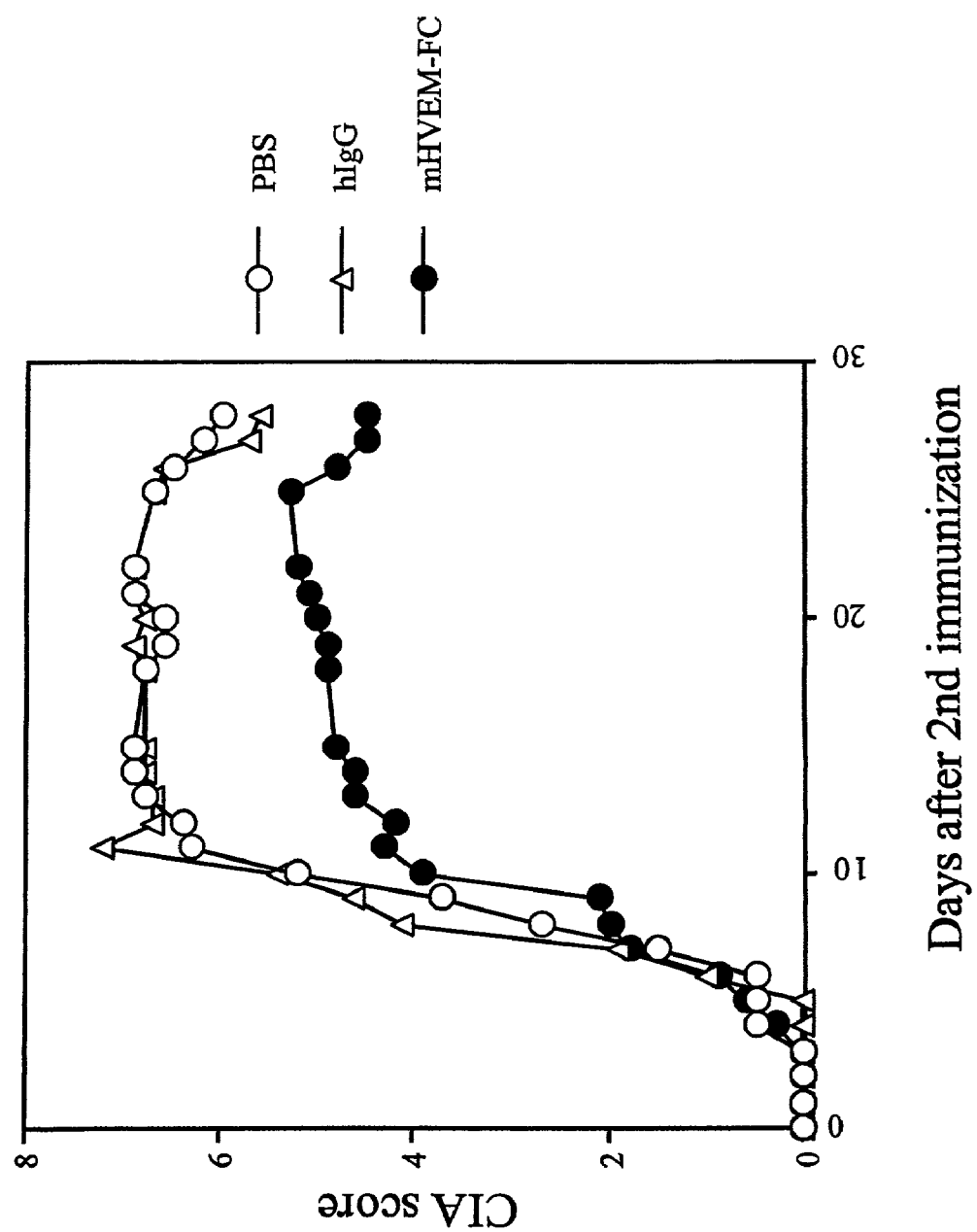
FIG. 10 shows a graph of the CIA score for collagen-induced arthritic mice treated with PBS, hIgG or mHVEM: Fc, see Example 8, below.

Six-week-old DBA/1 mice (Seatec Yoshitomi, Hukuoka, Japan) (N=10) were immunized with emulsions of 100 μg of bovine type II collagen and 100 mg of Mycobacterium tuberculosis (H37Ra) in incomplete Freund's adjuvant at the base of tail by subcutaneous injection, and boosted 28 days later with the same emulsion. Sixty μg of mHVEM:Fc or control IgG was administered intrapertoneally twice a week starting at the second day of immunization. Clinical scoring for each paw was assessed by reference to the following scale: 0=normal, 1=swelling and/or erythema of one toe, 2=swelling and/or erythema of two or more toes, 3=swelling and erythema of the entire paw, 4=complete swelling and erythema of the entire paw and incapacity to bend the ankle. CIA score was expressed as the cumulative value for all paws, with a maximum of 16 (FIG. 10). The data presented in FIG. 10, demonstrate that HVEM:Fc had a significant effect on inflammation of the footpad and ankle.

Example 9

Inhibition of Herpesvirus Infection by Soluble Homotrimeric LIGHT

Figure 12:
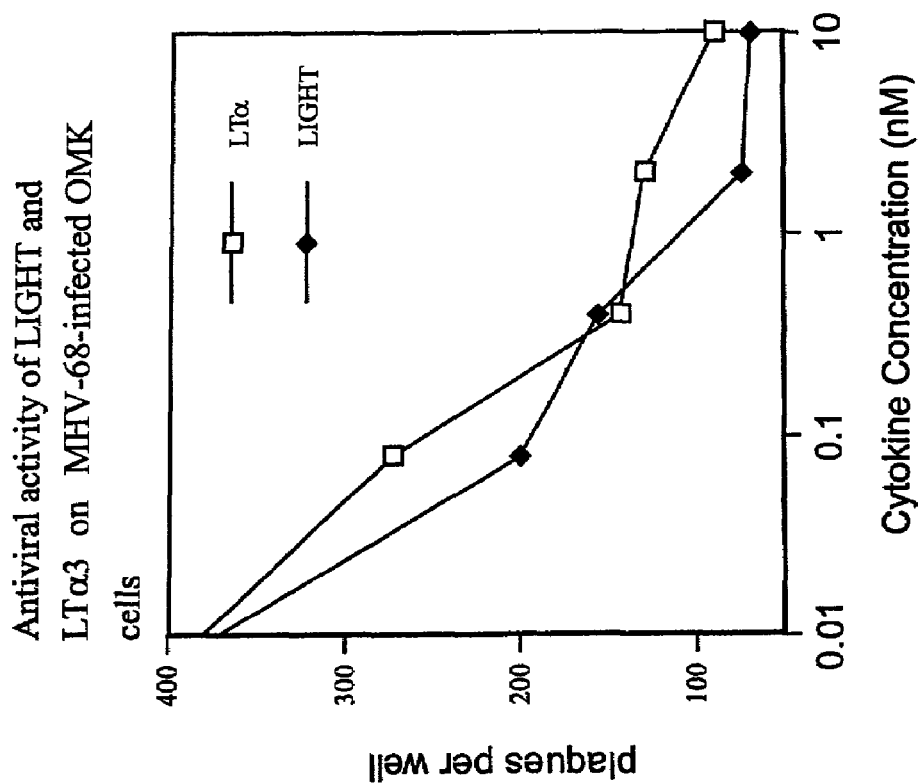
FIG. 12 shows antiviral effect of LIGHT and LTα on γ-herpesvirus, MHV68, in vivo (see Example 9).

This example demonstrates that soluble homotrimeric LIGHT polypeptides of the invention can block the entry of herpesvirus into cells in vivo. It is also demonstrated that the anti-viral activity of LIGHT is by its binding to LTβR and not HVEM. This example also demonstrates that both LIGHT and LTα can prevent virus infection of cells in a dose-dependent manner (FIG. 12).

Herpesviruses have genetic mechanisms that specifically target cytokine systems of the TNF superfamily, suggesting that the immune system has evolved specific counter measures to suppress herpesvirus reactivation or spread in the host.

LIGHT was tested along with other cytokines to determine their ability to inhibit cytomegalovirus (CMV) infection. To investigate the anti-viral and biological properties of LIGHT, a soluble form was made by genetic engineering that deleted the cytoplasmic tail and transmembrane domains. A recombinant soluble form of LIGHT lacking the N-terminal 66 amino acids was produced, as described in detail in Example 12, below, and designated "LIGHTt66." The recombinantly produced soluble LIGHT t66 and its mutants were secreted exclusively as homotrimers (wild type LIGHT of expressed as a homotrimer).

Normal human dermal fibroblasts were infected with the clinical isolate of human CMV (HCMV) Fiala (HCMV-F) or the lab strain AD169 of HCMV at low multiplicity of infection (MOI) of 0.05. Cytokines that signal through either the TNFR1 (Ltα) or the LTβR (LTα1β2, LIGHT) were added to the culture supernatant and incubated for 7 days.

Figure 11:
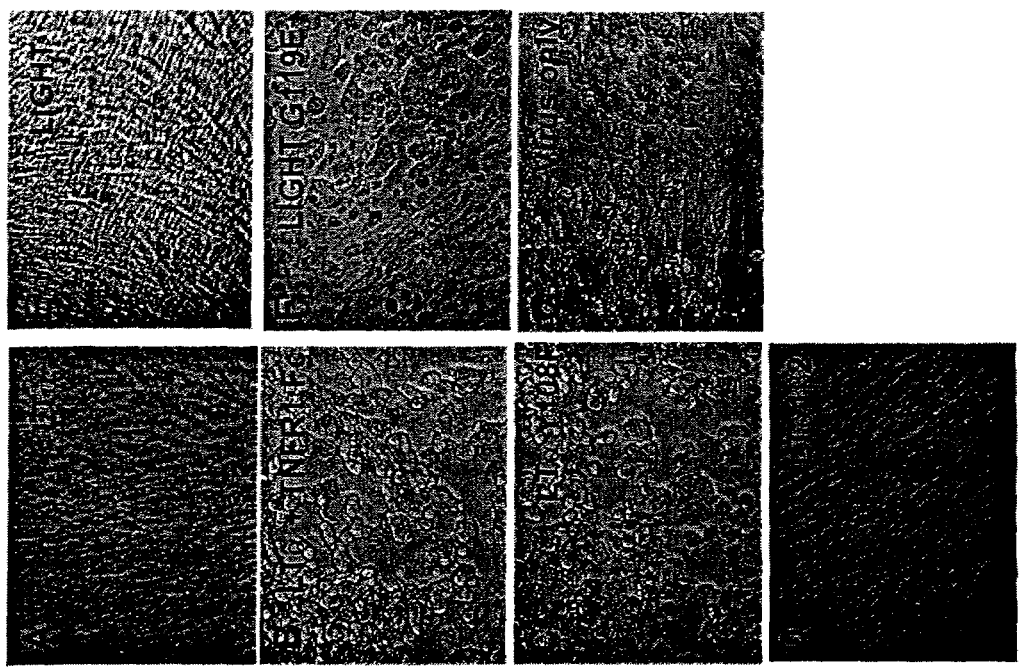
FIG. 11 shows the morphology of dermal fibroblasts infected with HCMV-F at an MOI of 0.05 and cultured in the present or medium with 5 nM of A) LTα, B) LTα+RNFR:Fc, C) LTαY108F, D) LTα1β2, E) LIGHT, F) LIGHT-G119E, and G) Virus only. See Example 9.

Addition of LTα completely blocked viral cytopathic effect (CPE), This inhibition was specific because soluble type I TNFR protein (TNFR:Fc) neutralized the anti-viral effect (FIG. 11A and 11B). Additionally, a point mutant of LTα (Y108F) which can no longer bind to TNFR but retains conformation integrity, was incapable of blocking HCMV spread (FIG. 11C).

LTα1β2 and LIGHT, which both bind to the LTβR, also were able to block viral CPE (FIG. 11D, 11E). A point mutant of LIGHT (G119E), which is incapable of binding to the LTβR, but retains binding to HVEM, was incapable of inhibiting HCMV spread (FIG. 11F). This indicates that the anti-viral activity of LIGHT is likely to be through binding to the LTβR, and not HVEM.

Quantitative analysis of the anti-HCMV activity of LTα, LTα1β2 and LIGHT was accomplished by measuring expression of both the major immediate early protein (IE1) and the late tegument protein pp28 by Western Blot. LTα and LIGHT showed similar relative anti-viral activities, being capable to completely inhibit cytopathic effect of HCMV at a concentration of 100 pM, while LTαβ2 was approximately 10 fold less effective. Monoclonal antibodies specific for the lymphotoxin receptor (LTβR) were also potent inhibitors of HCMV spread.

In addition, studies using mouse γ-herpesvirus showed a reduction in plaque forming units (FIG. 12). Owl monkey kidney cells in 12 well microplates were infected with 500 plaque forming units (PFU) per well for 60 minutes at 37° C. and overlayed with carboxymethycellulose (0.75%) in medium containing fetal bovine serum (FBS) with or without LIGHT or LTα at the indicated concentrations. After 7 days, the cells were fixed with methanol and stained with Gemisa. Each data point in FIG. 12 is the average number of plaques in two wells. The data clearly demonstrates that both LIGHT and LTα were able to significantly decrease the number of infected cells in a dose-dependent manner.

Mouse MHV-68 is similar to the human γ-herpesviruses EBV and HHV-8. EBV is implicated as the oncogenic factor in certain human cancers including EBV-associated lymphoma and nasopharyngeal carcinoma. HHVE is linked to AIDS-associated Kaposi's sarcoma.

Example 10

Biological Activities of Soluble Homotrimeric LIGHT

This example demonstrates that a recombinant, soluble homotrimeric LIGHT polypeptide of the invention is active in several cellular response assays, including apoptosis of adenocarcinomal HT29 cell lines and the induction of ICAM-1 on fibroblasts. As discussed in Example 9, above, to investigate the biological properties of LIGHT, a soluble form, the recombinantly produced soluble LIGHT t66 (described in detail in Example 12), was made. While this soluble polypeptide lacks the cytoplasmic tail and transmembrane domains of wild-type p30, it retains the homotrimeric wild-type tertiary structure.

HT29 cells and 293 cell lines were obtained from ATCC; HT29 cells were derived from human adenocarcinoma, ATCC number HTB-38 (see, e.g., Chen (1987) Cancer Genet. Cytogenet. 27: 125–134). Both cell lines were cultured in DMEM containing 10% FBS with glutamine and penicillin/streptomycin.

Figure 13:
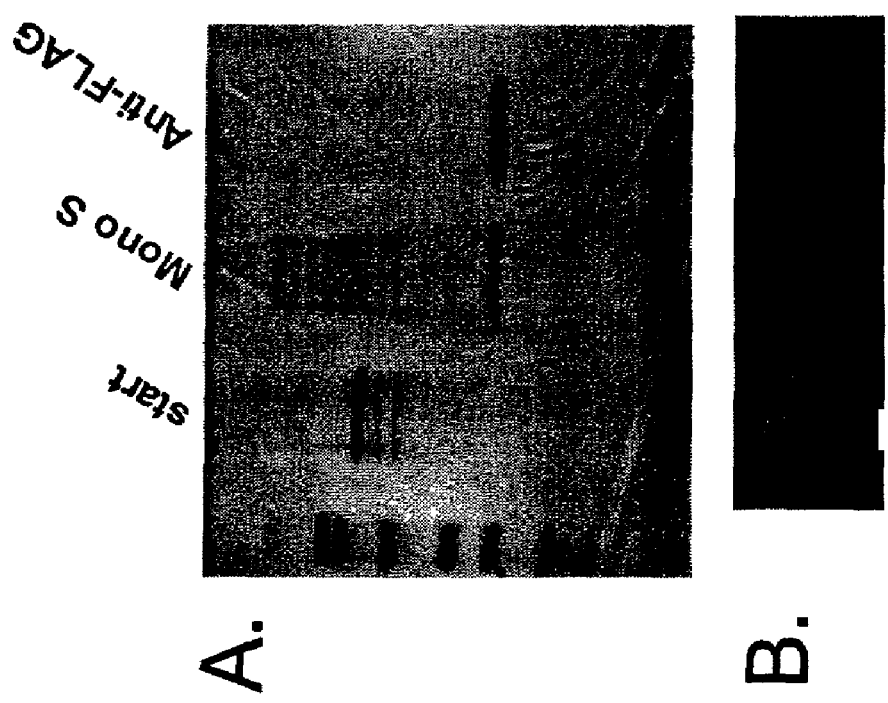
FIG. 13 shows gel demonstrating the purity of LIGHTt66 (A) stained by Coomassie blue or (B) western blotted with anti-FLAG (M2) to detect the recombinant protein. Molecular weight markers are shown in left lane.

293 cells were stably transfected with cDNA encoding human soluble LIGHT polypeptide (see Example 12). Clones with high expression soluble polypeptide were selected for large scale culture. Spent medium from 293-LIGHT cells was harvested for purification by a combination of ion-exchange and affinity chromatography. LIGHT was purified to homogeneity (see FIG. 13), with a yield of 10 to 15 mg per liter and with levels of endotoxin less than 0.1 endotoxin units/mg.

The activity of the purified LIGHT protein was measured by a specific ELISA assay that utilizes soluble forms of LTβR or HVEM in a plate bound form. Recombinant soluble LIGHT (homotrimeric LIGHT t66) binds as efficiently to both mouse HVEM and LTβR as the homologous human forms.

LIGHT is active in several cellular response assays, including apoptosis of HT29 cells and the induction of ICAM-1 on fibroblasts (ICAM is a cell adhesion marker of inflammation). LIGHT is as efficient as LTαβ2 in inducing the death of HT29 cells, but weak compared to the ability of TNF or LTα to induce ICAM-1 expression. The latter result suggests that LIGHT may not be pro-inflammatory. In vivo, LIGHT does not appear to be pro-inflammatory or toxic because mice injected with purified LIGHT (maximum dose tested of 200 μg per mouse) failed to display the symptoms of shock observed when TNF or LTα are administered at this dose.

Example 11

NF-κB, but not TRAF, Necessary for LIGHT-mediated Anti-viral Effect

Figure 14:
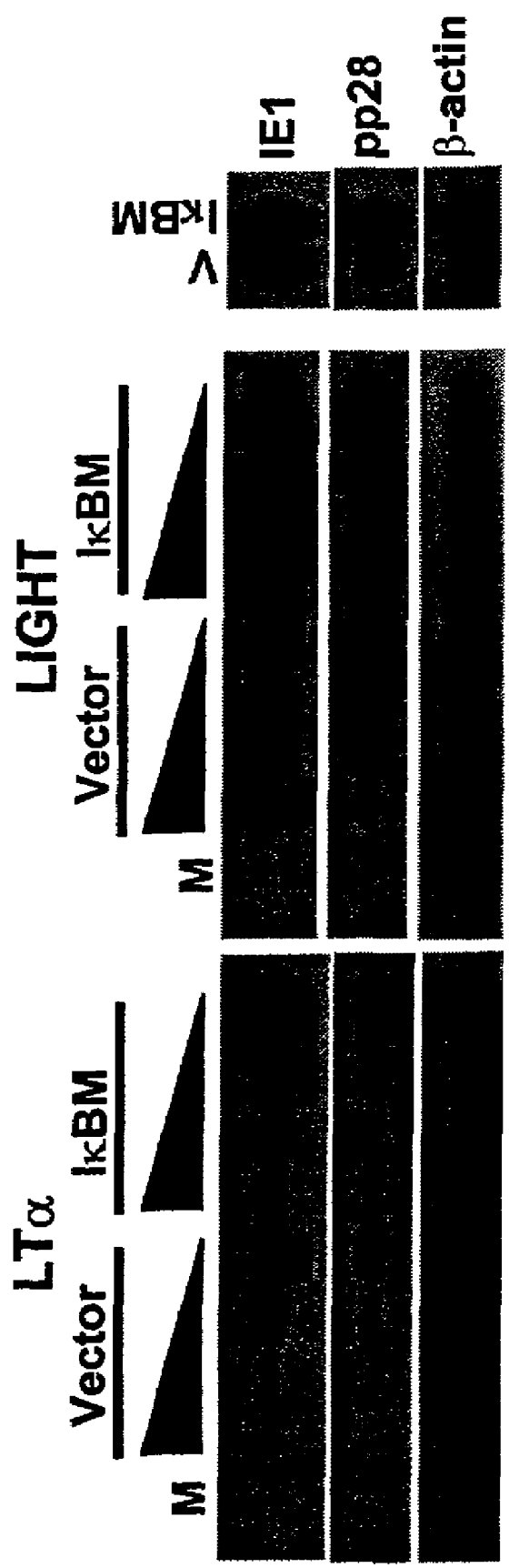
FIG. 14 shows a number of gels demonstrating the Anti-HCMV effect of LIGHT and Lymphotoxins are dependent upon activation of NFκB.

This example demonstrates that the anti-viral activity of soluble, homotrimeric LIGHT and lymphotoxin (LT) requires the activity of NF-κB (cells lacking NF-κB activity were refractory to the effects of LIGHT) (see FIG. 14). Thus, this example demonstrates that activation of NF-κB-activity dependent apoptotic pathways is involved in the anti-CMV activity of LIGHT.

No cell death was observed in normal human dermal fibroblasts (NHDF) treated with LTα, LTα1β2 or LIGHT. This demonstrates that the anti-viral activity of these cytokines may be independent of the apoptotic death pathway that can be triggered by the TNFR. This suggested that an NFκB dependent mechanism may be operative, as this is the other major pathway activated by this receptor. NFκB also controls transcription of several anti-apoptotic proteins in fibroblasts thus counteracting the apoptosis pathway.

To test this hypothesis, a dominant negative mutant of the inhibitor of NF-κBα subunit (IκBαM) was introduced into NHDF by transduction with retroviral vector. This mutant cannot be phosphorylated and thus remains in a stable complex with NFB. This prevents transcription of κB dependent genes. TNF and LTα both failed to induce ICAM-1 expression in NHDF-IκBαM, demonstrating the efficiency (of inhibiting NFκB) of the IκBαM dominant negative mutant.

NHDF-IκBαM cells were then compared to cells transduced with vector alone (NHDF-LXSN) or the ability of the various cytokines to inhibit HCMV replication. It was found that NHDF-IκBαM cells were refractory to the effects of lymphotoxins and LIGHT (FIG. 14). Significantly higher levels of IE1 and pp28 were seen for a given concentration of cytokine in NHDF-IκBαM as compared to NHDF-LXSN cells.

Additionally, a 10 fold increase in infectious HCMV was produced from NHDF-IκBαM cells in the presence of cytokine. Interestingly, HCMV replicated equally well in NHDF-IκBαM as in NHDF-LXSN cells in the absence of cytokine, as assayed by IE1 and pp28 expression and viral titer. This result indicates NF-κB is not essential for efficient viral replication in fibroblasts, although the IE promoter contain multiple NF-κB response elements.

TRAF3 is recruited directly to the LTβR where it is involved in signaling apoptosis, but not in the activation of NFκB. This was demonstrated by dominant negative mutants of TRAF3. TRAF3 dominant negative mutants (TRAF3Δ7 and TRAF3Δ11) introduced into NHDF cells by retrovirus transduction similar to IκBαM, remained sensitive to the anti-virus activity of LIGHT and lymphotoxins. This indicates activation of NFκB-activity dependent apoptotic pathway is not involved in the anti-viral (anti-CMV) activity of soluble LIGHT.

Example 12

Production and Characterization of Soluble (Homotrimeric) LIGHTt66 and LIGHTt66 Point Mutants This example demonstrates the construction and isolation of soluble, recombinant LIGHT polypeptides (used in Examples 9 to 11, 13 and 14), including those with single residue changes (i.e., point mutants), which, as demonstrated below, are secreted as homotrimers.

A recombinant soluble form of LIGHT lacking the N-terminal 66 amino acids was produced (designated LIGHTt66). The truncated, soluble LIGHT was further engineered to include the "FLAG" tag for immuno-affinity purification by anti-FLAG antibody (Sigma, St. Louis, Mo.). The truncated, FLAG-labeled construct was designated LIGHTt66-FLAG.

HT29, and 293 cells were obtained from the American Type Culture Collection (ATCC, Rockville, Md.) and cultured in DMEM containing 10% fetal bovine serum with glutamine and penicillin/streptomycin. Neonatal Normal Human dermal fibroblast (NHDF cells) were purchased from Clonetics, San Diego, Calif. and grown in DMEM supplemented with 10% fetal bovine serum, insulin (5 pg/ml) and fibroblast growth factor (1 pg/ml) (Sigma, St Louis, Mo.).

LIGHTt66-FLAG was produced in stably transfected mammalian (293) cells. Stably transfected 293 cells were grown in roller bottle culture in DMEM containing 0.5 % FBS. Concentration of LIGHT t66 reached 10 mg/l in 7 day cultures. LIGHT t66 was partially purified from 7-day supernatants by an ion-exchange procedure. Supernatant diluted 1:2 in 20 mM Tris, pH 7.0, so that initial NaCl concentration was 50 mM, was loaded on a SP Hitrap™ column (Pharmacia). After washing, LIGHT t66 was eluted using 20 mM Tris/500 mM NaCl, pH 7.0. After dialysis into PBS, LIGHT t66 was further purified by affinity chromatography on a column of monoclonal anti-FLAG (M2) coupled to Affigel™ (Biorad). LIGHT t66 was eluted from the column using 20 mM glycine, 150 mM NaCl, pH 3.0, and neutralized immediately by collection into 50 mM Tris pH 7.4.

Figure 15:
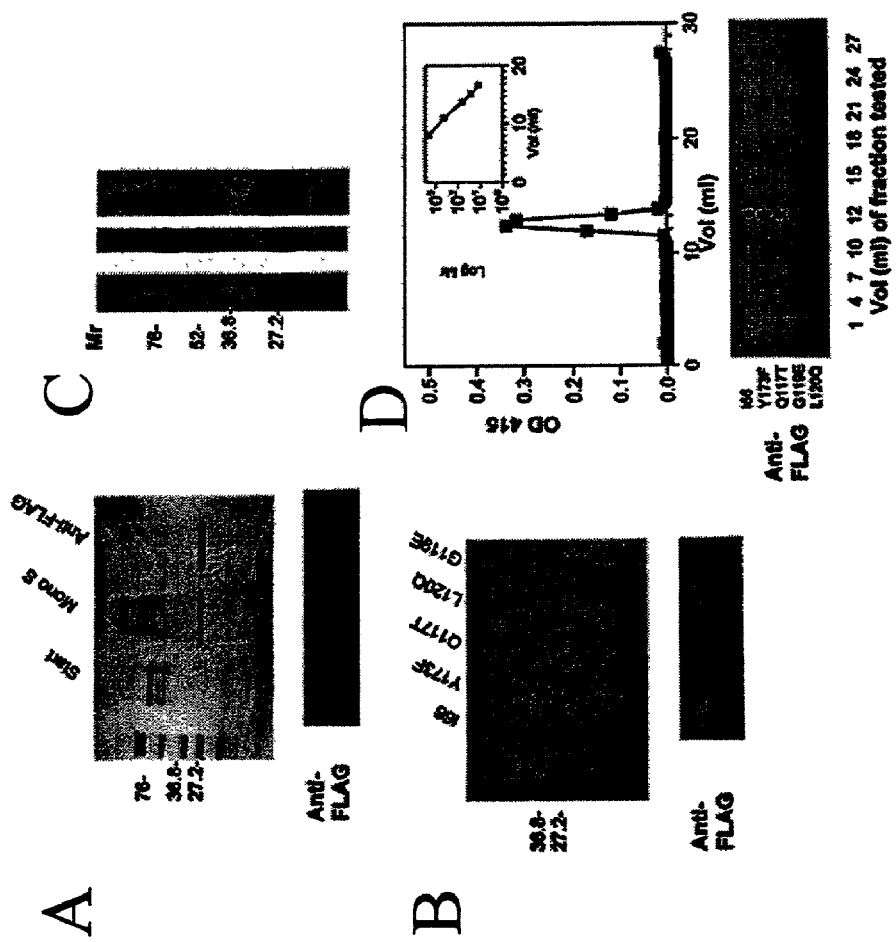
FIG. 15 shows the purification and biochemical characterization of LIGHT t66 and its mutants.

A soluble form of LIGHT (LIGHT t66) with the addition of an N-terminal FLAG epitope was produced in stably transfected 293 cells and purified to homogeneity by ion exchange followed by immuno-affinity purification on an affinity matrix of monoclonal anti-FLAG (M2). Final yield of the protein was 80%and purity >95% (FIG. 15A).

Primer-introduced sequence modification was used to generate soluble LIGHT with the following single amino acid substitutions: G119E, L120Q Q11ITT, and Y173F. Briefly, internal primers were designed to introduce a restriction site at the mutation location. Forward and reverse primers containing the mutations were used in separate PCR reactions to amplify two regions of soluble LIGHT. Primers were as follows:

```
Q117T:
5'_ACGCTGGGCCTGGCCTXCTGA_3',(SEQ. ID. NO. 7)
5'_ACTCTCCCATAACAGCGGCC_3'(SEQ. ID. NO. 8)

G119E:
5'_GAGCTGGCC_ITGCTGAGGGGCCT_3"(SEQ. ID. NO. 9)
5'_CAGCTGAGTCTCCCATAACA_3'(SEQ. ID. NO. 10)

L120Q:
5'_CAGGCC_ITCCTGAGGGGCCTCA_3'(SEQ. ID. NO. 11)
5'_GCCCAGCTGAGTCTCCCATA_3'(SEQ. ID. NO. 12)

Y 173F:
5'_TTCCCCGAGGAGCTGGAGCT_3'(SEQ. ID. NO. 13)
5'_GCGGGGTGTGCGCTTGTAGA_3'(SEQ. ID. NO. 14)
```

The PCR products were ligated at the primer-introduced restriction enzyme site to create soluble LIGHT starting at amino acid t66 and containing one of the 4 amino acid substitutions. The LIGHT t66 mutants were ligated into the FLAG-tagged cassette, pBABE-FLAG which contains the V-cam signal sequence fused to the FLAG epitope. The V-cam FLAG-LIGHT mutant inserts were cloned into pCDNA3.1 (+) (Invitrogen). All mutants were sequenced (ABI310 automated sequencer) for unambiguous verification. For protein production, 293T cells ($1.5 \times 10^6$ cells/10 cm dish) were transfected with 5 pg DNA. Medium containing soluble protein was collected after 24 h in culture.

LIGHTt66-FLAG mutants were purified from 24 h culture supernatant in a one step immunoaffinity procedure using an affinity matrix of monoclonal anti-FLAG antibody (M2) coupled to Affigel™ (5 mg antibody per ml of gel). Culture supernatant (50 to 100 ml) was passed over 0.5 ml of affinity matrix. The gel was washed with 10 volumes PBS and bound protein eluted with 0.5 ml aliquots of 10 mM glycine/HCl, pH 3.0 and neutralized immediately by collection into 50 mM TRIS pH 7.4. Protein-containing fractions were dialyzed against PBS.

Four single amino acid change mutants of FLAG-tagged LIGHT t66-Y173F, G119E, L120Q and Q117T were generated in transiently transfected 293T cells, as described herein. Y173F is the analog of the Y108F mutant of LTα, which lies in the D—E loop. The LTY 108F homotrimer fails to bind receptors. Q117T, G119E and L120Q are three adjacent mutations in the A-A loops, conserved between LTβ and LIGHT, which molecular modeling predicts are involved in receptor binding.

Protein was immuno-affinity purified from culture supernatants in a one-step procedure using monoclonal anti-FLAG (M2)antibody coupled to Affigel (FIG. 15B). Purity for all of the proteins was >95%.

It was next determined that the point mutants trimerized. Analysis by crosslinking and by FPLC gel filtration followed by ELISA and dot blotting of fractions demonstrated that LIGHT t66 and its mutants were secreted exclusively as homotrimers, with no detectable contaminating monomeric or aggregated material (FIG. 15C and D).

ELISAs were used to measure recombinant LIGHTt66 polypeptides (including the point mutations). The capture molecule, murine HVEM:Fc, human HVEM:Fc, murine LTβR:Fc or human LTβR:Fc, was immobilized in wells of a microtiter plate (150 ng/well in 50 µl 20 mM Tris/150 mM NaCl, pH 9.6) for 16 h at 4° C. After washing with PBS/0.5%Tween, samples were applied diluted in PBS/3%BSA and incubated for 1 h at RT. After washing wells were incubated with monoclonal anti-FLAG (M2) (10 µg/ml in PBS/BSA) for 1 h at RT, washed and incubated with goat anti-mouse HRP (1:5000) for 1 hr at RT. After final washing, color was developed with 2,2'-AZINO-bis (3-ETHYL-BENZ-THIAZOLINE-6-SULFONIC ACID) (Sigma). The OD was measured at 415 nm in a SpectraMax plate reader (Molecular Devices Corp., Sunnyvale, Calif.).

Partially purified LIGHT was cross-linked by the addition of bis [2-(succinimidooxycarbonyloxy)ethyl]sulfone (BSO-COES) (Pierce Chemical Co, Rockford, Ill.) at final concentrations of 0.1 and 1 mM, or by addition of glutaraldehyde (0.1% and 1%) for 30 min at 4° C. with rotation. The reaction was stopped by addition of TRIS (20 mM, pH 8.0). Crosslinked and control samples were analyzed by Western blotting using monoclonal M2 (anti-FLAG) antibody.

In order to determine the molecular weight of native LIGHT t66, purified protein was analyzed by gel filtration on a Superose 12™ column using a FPLC 500 system (both from Pharmacia, Piscataway, N.J.). Flow rate was 0.5 ml/min, 0.5 ml fractions were collected, and PBS was the mobile phase. LIGHT in eluted fractions was detected by ELISA. Relative molecular weight of LIGHT t66 was determined by comparison with the elution profiles of calibration proteins.

Example 13

Cytotoxicity Assays Demonstrate that Soluble LIGHT can Trigger Apoptosis on Cells Expressing Lymphotoxin Receptor This example demonstrates that the homotrimeric LIGHT t66 can inhibit growth and cause apoptosis in cells expressing the human LTβR receptor. These data also indicated that crosslinking of HVEM does not induce apoptosis.

HT29 cells (see above), at 5,000/well, were placed in wells of a microtiter plate in DMEM (50 µl) in the presence or absence of IFNγ (80 U/ml). Serial dilutions of LIGHT t66 and other cytokines were added in 50 µl medium, again in the presence or absence of IFNγ, and the cells were incubated at 37° C. After 24 to 72 h, 20 pl of 5 mg/ml MTT [3-(4,5-dimethylthiazol-2-yl) 2,5 diphenyltetrazolium bromide] was added and the plate incubated for 4 h at 37° C. The medium was then aspirated and 100 µl acidified 70% isopropanol added to dissolve the formazin. The OD was quantified at 570 nm.

Figure 16:
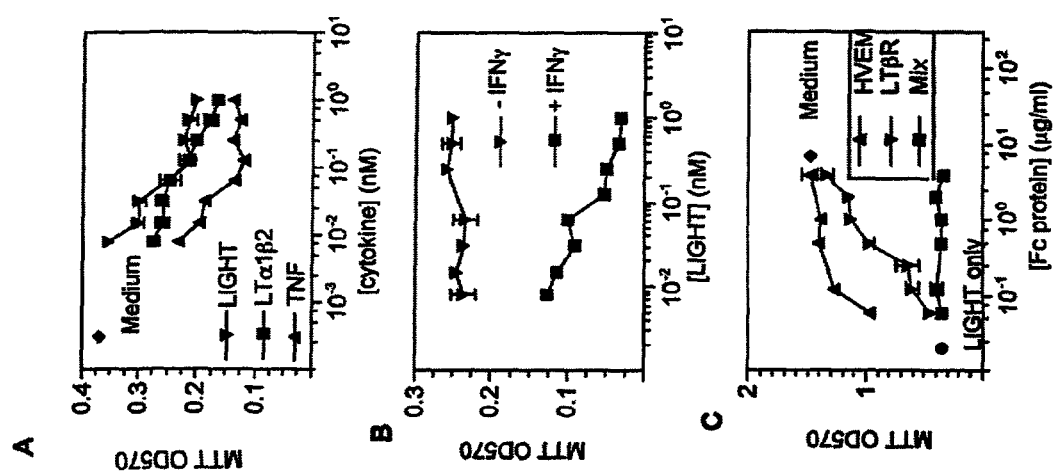
FIG. 16 shows graphs demonstrating that LIGHT t66 is cytotoxic to HT29 cells.

LIGHT t66 inhibited growth and caused apoptosis of HT29 cells with comparable efficiency to LTα1β2 (FIG. 16A). Cytotoxicity was dependent on IFNγ (FIG. 16B) and was maximal after 72 h. Over a range of experiments, 50% cytotoxicity was achieved with doses of 10 to 100 pM. LIGHT t66 cytotoxicity could be blocked by pre-incubation of LIGHT t66 with human LTβR:Fc or HVEM:Fc in a dose-dependent manner; whereas Fas:Fc, which does not bind LIGHT, had no effect (FIG. 16C).

Figure 19:
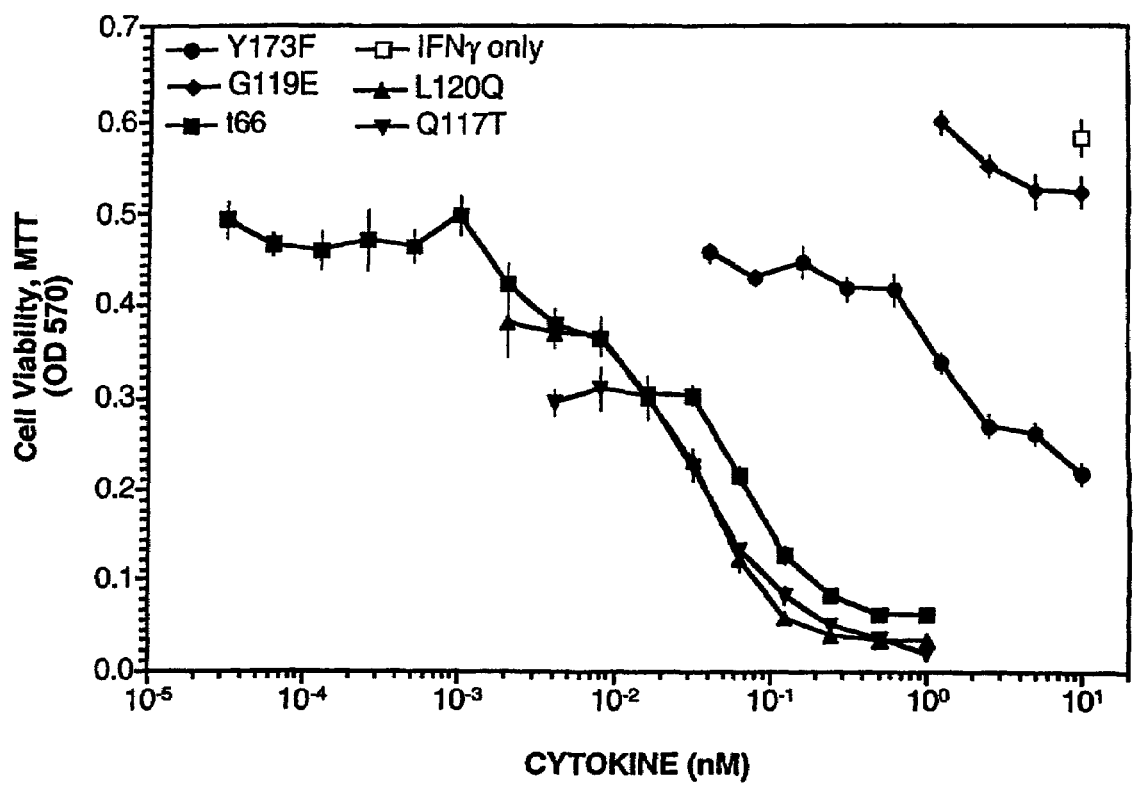
FIG. 19 shows cell cytotoxicity of LIGHT t66 mutants in HT29 cells. HT29 cells were incubated with serial dilutions of LIGHT t66 and its mutants in the presence of IFNγ, an MTT assay was performed after 72 h. L12OQ and Q117T were toxic to HT29 cells with comparable efficiency to LIGHT t66 (50% cell death at 10 µM cytokine). Y173F was weakly cytotoxic (50%cell death at 1 nM cytokine). G199E showed negligible cytotoxicity to these cells.

In the presence of IFNγ, L120Q and Q117T were cytotoxic to HT29 cells with comparable efficiency to LIGHT t66 (FIG. 19). Y173F, which binds both hu LTβR and hu HVEM, showed weaker, but significant cytotoxicity to these cells, whereas G119E, which has higher affinity for HVEM than Y173F, but fails to bind LTβR, showed no significant cytotoxicity.

The data obtained with the LIGHT t66 mutants strongly suggested that LIGHT-mediated apoptosis of HT29 cells is mediated via LTβR. To confirm this hypothesis, and to determine whether LIGHT-mediated cross-linking of HVEM potentiates or inhibits LTβR-mediated apoptosis, we conducted experiments using a panel of monoclonal and polyclonal anti-HVEM and anti-LTβR antibodies.

In addition to goat polyclonal HVEM IgG and goat polyclonal LTβR IgG, two mouse monoclonal anti-HVEM antibodies, CW1 and CW8, and two mouse monoclonal anti-LTβR antibodies, BDA8 and CDH10 were used. All bound to the appropriate receptor on the surface of HT29 cells (FIG. 20A). The anti-HVEM antibodies CW1 and CW8 were used on the basis of ELISA blocking studies in which CW8 inhibited binding of LIGHT to huHVEM, as did polyclonal goat anti-HVEM, whereas CW1 had no effect on binding (FIG. 20B).

Because monoclonal anti-LTβR antibody BDA8 has been shown to inhibit LTα1β2-mediated apoptosis of HT29 cells, whereas CDH10 has been shown to enhance this effect, it was investigated whether these antibodies might affect LIGHT-mediated apoptosis in the same way. In ELISA blocking studies, polyclonal goat anti-LTβR and BDA8 inhibited binding of LIGHT to LTβR, whereas CDH10 had no effect on binding (FIG. 20C).

Goat polyclonal anti-LTβR induced slow apoptotic death of HT29 cells in the presence of IFNγ (FIG. 20D), whereas goat polyclonal anti-HVEM did not affect cell viability. This suggests that cross-linking of HVEM does not induce apoptosis in this cell line.

Further, polyclonal anti-HVEM neither enhanced nor inhibited polyclonal anti-LTβR-dependent cell death (FIG. 20D). Pre-incubation with polyclonal goat anti-LTβR markedly enhanced the sensitivity of HT29 cells to LIGHT-mediated killing (FIG. 20E).

DH10, which enhances killing by LTα1β2, also enhanced susceptibility of the cells to LIGHT, whereas pre-incubation with BDA8, which inhibits killing by LTα1β2, resulted in reduced LIGHT-mediated cytotoxicity (FIG. 20E). Pre-incubation of the cells with polyclonal goat anti-HVEM or with the monoclonal anti-HVEM antibodies CW1 and CW8 had no effect on their susceptibility to killing by LIGHT.

Collectively, these data indicate that crosslinking of HVEM did not induce apoptosis, that HVEM signaling did not synergize with LTβR signaling in induction of apoptosis, and that HVEM signaling did not trigger protective events sufficient to interfere with the LTβR dependent apoptotic pathway.

Example 14

Figure 17:
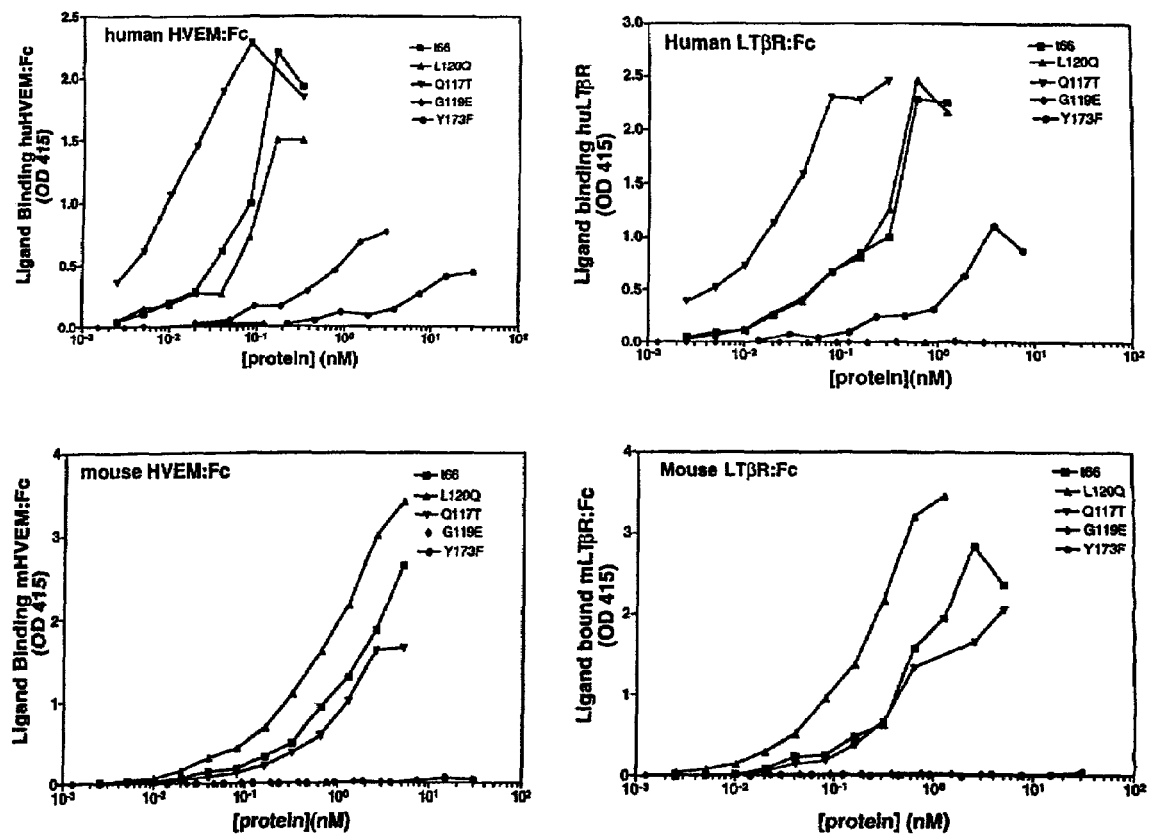
FIG. 17 are graphs showing the receptor binding characteristics of LIGHT t66 and its mutants. LIGHTt66-FLAG and mutants were analyzed by ELISA using the stated receptors as capture molecule and M2 anti-FLAG as detecting antibodies. L120Q and Q117T bound human HVEM and LTβR with affinity comparable to or greater than LIGHT t66. G119E bound human HVEM:Fc with reduced affinity and showed no detectable binding for human LTβR:Fc. Y173F bound human LTβR with reduced affinity and bound G119E weakly. L12OQ showed enhanced affinity for murine HVEM:Fc and LTβR:Fc. Binding of G119E and Y173F to murine receptors was not detected in this system.

Binding Studies of Soluble, Homotrimeric Human LIGHT to LTβR and HVEM by ELISA and Surface Plasmon Resonance Association and dissociation rates of the interaction of LIGHT t66 (a soluble, homotrimeric p30) and LIGHT t66 mutants (described above) with human HVEM: Fc and LTβR: Fc were determined by surface plasmon resonance. Receptor binding characteristics were investigated by ELISA using human (hu) and murine (mu) LTβR:Fc and HVEM: Fc constructs as capture molecules and M2 anti-FLAG antibody for detection (FIG. 17).

G119E showed no detectable binding to huLTβR: Fc and its affinity for huHVEM:Fc was approximately 30-fold lower than that of LIGHT t66 (KD=114 nM). The reduction in affinity of G119E for huHVEM:Fc was due to an increase in dissociation rate (kd=2.0±0.4×10$^{-3}$s$^{-1}$) Y173F bound both huLTβR:Fc and hu HVEM:Fc with reduced affinity, again due to increased dissociation rates. Affinity of Y173F for huLT8R (kD=31 nM) was 3 to 4 fold lower than that of LIGHT t66, while affinity of Y173F for huHVEM:Fc was more than 40-fold lower (kD=180 nM).

Q117T bound both huHVEM:Fc and huLTβR:Fc with similar association rates to LIGHT t66, and slower dissociation rates, so that affinity of this mutant for the receptors was increased relative to LIGHT t66.

TABLE 1

| | Hu HVEM:Fc | | | HuLTβR:Fc | | |
|---|---|---|---|---|---|---|
| | ka (M$^{-1}$s$^{-1}$) | kd (s$^{-1}$) | kD (nM) | ka (M$^{-1}$s$^{-1}$) | kd (s$^{-1}$) | kD (nM) |
| LIGHT t66 | 1.2 ± 0.2 × 10$^4$ | 4.8 ± 5.1 × 10$^{-5}$ | 3.9 ± 3.9 | 2.7 ± 0.5 × 10$^4$ | 1.2 ± 0.2 × 10$^{-4}$ | 4.5 ± 0.7 |
| Q117T | 2.0 ± 0.7 × 10$^4$ | 5.0 ± 4.5 × 10$^6$ | 0.3 ± 0.3 | 3.2 ± 0.7 × 10$^{-4}$ | 4.5 ± 1.2 × 10$^{-5}$ | 1.5 ± 0.7 |
| G119E | 1.8 ± 0.4 × 10$^4$ | 2.0 ± 0.4 × 10$^{-3}$ | 114 ± 14 | | No Binding | |
| Y173F | 1.9 ± 0.2 × 10$^4$ | 3.3 ± 0.1 × 10$^{-3}$ | 173 ± 30 | 3.7 ± 0.8 × 10$^4$ | 1.1 ± 0.4 × 10$^{-3}$ | 31 ± 8 |

The capture molecule, human HVEM: Fc and LTβR: Fc, (50 μg/ml) was coupled to a CM5 sensor chip of a BIA-core 1000™ (BIAcore Inc., Piscataway, N.J.) by amine coupling at pH 5.0. The sensor surface was equilibrated with PBS (20 mM sodium phosphate/150 mM NaCl, pH 7.4) and sensorgrams were collected at 25° C. and a flow rate of 5 μl/min. A 10 μl injection of LIGHT t66 or mutant was passed over the sensor surface; after the association phase 800 seconds of dissociation data were collected. The sensor surface was regenerated after each cycle with a 10 μl pulse of 10 mM glycine pH 2.0. Sets of 5 analyte concentrations, 100 to 500 nM were collected, and analyzed by nonlinear regression using the BIIAevaluation software (2.1)™. Association and dissociation data were fitted on the basis of the simple AB⇌A+B model.

LIGHT t66 bound hu HVEM:Fc and huLTβR:Fc with comparable affinity. LIGHT t66 bound muHVEM:Fc and muLTβR:Fc with tenfold lower affinity. The LIGHT 30 t66 mutants L120Q and Q117T bound huHVEM:Fc and huLTβR:Fc with comparable affinity to LIGHT t66. Interestingly, L120Q showed enhanced affinity for both murine receptors. G119E showed reduced but significant affinity for hu HVEM and undetectable binding to hu LTβR, while Y173F had reduced but significant binding to both hu LTβR and hu HVEM. G119E and Y 173F did not bind the murine receptors.

Figure 18:
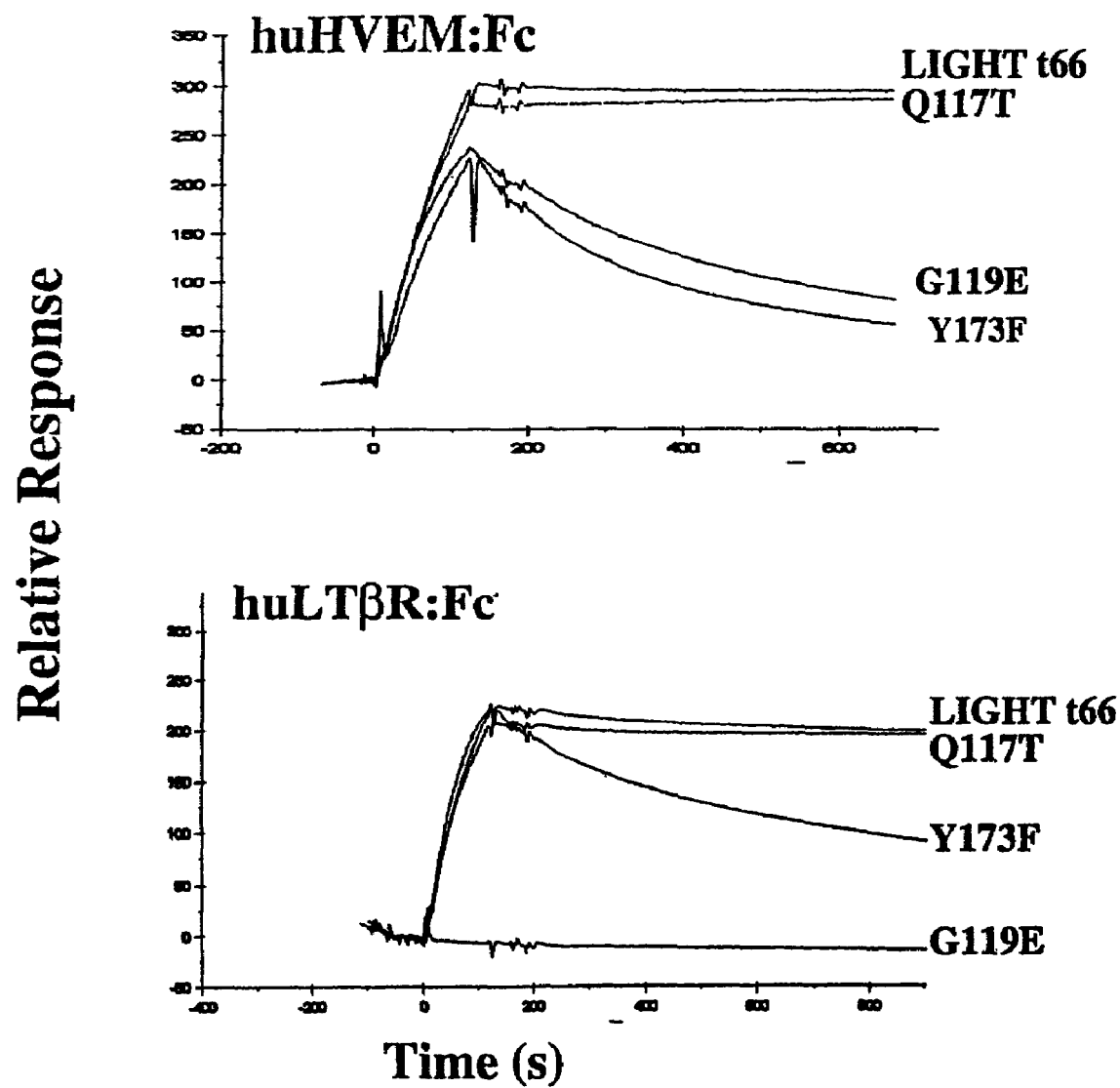
FIG. 18 shows overlays of sensorgrams demonstrating surface plasmon resonance. Overlays of sensorgrams for binding of LIGHT t66 and its mutants to huHVEM:Fc and huLTβR:Fc at ligand concentration 300 nM. Kinetics of binding were similar for LIGHT t66 and Q117T. G119E and Y173F dissociated from HVEM:Fc with increased off rates relative to LIGHT-t66. Y173F dissociated from huLTβR with an increased off rate, whereas G119E failed to bind this receptor.

Analysis of binding of LIGHT t66 and its mutants to huLTβR:Fc and hu HVEM:Fc by surface plasmon resonance confirmed and extended the data obtained by ELISA (FIG. 18). Results are summarized in Table 1. Association and dissociation phases for interaction of LIGHT t66 with both receptors fitted well with the simple A+B⇌AB model, with ka=2.7±0.5×10$^4$ (M/s)for hu LTβR:Fc and 1.2±0.2×10$^4$ (M/s)for huHVEM:Fc, and kd s=1.2±0.2×10$^{-4}$ and 4.8±5.1× 10$^{-5}$s$^{-1}$ hu LTβR:Fc and huHVEM:Fc, respectively. The intrinsic dissociation rate constants (kD), calculated from the ratio kd/ka, were 4.5±0.7 nM for huLTβR:Fc and 3.9±3.9 nM for huHVEM:Fc (these data are the means of 5 measurements over a concentration range 100 to 500 nM LIGHT t66).

Example 15

Upregulation of ICAM by Soluble, Homotrimeric Human LIGHT is Mediated by LTβR

This example demonstrates that soluble, homotrimeric LIGHT and two variations (point mutations at L120Q and Q117T) can up-regulate ICAM expression.

NHDF cells were used at passage 5 or earlier. Cells (180,000/4.2 cm$^2$ dish) were incubated with cytokine in complete DMEM (600 μl/well) supplemented with insulin and fibroblast growth factor. After 36 h cells were stained with a monoclonal anti-ICAM (P2A4; 10 μg/ml) followed by a goat anti-mouse IgG-PE and analyzed by flow cytometry.

L120Q and Q117T (5 nM) induced up-regulation of ICAM expression by NHDF cells to levels comparable to those achieved using LIGHT t66 (4-fold induction) (FIG. 21). When used at 5 nM Y173F caused a slight induction of ICAM expression, whereas at 20 nM induction was 2.5-fold. At 5 nM G119E caused no detectable induction of ICAM expression and slight induction (<1.5-fold) at 20 nM.

Example 16

HVEM Co-localizes with TRAF2 and TRAF5, but not TRAF3 on the Cell Membrane

This example demonstrates that HVEM, when co-expressed as a recombinant protein in 293 cells with TRAF polypeptides, co-localized and bound to TRAF2 and TRAF5 (but not TRAF3) on the cell membrane.

In co-transfection experiments in 293 cells, it was demonstrated (using confocal immunofluorescence microscopy) that HVEM co-localized with TRAFs 2 and 5, but not with TRAF 3. LTβR co-localized with all three TRAFs examined; negative control was co-transfection with the empty vector pBabe. FLAG-tagged TRAFs were visualized with FITC. LTβR and HVEM were visualized using Texas Red. Co-localized proteins appeared yellow. HVEM co-localized with TRAFs 2 and 5, but not TRAF3. LTβR co-localized with TRAFs 2,3, and 5.

It was also demonstrated that HVEM bound to TRAF2 and TRAF5 by experiments where immunoprecipitation of the recombinantly expressed HVEM (by anti-HVEM antibody) co-precipitated TRAFs 2 and 5, but not TRAF3 (from lysates of the transfected 293 cells). LTβR precipitated only TRAF 3. See FIGS. 22A, and 22B.

Confocal Immunofluorescence Microscopy Procedures

Twenty four hours post transfection 293T cells were seeded in 8 well Lab-TekB™ chamber Sides (Lab-Tek catalogue number 177445) at $3 \times 10^4$ cells/well and cultured for 18 to 36 hours at 37° C. and 5% $CO_2$. For staining, wells were washed two times with PBS, fixed for 10 minutes at room temperature in freshly prepared 2% paraformaldehyde in PBS pH 7.0, washed again two times with PBS, and then permeabilized in methanol for 2 minutes at room temperature. Cells were washed in PBS, then blocked for a minimum of 10 minutes at room temperature in PBS containing 3% BSA. Polyclonal goat anti-LTβR was diluted to a final concentration of 20 µg/ml, polyclonal rat anti-HVEM was diluted to a final concentration of 20 µg/ml and mouse monoclonal anti-FLAG, M2 (Sigma F3165), was diluted to a final concentration of 5 µg/ml. Antibodies were diluted in PBS, 3% BSA and 0.2% Triton X 100 (PBS/BSA/Triton). Primary antibodies were added to the wells for a final volume of 120 µl/well and incubated in a humidified chamber at room temperature for 1 hour. Wells were then washed three times in PBS/BSA/Triton. FITC conjugated donkey anti mouse antibodies in combination with Texas Red conjugated donkey anti goat antibodies (both from Jackson Immuno-Research Laboratories), or Texas Red conjugated donkey anti rabbit antibodies (Jackson immuno Research Laboratories), were diluted to a final concentration of 1:200 in PBS/BSA/Triton in a final volume of 120 µl/well. Slides were incubated in a humidified chamber at room temperature in the dark for one hour and then washed three times in PBS/BSA/Triton and the wells removed. Four microliters per well of a mounting solution made of 80% glycerol in PBS was added over the cells of each well and the slides were covered with a 24×55 microscope cover glass (Fisherbrand #12–544–18). Slides were kept at 4° C. in the dark for 1 to 7 days before visualization.

Cells were observed using a BioRad MRC-1024™ confocal microscope with a Krypton/Argon ion Laser and a 60X Nikon™ objective. Images were acquired using the LaserSharp™ operation system and were analyzed and manipulated in Adobe Photoshop 5.0™.

HT29 cells ($10^6$/ml in DMEM/3% BSA) were stained with mouse monoclonal anti-HVEM or anti-LTβR antibody for 30 min at 4° C. followed by goat anti-mouse IgG coupled to phycoerythrin (PE) for 30 min at 4° C. and analyzed by flow cytometry using a FACSCAN (Becton Dickinson, Mountain View, Calif.).

Example 17

Inhibition of HCMV by Lymphotoxins and LIGHT

This example describes data demonstrating that human CMV is inhibited by lymphotoxins LTα and LTα1β2 and LIGHT.

NHDF were seeded into 96 well plates at $1 \times 10^4$ cells/well or $1.5 \times 10^5$ cells in 12 well plates and infected the following day with HCMV (MOI=0.01). Virus was allowed to adsorb for 2 hours at 37° C., cells were then washed twice and cultured in medium with the indicated reagents. For analysis of virus production and protein expression, 12 well cultures were harvested and centrifuged to collect the cell pellet for protein analysis by western blotting as described (Benedict et al., (1999) J. Immunol. 126:6967), and the supernatant was assayed for infectious virus by plaque assay. To control for equal protein loading, the blots were reprobed with an antibody to human β-actin (MAB810, Chemicon, Temecula, Calif.).

The replication cycle of HCMV in normal human diploid fibroblasts (NHDF) reaches completion after ~72 hours. At a low multiplicity of infection (MOI≦0.1), HCMV infection appears in focal areas of cytopathicity typified by cell rounding and detachment, that spreads throughout the culture by day 6–7 (FIG. 23a). The addition of LTα, LTα1β2 or LIGHT to the cultures completely inhibited the cytopathic effect of HCMV (FIG. 23b,e,g).

The anti-HCMV activity of LTα was neutralized when excess soluble decoy receptor, TNFR1-Fc was added (FIG. 23c). Further, point mutations in LTα (LTαY108F) (Williams-Abbott et al. (1997) J. Biol. Chem. 272:19451) or LIGHT (G119E) (Rooney et al., (2000) J. Biol. Chem. 275:14307), mutations that disrupt binding to their specific receptors TNFR1 and LTβR, abolished the inhibitory action of these cytokines (FIG. 23d,f). Cytokine mediated inhibition was equivalent whether added at the time of virus infection or several hours after virus adsorption, indicating that the cytokines did not disrupt cell attachment or entry of HCMV.

To assess the effect of LTα, LTα1β2 and LIGHT on HCMV protein expression, both the major immediate early protein (IE1/pp72) and the late tegument protein pp28 were analyzed by western blot (FIG. 24a). LTα1β2 and LIGHT showed similar relative anti-viral activity (IC50 for inhibition of pp28 expression of ~1 and 0.4 nM respectively), while LTα was ≧40 fold more effective (IC50~0.01 nM, FIG. 24b), which is consistent with the higher receptor-binding affinity of secreted LTα compared with the normally membrane anchored LTα1β2 and LIGHT (Rooney et al., (2000) J. Biol. Chem. 275:14307).

Activation of the LTβR via addition of an agonistic polyclonal IgG elicited the inhibitory effect on HCMV protein expression (FIG. 24a,b), indicating that this receptor mediated the anti-viral effect seen with LTα1β2 and LIGHT. Similarly, the agonistic anti-TNFR1 mAb, H398, inhibited HCMV replication. Consistent with reduction in cytopathicity and viral protein expression mediated by these cytokines, production of infectious virus was also significantly reduced (FIG. 24c).

Obvious cell death was not detected in NHDF treated with lymphotoxins whether infected with HCMV or not. Dermal fibroblasts express receptors for FasL and TRAIL, and in the presence of cycloheximide undergo apoptosis following treatment with pM levels of ligand. Surprisingly, FasL and TRAIL were unable to reduce virus production (FIG. 24c), or inhibit virus protein expression and cytopathicity indicating the antiviral effect is specific to LIGHT and lymphotoxins in this model. Together, these results suggested that the mechanism of blocking virus spread was probably not by inducing death of infected cells.

Example 18

Non-apoptotic and Reversible Effect of Lymphotoxin and LIGHT on HCMV Replication This example describes data demonstrating that anti-viral effect of lymphotoxins and LIGHT is reversible, does not involve death of virus-infected cells and occurs late in the viral replication cycle.

Although cell death or cytopathic effects were not observed in HCMV-infected fibroblasts treated with lymphotoxins or LIGHT, some expression of immediate early protein 1 (IE1) was always detectable 7 days post-infection (FIG. 24a and 25a), even at high concentrations of cytokine that completely block infectious virus production (FIG. 25b). This suggested that receptor signaling may block viral spread by inhibiting gene expression downstream of the immediate early genes. If this is the case, cytokine treated cells may harbor HCMV genome in a restricted expression state.

To test this hypothesis, NHDF infected with HCMV and treated with LTα for 7 days were washed and then supplemented with medium without cytokine for an additional 7 days. Immediate early protein 1 (IE1/pp72) and viral glycoproteins gB and gH (early and early-late expressed genes, respectively) (Chambers et al., (1999) J. Virol. 73:5757) could be detected by western blot during the initial 7 days of infection in the presence of LTα, when no cytopathicity or virus production was seen. However, expression of the true late protein pp28 (Kerry et al., (1997) J. Virol. 71:981) was undetectable (FIG. 25a). This level of protein most likely represents expression in cells initially infected at low MOI. A vigorous reemergence of viral protein expression (FIG. 25a) with high levels of pp28, concurrent with the release of infectious virions (FIG. 25b), occurred after this initial 7 day period when the culture was replaced with fresh medium lacking cytokine. Thus, the block to HCMV appears to be late in the replication cycle based on Western blot analysis of these representative viral proteins and the short lag-time before cytopathicity (~24 hours) and appearance of virus in the culture supernatant (~48 hours) after removal of cytokine. LTα1β2, anti-LTβR antibodies and LIGHT similarly inhibited HCMV. Together, these results demonstrate that the anti-viral effect of lymphotoxins and LIGHT is reversible and does not involve death of virus-infected cells.

Example 19

NFKB but not TRAF3 or FADD is Necessary for Lymphotoxin and LIGHT Anti-HCMV Activity This example describes data demonstrating that anti-HCMV activity of TNFR1 and LTβR requires activation of NFkB.

LTβR and TNFR1 are capable of activating both apoptotic and non-apoptotic signaling pathways that can be distinguished by introducing dominant negative (dn) mutants of key signaling molecules. Mutant signaling molecules were introduced into NHDF with retroviral vectors containing dominant acting forms of IκBα, TRAF3, FADD, or a control empty vector (LXSN). The IκBα mutant (IκBαM) contains two point mutations at serine 32 and 36 to alanine that deletes critical phosphorylation sites targeted by cytokine-activated serine kinases (Van Antwerp et al., (1996) Science 274:787). When introduced into NHDF, IκBαM protein cannot be phosphorylated and degraded by the ubiquitination pathway, thus retaining NFκB in its latent cytoplasmic state, which in turn prevents nuclear translocation and transcriptional activation of NFκB target genes, such as ICAM1 (FIG. 26a). The TRAF3 dn mutant can inhibit LTβR induced death in HT29 carcinoma cells, but not NFκB activation (Force et al. (2000) J. Biol. Chem. 275:11121; Rooney et al. (2000) J. Biol. Chem. 275:14307). The FADD dn mutant has the death effector domain required for caspase 8 recruitment to TNFR1 and Fas deleted.

Stable expression of IκBαM(S32,36A), TRAF3.D11 and FADD.dn were generated by transduction with replication incompetent retroviral vectors. Retroviral vectors were produced by a three plasmid $CaPO_4$ transfection method into 293T cells as described (Force et al. (1997) J. Biol. Chem. 272:30835). The retroviral vector expression plasmids LXSN, IκBαM (a dominant negative mutant of IκBα cloned into LXSN (Van Antwerp et al., (1996) Science 274:787), and TRAF3.D11 dominant negative acting mutants inserted into pBABE retroviral vector have been described (Force et al., (1997) Proc. Natl. Acad. Sci. 94:2460). The pBABE-FADD.dn retroviral vector was generated from a plasmid containing full length FADD (gift of V. Dixit) by PCR amplification of a truncated FADD coding sequence lacking an intact death effector domain (nucleotide 240–627) with the addition of a 5' SnaB I site and a 3' EcoR I site. After amplification, the PCR product was digested, ligated into pBABE-FLAG (pBABE-puro containing an N-terminal FLAG epitope tag inserted at the BamH I/SnaB I site) and verified by DNA sequencing (ABI Prism 310 Perkin-Elmer, Foster City, Calif.). Retroviral vector transduction frequency was greater than 99% as gauged by resistance of cells to drug selection.

IκBαM expressing fibroblasts, when compared to control vector transduced cells, were refractory to the anti-viral effects of lymphotoxins and LIGHT as detected by viral protein expression (FIG. 26b) or virus production (FIG. 26c). IκBαM did not significantly alter HCMV replication in the absence of cytokine. By contrast, the TRAF3 dn mutant did not block the antiviral effect of either LTα1β2 or LIGHT. Surprisingly, the FADD dn mutant actually enhanced the effect of LTα, but also partially diminished virus replication in the absence of cytokine. These results demonstrate that anti-HCMV signaling mediated by both TNFR1 and LTβR requires activation of NFκB and confirm that inhibition of HCMV replication does not involve apoptosis of infected cells.

Example 20

Interferonβ Mediates Lymphotoxin and LIGHT Dependent Antiviral Activity

This example demonstrates that IFNβ mediates the anti-viral activity of lymphotoxins and LIGHT. This example also demonstrates that the level of IFNβ induction needed to mediate anti-viral activity (e.g., inhibit CMV replication) is greater than that produced by virus alone.

Supernatant from LTα treated HCMV infected fibroblasts, but not from cells treated with LTα or virus alone was capable of transferring antiviral activity to newly infected cells (FIG. 27a). However, neutralization of LTα in these supernatants by TNFR1-Fc failed to block the antiviral activity as measured by IE1 protein expression (FIG. 27a). This result suggested that a secondary mediator was responsible for the antiviral activity induced by lymphotoxins.

Neutralizing antibodies to IFNβ added to the medium along with TNFR1-FC ablated the transfer of antiviral activity, implicating type I interferon (FIG. 27a). Inclusion of anti-IFNβ neutralizing antibodies upon initial treatment of HCMV infected cells with LTα also reversed the block to viral gene expression (FIG. 27b) and virion production (FIG. 27c). Anti-IFNα showed minimal (<5% compared to anti-IFNβ) but consistent neutralizing activity; anti-IFNα was without effect (FIG. 27b). Additionally, anti-IFNβ was able to block the antiviral activity of LIGHT or LTβR agonistic antibodies indicating that a similar signaling mechanism is initiated by both LTβR and TNFR1.

For analysis of IFNα/β mRNA induction by RT-PCR, NHDF (~80% confluent) were harvested 4 hours after infection and total RNA was isolated (Rneasy mini kit, Qiagen). RNA was treated with DNAse I, and 2 mg was used for reverse transcription. For PCR analysis, volumes of RT reactions and cycles of PCR were determined empirically to ensure analysis was within the linear range. Primer sequences used for PCR were: βactin, 5'-tgacggggtcaccca-cactgtgcccatcta-3'(SEQ. ID. NO. 15) and 5'-ctagaagcatttgcg-gtggacgatggag-3'(SEQ. ID. NO. 16); IFNβ, 5'-gtcagtgtca-gaagctcctgtggc-3'(SEQ. ID. NO. 17) and 5'-ctatggtccaggcacagtgactg-3'(SEQ. ID. NO. 18), IFNα, 5'-gaatctctcctttctcctg-3'(SEQ. ID. NO. 19) and 5'-ctgacaac-ctcccaggcac-3'(SEQ. ID. NO. 20), IE1, 5'gcatagaatcaaggag-cacatgc-3'(SEQ. ID. NO. 21) and 5'-gtgatcaatgtgcgtgagcacc-3'(SEQ. ID. NO. 22). IFNα primers were designed to hybridize to conserved sequences present in all subtypes. For real time PCR, (GeneAmp 5700 sequence detection system, PE Biosystems, Foster city, Calif.) the primers and Taqman® probe (PE Biosystems) for detection of IFNβ were: 5'-gacatccctgaggagattaagca-3' (SEQ. ID. NO. 23), 5'-ggagcatctcatagatggtcaatg-3'(SEQ. ID. NO. 24), probe sequence 5'VIC-cgtcctccttctggaactgctgcag-TAMRA3'(SEQ. ID. NO. 25).

For determination of fold differences in message levels, the cycle number ($C_t$) which the relative fluorescence ($R_n$) crossed the manually set threshold value was determined using the analysis software provided with the 5700 SDS. Fold differences were calculated as follows:

$$[\log_2 IFN\beta C_t(HCMV+LT\alpha)-C_t(HCMV)] \div [\log_2 \beta actin C_t(HCMV+LT\alpha)-C_t(HCMV)].$$

A high level induction of IFNβ mRNA was observed only in NHDF that were both infected with HCMV and treated with LTα (FIG. 28a), LIGHT or LTα1β2 (FIG. 28b). The level of IFNβ message increased proportional to the amount of infectious virus suggesting the production of IFNβ occurred in virus-infected cells (FIG. 28a). The induction of IFNβ was rapid, peaking at 4–6 hr after infection, whereas trace levels of IFNα mRNA were detectable at 8–10 hours after infection (FIG. 28c). Treatment of NHDF with polyI:C, a potent IFN inducer, stimulated IFNα and β mRNA in the absence of lymphotoxins or virus. IFNβ was not detected in uninfected cells treated with lymphotoxins, but was minimally induced by HCMV alone. However, this level of IFNβ induction with virus alone was not sufficient to restrict CMV replication (FIG. 27).

Quantitative real time RT-PCR revealed an induction of IFNβ mRNA 48–103 fold (mean=77±26; n=4) above the level seen with virus alone (FIG. 28d). NHDF-IκBαM had significantly reduced levels of IFNβ mRNA after exposure to HCMV and LTα (8.6 fold induction vs 103 fold in LSXN control cells) (FIG. 28d and 28e), consistent with the refractory response to the antiviral effects of LT-related ligands. Importantly, no difference was seen in the ability of recombinant IFNβ to inhibit HCMV replication in NHDF-IκBαM cells indicating that NFκB activation is critical for the induction of IFNρ, and not for subsequent IFNβ mediated antiviral effects.

Example 21

Production and Characterization of an Anti-mouse LTβR Antibody Having Agonist Activity This example describes synthesis of an anti-mouse LTβR monoclonal antibody. This example also describes data demonstrating that the anti-mouse LTβR monoclonal antibody has LTβR agonist activity.

Monoclonal antibodies to mouse LTβR were prepared by immunization of Sprague-Dawley female rats with mouse LTβR-Fc fusion protein in Freund's adjuvant. Purified LTβR-Fc was produced by the standard baculovirus expression system and purified by Protein G affinity chromatography (Force et al., (1995) J. Immunol 155:5280). Hybridomas were produced by fusion of rat splenocytes with mouse P3X myeloma cell line by standard techniques. Specific antibody secreting cells were selected by a standard solid phase ELISA assay that employed plate bound mouse LTβR-Fc and detection of rat IgG with goat anti-Rat IgG conjugated to peroxidase (Immunochemical techniques. Part I: Hybridoma technology and monoclonal antibodies. Methods Enzymol. (1986)121:1–947). Specificity of monoclonal antibodies was assessed by staining a human cell line (HEK293) transfected with mouse LTβR cDNA using standard methods of DNA transfection. The rat anti mouse LTβR antibodies 3C8 (IgG1), 3H4 (IgG1), 4H8 (IgG2a) were purified from ascities fluid by ammonium sulfate precipitation and protein G affinity chromatography.

In order to examine activity of the LTβR antibodies, induction of Vascular cell adhesion molecule-1 (VCAM 1) with antibody to the mouse LTβR was studied. Mouse fibroblasts were stimulated with either rat anti-LTβR (3 μg/ml 3C8), human TNF (10 ng/ml) or left unstimulated for 16 hrs in tissue culture medium. The cells were harvested and stained with anti-mouse VCAM1 and FITC labeled second antibody. The fluorescence staining intensity was measured by flow cytometry.

The results show that both TNF and anti-LTβR monoclonal antibody stimulate increased expression of VCAM1 on mouse fibroblasts (FIG. 30). LTβR antibody is therefore an agonist of LTβR and, as such, is useful in practicing the methods of the invention.

Additional cell-based and in vivo animal assays for identifying such antibodies are described herein (see above and Example 22), and also are known in the art (see e.g., Rennert et al., (1998) Immunity 1:71; Force et al., (2000) J. Biol. Chem. 275:11121).

Example 22

LTαβ is Critical for Host Defense Against Murine CMV

This example describes data demonstrating that each of LTαβ and LIGHT participate in mediating host defense to MCMV. This example also describes data demonstrating that an anti-mouse LTβR monoclonal antibody having agonist activity protects against CMV infection in mice.

The antiviral activity that lymphotoxins exhibit against human CMV suggested these ligands may be conserved across species. The capacity of LTα-deficient mice (LTα/−) to respond to infection with mouse CMV (MCMV) was studied. MCMV replicates in most visceral organs and to high levels in spleen, liver, lung and salivary glands. Depending on virus dose, and the strain and age of the mice, MCMV can cause death from acute shock at 2–3 days post infection. However, the most common course is death at 5–7 days as a result of multiorgan disease, and in particular hepatic failure.

LTα-/- mice backcrossed to C57BL/6 mice for 8 generations (Banks et al., (1995) J. Immunol. 155:1685) and wildtype C57BL/6 mice were purchased from the Jackson Laboratories (Bar Harbor, Me.). The transgenic line expressing a soluble mouse LTβR/human IgG1-Fc fusion protein (LTβR-Fc Tg) on a Balb/c background was provided by R. Ettinger and H. O. McDevitt (Ettinger et al., (1996) Proc. Natl. Acad. Sci. 93:13102). These animals constitutively express the murine LTbR-Fc under the control of the human CMV promoter. The construct is specifically mutated in the CH2 domain to block binding to Fc receptors and complement activation. Serum levels of this soluble chimeric receptor were determined by ELISA (Ettinger et al., (1996) Proc. Natl. Acad. Sci. 93:13102); studies used animals with serum levels >1.2 µg/ml. Non-transgenic littermates served as controls. All mice were bred and housed under specific pathogen-free conditions and in accordance with institutional guidelines. In all experiments mice were age (6–12 weeks) and sex-matched.

Murine cytomegalovirus (MCMV; Smith strain) viral stocks were prepared from salivary gland extracts as described (Reddehase et al., (1985) J. Virol. 55:264). To determine both lethal and sublethal virus doses for acute MCMV infection in the different mouse strains, virus doses ranging from $5\times10^3$ to $1\times10^6$ PFU were injected by the intraperitoneal route into groups of 4 to 6 mice per virus dose and the mice monitored daily for morbidity and mortality over a period of 14 days.

LTα-/- mice (C57/BL6 background) were profoundly susceptible to lethal infection with MCMV requiring ~100 fold less virus than age matched C57/BL6 mice (FIG. 29 upper panel). At viral doses $>4\times10^4$ PFU (LD50 for LTα-/- mice=~$3\times10^4$ PFU) the LTα-/-mice succumbed at 5 to 7 days indicating hepatic failure as the likely cause of death. Similarly, when high doses of MCMV ($<3\times10^6$ PFU; LD50 for C57/BL6=~$2-3\times10^6$ PFU) were used to infect C57/BL6 controls, these mice also died between 5–7 days.

LTα-/- mice have defects in the development of peripheral lymphoid organs and also lack most of their NK and NK-T cells (Lizuka et al., (1999) Proc. Natl. Acad. Sci. USA 96:6336); Elewaut et al., (2000) J. Immunol. 165:671), which could account for their susceptibility to MCMV. However, mice expressing the LTβR-Fc decoy as a transgene, which have a normal complement of lymph nodes and NK and NK-T cells, were also susceptible to MCMV compared to transgene negative littermates (FIG. 29, lower panel). This result indicates that the developmental abnormalities in the LTα-/- mice are not likely to be responsible for the susceptibility of these mice to MCMV, and implicates LTαβ and LIGHT as potentially critical effector molecules in host defense to MCMV.

Normal mice treated with mouse LTβR-Fc fusion protein, a soluble injectable neutralizing agent specific for LTα1β2 or LIGHT, or mouse HVEM-Fc, which binds LTα or LIGHT, results in profound susceptibility of normal C57B1/6 mice to MCMV at a dose of virus that is 10 times below the amount that causes a lethal infection in this strain (Table 2). Treatment of mice with LTβR-Fc 3 days before infection with MCMV does not cause this susceptibility. By contrast, LTα deficient mice treated with a rat monoclonal antibody to mouse LTβR (a pool of 3C8 with 3H4 and 4H8) are protected compared to control LTα-/- mice as measured by the substantial delay in time (prolonged from death at 5 days to 9 days) to the lethality caused by MCMV (Table 3). The administration of anti-LTβR antibodies allows LTα deficient mice to resist lethal infection with MCMV demonstrating that antibodies to LTβR can be protective in vivo in MCMV infection.

TABLE 2

Resistance to MCMV is dependent on LTα1β2 and LIGHT

| MCMV only | LTβR-Fc | LTβR-Fc-72 hrs* | HVEM-Fc |
|---|---|---|---|
| 4/4 | 0/4 | 4/4 | 0/4 |

Normal C57/B16 mice were injected IP with 100 µg of purified mouse LTβR-Fc or mouse HVEM-Fc and 4 hrs later infected IP with $2\times10^5$ PFU MCMV (Smith strain). Morbidity and mortality were assessed daily for 13 days. Data represent number of surviving mice per total mice in each group at day 13. Death occurred at 5–6 days post infection.
*LTβR-Fc was administered 3 days prior to virus infection.

TABLE 3

LTβR signaling protects against lethal MCMV infection

| Time | Anti-LTβR/no virus | MCMV | Anti-LTβR + MCMV |
|---|---|---|---|
| Day 5 | 4/4 | 0/4 | 0/4 |
| Day 14 | 4/4 | 0/4 | 0/4* |

LTα-/- mice (groups of 4) were administered 100 µg of rat anti-mouse LTβR monoclonal antibody IP, followed by IP infection with MCMV $8\times10^4$ PFU (Smith strain) 4 hrs later. Animal morbidity and mortality was assessed daily. Data represent number of surviving mice per total mice in each group.
*Mice survived until day 9.

Together, these results reveal the role of lymphotoxins in establishing host defense to CMV. LTβR and TNFR1 agonists that mimic lymphotoxins, including antibodies that activate LTβR, are therefore useful for treatment of HCMV primary infection or reactivation of infection, such as in immune compromised patients with cancer or HIV that suffer from CMV hepatitis, nephritis, retinitis or disseminated disease. Treatment of patients with anti-LTβR antibody can inhibit HCMV reactivation caused by bone marrow transplantation or other tissue grafts. Finally, anti-LTβR antibody can be useful in treating disorders associated with CMV such as, arteriosclerosis or multiple sclerosis.

Although the invention has been described with reference to the presently preferred embodiment, it should be understood that various modifications can be made without departing from the spirit of the invention. Accordingly, the invention is limited only by the following claims.

What is claimed is:

1. A method for treating a subject having a CMV infection comprising contacting the subject with an amount of an agonist antibody or antigen binding fragment thereof that binds to lymphotoxin beta receptor (LTβR) sufficient to treat the CMV infection.

2. The method of claim 1, wherein the antibody is fully human.

3. The method of claim 1, wherein the antibody is humanized.

4. The method of claim 1, wherein CMV proliferation is reduced in the subject following treatment.

5. The method of claim 1, wherein CMV nucleic acid replication is reduced in the subject following treatment.

6. The method of claim 1, wherein the CMV infection is due to CMV reactivation from latency.

7. The method of claim 1, wherein the subject is immunosuppressed.

8. The method of claim 7, wherein the immunosuppression is due to HIV infection.

9. The method of claim 7, wherein the immunosuppression is due to a blood or bone marrow, organ, or tissue transplant.

10. The method of claim 1, wherein the subject is a neonate.

11. The method of claim 1, wherein the agonist antibody does not function by inducing death of cells infected with the CMV.

12. The method of claim 1, further comprising contacting the subject with an antiviral agent.

13. The method of claim 1, wherein said method comprises contacting the subject with an amount of said antigen binding fragment thereof sufficient to treat the CMV infection.

14. The method of claim 1, wherein the antibody is in a pharmaceutical composition.

15. A method for treating a subject having a CMV infection due to immuno suppression or reactivation of CMV from latency, comprising contacting the subject with an amount of an agonist antibody or antigen binding fragment thereof that binds to lymphotoxin beta receptor (LTβR) sufficient to treat CMV infection due to immunosuppression or reactivation of CMV from latency.

16. The method of claim 15, wherein the antibody is fully human.

17. The method of claim 15, wherein the antibody is humanized.

18. The method of claim 15, wherein CMV proliferation is reduced in the subject following treatment.

19. The method of claim 15, wherein CMV nucleic acid replication is reduced in the subject following treatment.

20. The method of claim 15, wherein the immunosuppression is due to HIV infection.

21. The method of claim 15, wherein the immunosuppression is due to a blood or bone marrow, organ, or tissue transplant.

22. The method of claim 15, wherein the subject is a neonate.

23. The method of claim 15, wherein the agonist antibody does not function by inducing death of cells infected with the virus.

24. The method of claim 15, further comprising contacting the subject with an antiviral agent.

25. The method of claim 15, wherein said method comprises contacting the subject with an amount of said antigen binding fragment thereof sufficient to treat the CMV infection due to immunosuppression or reactivation of CMV from latency.

26. The method of claim 15, wherein the antibody is in a pharmaceutical composition.

27. The method of claim 1, wherein the CMV infection is selected from CMV hepatitis, CMV retinitis, CMV pneumonitis and CMV nephritis.

28. The method of claim 1, wherein CMV protein expression is reduced in the subject following treatment.

29. The method of claim 15, wherein CMV protein expression is reduced in the subject following treatment.

30. The method of claim 7, wherein the immunosuppression is due to a tumor.

31. The method of claim 15, wherein the immunosuppression is due to a tumor.

* * * * *

UNITED STATES PATENT AND TRADEMARK OFFICE
CERTIFICATE OF CORRECTION

PATENT NO. : 7,118,742 B2
APPLICATION NO. : 09/967604
DATED : October 10, 2006
INVENTOR(S) : Carl Ware It is certified that error appears in the above-identified patent and that said Letters Patent is hereby corrected as shown below:

In the Specification

Col. 1, lines 18-20
replace "The United States Government has certain rights in this invention pursuant to grant nos. AI33068 and CA69381 awarded by National Institutes of Health (NIH), DHHS."
with --This invention was made with government support under Grants AI33068 and CA69381 awarded by the National Institutes of Health. The government has certain rights in the invention.--

Signed and Sealed this
Eighth Day of October, 2013

Teresa Stanek Rea
*Deputy Director of the United States Patent and Trademark Office*

SEQUENCE LISTING

<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 1
cggagatctg agttcatcct gctagctgg                                    29

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 2
ataggatccc ttggtctggt gctgacattc c                                 31

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 3
gacgtcagat cttcccacct ttcctccta                                    29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 4
gaacagagat ctcattgctc ctggctctg                                    29

<210> SEQ ID NO 5
<211> LENGTH: 1169
<212> TYPE: DNA
<213> ORGANISM: Homo sapiens
<220> FEATURE:
<221> NAME/KEY: CDS
<222> LOCATION: (49)..(771)

<400> SEQUENCE: 5
gaggttgaag gacccaggcg tgtcagccct gctccagaga ccttgggc atg gag gag    57
                                                    Met Glu Glu
                                                      1 agt gtc gta cgg ccc tca gtg ttt gtg gtg gat gga cag acc gac atc   105
Ser Val Val Arg Pro Ser Val Phe Val Val Asp Gly Gln Thr Asp Ile
      5                  10                  15 cca ttc acg agg ctg gga cga agc cac cgg aga cag tcg tgc agt gtg   153
Pro Phe Thr Arg Leu Gly Arg Ser His Arg Arg Gln Ser Cys Ser Val
 20                  25                  30                  35 gcc cgg gtg ggt ctg ggt ctc ttg ctg ttg ctg atg ggg gct ggg ctg   201
Ala Arg Val Gly Leu Gly Leu Leu Leu Leu Met Gly Ala Gly Leu
                 40                  45                  50

```
gcc gtc caa ggc tgg ttc ctc ctg cag ctg cac tgg cgt cta gga gag    249
Ala Val Gln Gly Trp Phe Leu Leu Gln Leu His Trp Arg Leu Gly Glu
             55                  60                  65 atg gtc acc cgc ctg cct gac gga cct gca ggc tcc tgg gag cag ctg    297
Met Val Thr Arg Leu Pro Asp Gly Pro Ala Gly Ser Trp Glu Gln Leu
         70                  75                  80 ata caa gag cga agg tct cac gag gtc aac cca gca gcg cat ctc aca    345
Ile Gln Glu Arg Arg Ser His Glu Val Asn Pro Ala Ala His Leu Thr
     85                  90                  95 ggg gcc aac tcc agc ttg acc ggc agc ggg ggg ccg ctg tta tgg gag    393
Gly Ala Asn Ser Ser Leu Thr Gly Ser Gly Gly Pro Leu Leu Trp Glu
100                 105                 110                 115 act cag ctg ggc ctg gcc tcc ctg agg ggc ctc agc tac cac gat ggg    441
Thr Gln Leu Gly Leu Ala Ser Leu Arg Gly Leu Ser Tyr His Asp Gly
                120                 125                 130 gcc ctt gtg gtc acc aaa gct ggc tac tac tac atc tac tcc aag gtg    489
Ala Leu Val Val Thr Lys Ala Gly Tyr Tyr Tyr Ile Tyr Ser Lys Val
            135                 140                 145 cag ctg ggc ggt gtg ggc tgc ccg ctg ggc ctg gcc agc acc atc acc    537
Gln Leu Gly Gly Val Gly Cys Pro Leu Gly Leu Ala Ser Thr Ile Thr
        150                 155                 160 cac ggc ctc tac aag cgc aca ccc cgc tac ccc gag gag ctg gag ctg    585
His Gly Leu Tyr Lys Arg Thr Pro Arg Tyr Pro Glu Glu Leu Glu Leu
    165                 170                 175 ttg gtc agc cag cag tca ccc tgc gga cgg gcc acc agc agc tcc cgg    633
Leu Val Ser Gln Gln Ser Pro Cys Gly Arg Ala Thr Ser Ser Ser Arg
180                 185                 190                 195 gtc tgg tgg gac agc agc ttc ctg ggt ggt gta cac ctg gag gct        681
Val Trp Trp Asp Ser Ser Phe Leu Gly Gly Val His Leu Glu Ala
                200                 205                 210 ggg gag gag gtg gtc gtc cgt gtg ctg gat gaa cgc ctg gtt cga ctg    729
Gly Glu Glu Val Val Val Arg Val Leu Asp Glu Arg Leu Val Arg Leu
            215                 220                 225 cgt gat ggt acc cgg tct tac ttc ggg gct ttc atg gtg tga            771
Arg Asp Gly Thr Arg Ser Tyr Phe Gly Ala Phe Met Val
        230                 235                 240 aggaaggagc gtggtgcatt ggacatgggt ctgacacgtg agaactcag agggtgcctc     831 aggggaaaga aaactcacga agcagaggct gggcgtggtg gctctcgcct gtaatcccag    891
cactttggga ggccaaggca ggcggatcac ctgaggtcag gagttcgaga ccagcctggc    951
taacatggca aaaccccatc tctactaaaa atacaaaaat tagccggacg tggtggtgcc   1011
tgcctgtaat ccagctactc aggaggctga ggcaggataa ttttgcttaa acccgggagg   1071
cggaggttgc agtgagccga gatcacacca ctgcactcca acctgggaaa cgcagtgaga   1131
ctgtgcctca aaaaaaaaaa aaaaaaaaaa aaaaaaaa                          1169

<210> SEQ ID NO 6
<211> LENGTH: 240
<212> TYPE: PRT
<213> ORGANISM: Homo sapiens

<400> SEQUENCE: 6

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45
```

-continued

| | | | | | | | | | | | | |
|---|---|---|---|---|---|---|---|---|---|---|---|---|
| Ala | Gly | Leu | Ala | Val | Gln | Gly | Trp | Phe | Leu | Leu | Gln | Leu | His | Trp | Arg |
| | 50 | | | | | 55 | | | | | 60 | | | | |
| Leu | Gly | Glu | Met | Val | Thr | Arg | Leu | Pro | Asp | Gly | Pro | Ala | Gly | Ser | Trp |
| 65 | | | | | 70 | | | | | 75 | | | | | 80 |
| Glu | Gln | Leu | Ile | Gln | Glu | Arg | Arg | Ser | His | Glu | Val | Asn | Pro | Ala | Ala |
| | | | | 85 | | | | | 90 | | | | | 95 | |
| His | Leu | Thr | Gly | Ala | Asn | Ser | Ser | Leu | Thr | Gly | Ser | Gly | Gly | Pro | Leu |
| | | | 100 | | | | | 105 | | | | | 110 | | |
| Leu | Trp | Glu | Thr | Gln | Leu | Gly | Leu | Ala | Ser | Leu | Arg | Gly | Leu | Ser | Tyr |
| | | | 115 | | | | | 120 | | | | | 125 | | |
| His | Asp | Gly | Ala | Leu | Val | Val | Thr | Lys | Ala | Gly | Tyr | Tyr | Tyr | Ile | Tyr |
| | | | 130 | | | | 135 | | | | | 140 | | | |
| Ser | Lys | Val | Gln | Leu | Gly | Gly | Val | Gly | Cys | Pro | Leu | Gly | Leu | Ala | Ser |
| 145 | | | | | 150 | | | | | 155 | | | | | 160 |
| Thr | Ile | Thr | His | Gly | Leu | Tyr | Lys | Arg | Thr | Pro | Arg | Tyr | Pro | Glu | Glu |
| | | | | 165 | | | | | 170 | | | | | 175 | |
| Leu | Glu | Leu | Leu | Val | Ser | Gln | Gln | Ser | Pro | Cys | Gly | Arg | Ala | Thr | Ser |
| | | | 180 | | | | | 185 | | | | | 190 | | |
| Ser | Ser | Arg | Val | Trp | Trp | Asp | Ser | Ser | Phe | Leu | Gly | Gly | Val | Val | His |
| | | 195 | | | | | 200 | | | | | 205 | | | |
| Leu | Glu | Ala | Gly | Glu | Glu | Val | Val | Val | Arg | Val | Leu | Asp | Glu | Arg | Leu |
| | 210 | | | | | 215 | | | | | 220 | | | | |
| Val | Arg | Leu | Arg | Asp | Gly | Thr | Arg | Ser | Tyr | Phe | Gly | Ala | Phe | Met | Val |
| 225 | | | | | 230 | | | | | 235 | | | | | 240 |